United States Patent [19]
von dem Bussche-Hünnefeld et al.

[11] Patent Number: 5,928,999
[45] Date of Patent: Jul. 27, 1999

[54] SUBSTITUTED 3-PHENYLPYRAZOLES

[75] Inventors: Christoph-Sweder von dem Bussche-Hünnefeld, Mannheim; Ralf Klintz, Gruenstadt; Gerhard Hamprecht, Weinheim; Elisabeth Heistracher, Ludwigshafen; Peter Schäfer, Ottersheim; Peter Münster, Römerberg; Klaus Ditrich, Gönnheim; Hartmann König, Heidelberg; Karl-Otto Westphalen, Speyer; Matthias Gerber, Limburgerhof; Helmut Walter, Obrigheim, all of Germany

[73] Assignee: BASF Aktiengesellschaft, Ludwigshafen, Germany

[21] Appl. No.: 08/737,815
[22] PCT Filed: May 10, 1995
[86] PCT No.: PCT/EP95/01772
§ 371 Date: Nov. 19, 1996
§ 102(e) Date: Nov. 19, 1996
[87] PCT Pub. No.: WO95/32188
PCT Pub. Date: Nov. 30, 1995

Related U.S. Application Data

[30] Foreign Application Priority Data

May 20, 1994 [DE] Germany .............................. 44 17 837

[51] Int. Cl.⁶ .......................... A01N 43/56; C07D 231/20
[52] U.S. Cl. ......................... 504/282; 548/366.1
[58] Field of Search .......................... 548/366.1; 504/282

[56] References Cited

U.S. PATENT DOCUMENTS 4,008,249  2/1977  Fischer et al. .......................... 260/310

FOREIGN PATENT DOCUMENTS

| | | |
|---|---|---|
| 443 059 | 8/1991 | European Pat. Off. . |
| 447 055 | 9/1991 | European Pat. Off. . |
| 2262663 | 9/1975 | France . |
| 372460 | 6/1988 | Japan . |
| 2300173 | 9/1988 | Japan . |
| 3093774 | 9/1989 | Japan . |
| 3151367 | 11/1989 | Japan . |
| 347180 | 4/1990 | Japan . |
| 381275 | 5/1990 | Japan . |
| 6199806 | 9/1992 | Japan . |
| 2073172 | 10/1981 | United Kingdom . |
| 92/01509 | 2/1992 | WIPO . |
| 92/06962 | 4/1992 | WIPO . |
| 93/25535 | 12/1993 | WIPO . |
| 94/05660 | 3/1994 | WIPO . |

OTHER PUBLICATIONS

Chem. Abst., vol. 122, No. 7, Feb. 13, 1995, Abs. No. 81124f.
Chem. Abst., vol. 115, No. 5, Aug. 5, 1991.
Chem. Abst., vol. 121, 1994, Abst. Nos. 300885q and 300886r.

Primary Examiner—Robert W. Ramsuer
Attorney, Agent, or Firm—Keil & Weinkauf

[57] ABSTRACT

Substituted 3-phenylpyrazoles of formula (I), where $R^1$ is H, or a substituent; $R^2$ is CN, $CF_3$, halogen; $R^3$ is H, alkyl, halogenalkyl; $R^4$ is $C_1$–$C_4$ alkyl, $C_1$–$C_4$ halogenalkyl; $R^5$ is H, $NO_2$, halogen, —COOR, optionally substituted aminocarbonyl (where R is H, a substituent); and Z is —O—, —S—, —SO—, —$SO_2$—; and argriculturally usable salts thereof, for use as herbicides.

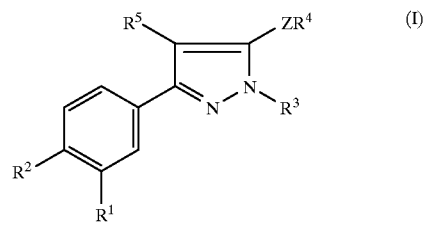

7 Claims, No Drawings

SUBSTITUTED 3-PHENYLPYRAZOLES

This application is a 371 of PCT/EP 95/01772 filed May 20, 1994.

The present invention relates to novel substituted 3-phenylpyrazoles of the formula I

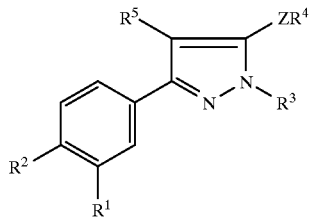

in which $R^1$ is hydrogen, cyano, nitro, halogen, $C_1$–$C_8$-alkyl, $C_2$–$C_8$-alkenyl, $C_2$–$C_8$-alkynyl, $C_1$–$C_8$-haloalkyl, $C_2$–$C_8$-haloalkenyl, $C_2$–$C_8$-haloalkynyl, cyano-$C_1$–$C_4$-alkyl, $C_1$–$C_8$-alkyl—O—$R^6$, $C_1$–$C_8$-alkyl—O—CO—$R^6$, $C_2$–$C_8$-alkenyl—O—$R^6$, $C_2$–$C_8$-alkynyl—O—$R^6$, $C_1$–$C_8$-alkyl—S—$R^6$, $C_2$–$C_8$-alkenyl—S—$R^6$, $C_2$–$C_8$-alkynyl—S—$R^6$, $C_1$–$C_8$-alkyl—SO—$R^6$, $C_2$–$C_8$-alkenyl—SO—$R^6$, $C_2$–$C_8$-alkynyl—SO—$R^6$, $C_1$–$C_8$-alkyl—$SO_2$—$R^6$, $C_2$–$C_8$-alkenyl—$SO_2$—$R^6$, $C_2$–$C_8$-alkynyl—$SO_2$—$R^6$, —O—$R^6$, —S—$R^6$, —SO—$R^6$, —$SO_2$—$R^6$, —$SO_2$—Cl, —$SO_2$—O—$R^6$, —$SO_2$—N($R^7$, $R^8$), —$SO_2$—N($R^7$)—CO—$R^9$, —N($R^7$, $R^8$), —N($R^7$)—N($R^8$, $R^{32}$), —N=N—CO—$R^9$, —N($R^7$)—N($R^8$)—CO—$R^9$, —N($R^{10}$)—CO—$R^9$, —N($R^{10}$)—$SO_2$—$R^{11}$, —N($SO_2$—$R^{11}$)($SO_2$—$R^{12}$), —N($SO_2$—$R^{11}$)(CO—$R^9$), —NH—CO—O—$R^6$, —O—CO—NH—$R^7$, —O—CO—$R^9$, —NH—CO—NH—$R^{13}$, —O—CS—N($C_1$–$C_4$-alkyl)$_2$, —O—CS—$NH_2$, —A—CO—O—$R^6$, —A—P(O)(O$R^6$)$_2$, —O—($C_1$–$C_4$-alkyl)—COO$R^6$, —A—CO—O—N=C($R^{14}$, $R^{15}$), —A—CO—O—$CH_2$—O—N=C($R^{16}$, $R^{17}$), —A—CO—O—C($R^{18}$, $R^{19}$)—$CH_2$—O—N=C($R^{16}$, $R^{17}$), —A—CO—N($R^7$, $R^8$), —A—CS—N($R^7$, $R^8$), —A—CO—NH—$SO_2$—($C_1$–$C_4$-alkyl), —A—CO—$R^{20}$, —A—CH=N—O—$R^6$, —A—CH(X$R^{21}$, Y$R^{22}$), —A—C($R^{20}$)=N—O—$R^6$, —($C_1$–$C_4$-alkyl)—O—($C_1$–$C_4$-alkyl)—C($R^{19}$)=N—O($C_1$–$C_4$-alkyl), isoxazolidinylcarbonyl, —A—CO—N($R^7$)—C($R^8$, $R^{18}$)—COO$R^6$, —$SO_2$—N($R^7$)—C($R^8$, $R^{18}$)—COO$R^6$, —$SO_2$—N($R^7$)—C($R^8$, $R^{18}$)—CO—N($R^{32}$, $R^{33}$),

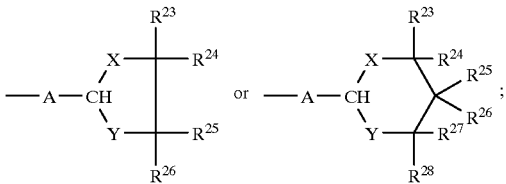

$R^2$ is cyano, trifluoromethyl or halogen;
$R^3$ is hydrogen, $C_1$–$C_4$-alkyl or $C_1$–$C_4$-haloalkyl;
$R^4$ is $C_1$–$C_4$-alkyl or $C_1$–$C_4$-haloalkyl;
$R^5$ is hydrogen, nitro, halogen, —COO$R^{29}$ or —CO—N($R^{30}$, $R^{31}$);
Z is oxygen, sulfur, —SO— or —$SO_2$—;
X and Y independently of one another are oxygen or sulfur;
A is a chemical bond, methylene, ethylene, 1,3-propylene, 1,4-butylene, vinylene or 1,4-butadienylene;
$R^6$, $R^{29}$ independently of one another are hydrogen, $C_1$–$C_8$-alkyl, $C_1$–$C_8$-haloalkyl, $C_3$–$C_7$-cycloalkyl which may in turn carry from one to three $C_1$–$C_3$-alkyl radicals, $C_3$–$C_6$-alkenyl, $C_5$–$C_7$-cycloalkenyl which may in turn carry from one to three $C_1$–$C_3$-alkyl radicals, $C_3$–$C_6$-haloalkenyl, cyano-$C_1$–$C_8$-alkyl, $C_3$–$C_6$-alkynyl, $C_1$–$C_4$-alkoxy-$C_1$–$C_4$-alkyl, 2-tetrahydrofuryl-$C_1$–$C_8$-alkyl, 3-oxetanyl, 3-thietanyl, carboxyl-$C_1$–$C_6$-alkyl, ($C_1$–$C_8$-alkoxy)carbonyl-$C_1$–$C_6$-alkyl, $C_1$–$C_4$-alkoxy-($C_1$–$C_4$-alkoxy)carbonyl-$C_1$–$C_6$-alkyl, cyclopropylmethyl, (1-methylthiocycloprop-1-yl)methyl, $C_3$–$C_9$-($\alpha$-alkylalkylidene)-iminooxy-$C_1$–$C_6$-alkyl, ($C_1$–$C_4$-alkyl)carbonyl, $C_1$–$C_4$-alkyl which is substituted by —C($R^{19}$)=N—O—($C_1$–$C_4$-alkyl), —C($R^{19}$)=N—O—($C_1$–$C_4$-haloalkyl), —C($R^{19}$)=N—O—($C_3$–$C_6$-alkenyl), —C($R^{19}$)=N—O—($C_3$–$C_6$-haloalkenyl) or —C($R^{19}$)=N—O—($C_1$–$C_4$-alkyl),—$R^{34}$, phenyl, phenyl-$C_1$–$C_6$-alkyl, phenyl-$C_2$–$C_6$-alkenyl, phenyl-$C_3$–$C_6$-alkynyl or phenoxy-$C_1$–$C_6$-alkyl, the phenyl ring being able in each case to be unsubstituted or in turn to carry from one to three radicals selected from the group consisting of halogen, nitro, cyano, $C_1$–$C_4$-alkyl, $C_1$–$C_4$-alkoxy, $C_1$–$C_4$-alkylthio, $C_1$–$C_4$-haloalkyl and $C_2$–$C_6$-alkenyl, 5- or 6-membered heteroaryl, heteroaryl-$C_1$–$C_6$-alkyl, heteroaryl-$C_3$–$C_6$-alkenyl, heteroaryl-$C_3$–$C_6$-alkynyl or heteroaryloxy-$C_1$–$C_6$-alkyl, the heteroaromatic radical containing in each case from one to three heteroatoms selected from a group consisting of one or two nitrogen atoms and one oxygen or sulfur atom, and the heteroaromatic radical being able, if desired, to carry on each substitutable ring member a radical selected in each case from the group consisting of hydroxyl, halogen, $C_1$–$C_4$-haloalkyl, $C_1$–$C_4$-alkoxy, $C_1$–$C_4$-alkylthio and $C_1$–$C_4$-alkyl;

$R^7$, $R^8$, $R^{13}$, $R^{30}$, $R^{31}$, $R^{32}$, $R^{33}$ independently of one another are hydrogen, $C_1$–$C_8$-alkyl, $C_1$–$C_8$-alkyl, $C_1$–$C_8$-haloalkyl, $C_2$–$C_8$-alkenyl, $C_2$–$C_8$-alkynyl, $C_1$–$C_4$-alkoxy-$C_1$–$C_4$-alkyl, $C_1$–$C_4$-alkyl-thio-$C_1$–$C_4$-alkyl, cyano-$C_1$–$C_8$-alkyl, carboxyl-$C_1$–$C_4$-alkyl, ($C_1$–$C_4$-alkoxy)carbonyl-$C_1$–$C_4$-alkyl, $C_1$–$C_4$-alkylsulfonyl-$C_1$–$C_4$-alkyl, $C_3$–$C_8$-cycloalkyl, $C_1$–$C_6$-alkoxy, ($C_3$–$C_6$-cyclo-alkoxy)carbonyl-$C_1$–$C_4$-alkyl, $C_1$–$C_4$-alkoxy-($C_1$–$C_4$-alkoxy)carbonyl-$C_1$–$C_4$-alkyl, ($C_1$–$C_4$-alkyl)carbonyl, ($C_1$–$C_4$-haloalkyl)-carbonyl, tetrahydrofuran-2-on-3-yl, phenyl, phenyl-$C_1$–$C_4$-alkyl, in which the phenyl ring may in each case be unsubstituted or may carry one to three radicals selected from the group consisting of halogen, nitro, cyano, $C_1$–$C_4$-alkyl, $C_1$–$C_4$-alkoxy, $C_1$–$C_4$-alkylthio, $C_1$–$C_4$-haloalkyl and $C_2$–$C_6$-alkenyl, 5- or 6-membered heteroaryl or heteroaryl-$C_1$–$C_4$-alkyl, the heteroaromatic radical containing from one to three heteroatoms selected from a group consisting of one or two nitrogen atoms and one oxygen or sulfur atom, and the heteroaromatic radical being able, if desired, to carry on each substitutable ring atom a radical selected from the group consisting of hydroxyl, halogen, $C_1$–$C_4$-alkyl, $C_1$–$C_4$-alkoxy, $C_1$–$C_4$-alkylthio and $C_1$–$C_4$-haloalkyl;
or $R^7$ and $R^8$ and/or $R^{30}$ and $R^{31}$ are together a tetramethylene, pentamethylene or ethyleneoxyethylene chain which may if desired carry from one to three $C_1$–$C_4$-alkyl radicals and/or a radical —COO$R^6$;

$R^9$ is hydrogen, $C_1$–$C_6$-alkyl, $C_1$–$C_6$-haloalkyl, $C_1$–$C_4$-alkoxy-$C_1$–$C_4$-alkyl, $C_3$–$C_7$-cycloalkyl which may in turn carry from one to three radicals selected from the group consisting of halogen, $C_1$–$C_4$-alkyl, $C_1$–$C_4$-alkoxy and $C_{12}$–$C_4$-alkylthio, phenyl or phenyl-$C_1$–$C_6$-alkyl, in which the phenyl ring may in each case be unsubstituted or may carry from one to three radicals selected from the group consisting of halogen, nitro, $C_1$–$C_4$-alkyl, $C_1$–$C_4$-alkoxy, $C_1$–$C_4$-alkylthio and $C_1$–$C_4$-haloalkyl;

$R^{10}$ is hydrogen, $C_1$–$C_4$-alkyl, $C_3$–$C_6$-alkenyl, $C_3$–$C_6$-alkynyl, $C_1$–$C_4$-alkoxy-$C_1$–$C_4$-alkyl or the equivalent of an agriculturally usable cation;

$R^{11}$ and $R^{12}$ independently of one another are $C_1$–$C_4$-alkyl, $C_1$–$C_4$-haloalkyl, phenyl which may be unsubstituted or may carry from one to three substituents in each case selected from the group consisting of halogen, nitro, $C_1$–$C_4$-alkyl, $C_1$–$C_4$-alkoxy, $C_1$–$C_4$-alkylthio and $C_1$–$C_4$-haloalkyl, or 5- or 6-membered heteroaryl containing from one to three heteroatoms selected from the group consisting of 2 nitrogen atoms and one oxygen or sulfur atom, the heteroaromatic radical being able to be unsubstituted or to carry, if desired, on each substitutable ring member a substituent in each case selected from the group consisting of hydroxyl, halogen, $C_1$–$C_4$-alkyl, $C_1$–$C_4$-haloalkyl, $C_1$–$C_4$-alkoxy and $C_1$–$C_4$-alkylthio;

$R^{14}$ is $C_1$–$C_6$-alkyl, $C_1$–$C_6$-alkylthio, ($C_1$–$C_6$-alkoxy)carbonyl or ($C_1$–$C_6$-alkoxy)carbonyl-$C_1$–$C_4$-alkyl;

$R^{15}$ is $C_1$–$C_6$-alkyl, trifluoromethyl, $C_1$–$C_6$-alkoxy-$C_1$–$C_4$-alkyl, ($c_1$–$C_6$-alkoxy)carbonyl-$C_1$–$C_4$-alkyl, di-[($C_1$–$C_6$-alkoxy)carbonyl]-$C_1$–$C_4$-alkyl, $C_3$–$C_6$-cycloalkyl, $C_1$–$C_6$-alkoxy, $C_1$–$C_6$-alkylthio, ($C_1$–$C_6$-alkylthio, ($C_1$–$C_6$-alkoxy)carbonyl, 2-furyl or phenyl, both of which may be unsubstituted or, if desired, may carry from one to three radicals selected from the group consisting of halogen, $C_1$–$C_4$-alkyl and $C_1$–$C_4$-alkoxy;

or $R^{14}$ and $R^{15}$ together with the carbon atom to which they are attached, are a cyclopentane or cyclohexane ring which may if desired in turn carry from one to three $C_1$–$C_4$-alkyl radicals;

$R^{16}$ is hydrogen or $C_1$–$C_6$-alkyl;

$R^{17}$ is $C_1$–$C_6$-alkyl, $C_3$–$C_6$-cycloalkyl or phenyl;

$R^{18}$ is hydrogen or $C_1$–$C_4$-alkyl;

$R^{19}$ hydrogen, $C_1$–$C_4$-alkyl, phenyl or benzyl;

$R^{20}$ is hydrogen, cyano, halogen, $C_1$–$C_4$-alkyl, $C_1$–$C_4$-alkylthio, $C_2$–$C_4$-alkenyl, $C_1$–$C_4$-haloalkyl, $C_1$–$C_4$-alkoxy-$C_1$–$C_4$-alkyl, di-($C_1$–$C_4$-alkoxy)-$C_1$–$C_4$-alkyl, $C_1$–$C_4$-alkylthio-$C_1$–$C_4$-alkyl, (1,3-dioxolan-2-yl)-$C_1$–$C_4$-alkyl or (1,3-dioxan-2-yl)-$C_1$–$C_4$-alkyl;

$R^{21}$ and $R^{22}$ independently of one another are $C_1$–$C_8$-alkyl, $C_1$–$C_8$-haloalkyl or $C_1$–$C_4$-alkoxy-$C_1$–$C_4$-alkyl;

$R^{23}$, $R^{24}$, $R^{25}$, $R^{26}$, $R^{27}$ and $R^{28}$ independently of one another are hydrogen, cyano, $C_1$–$C_8$-alkyl, $C_1$–$C_8$-haloalkyl, $C_1$-$C_4$-alkoxy-$C_1$–$C_4$-alkyl, $C_1$–$C_8$-alkoxy, $C_1$–$C_4$-alkoxy-$C_1$–$C_4$-alkoxy, —CO—O—$R^6$, —CO—N($R^7$,$R^8$), —CO—$R^{20}$, —S—$R^6$, —SO$_2$—$R^6$, —O—CO—$R^9$ or $C_3$–$C_7$-cycloalkyl which may in turn carry from one to three radicals selected from the group consisting of halogen, $C_1$–$C_4$-alkyl, $C_1$–$C_4$-alkoxy and $C_1$–$C_4$-alkylthio;

$R^{34}$ is phenyl or 5- or 6-membered heteroaryl containing from one to three heteroatoms selected from the group consisting of 2 nitrogen atoms and one oxygen or sulfur atom, each phenyl or heteroaryl ring being able to be unsubstituted or, if desired, to carry on each substitutable ring member a substituent in each case selected from the group consisting of hydroxyl, nitro, cyano, halogen, $C_1$–$C_4$-alkyl, $C_1$–$C_4$-haloalkyl, $C_1$–$C_4$-alkoxy and $C_1$–$C_4$-alkylthio, and to the agriculturally usable salts of I.

The invention also relates to the use of these compounds as herbicides, to herbicidal compositions which comprise the compounds I as active substances, to methods of producing these herbicidal compositions and to methods of controlling unwanted plant growth using the compounds I.

JP 03/151 367 describes herbicidally active 1-(1-alkyl-4-halo-5-haloalkoxy-1H-pyrazol-3-yl)-4,6-dihalophenyl derivatives having the various substituents in position 3 of the phenyl ring, especially compounds having the following pattern of substitution IIa:

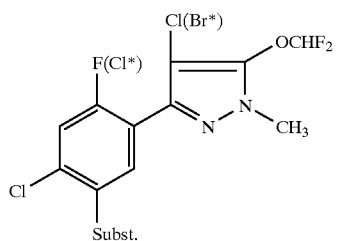

IIa

*) in each case one compound

Furthermore, EP-A 443 059 teaches that 1-alkyl- and 1-haloalkyl-3-(4-chloro-6-halophenyl)-pyrazoles and -4-halopyrazoles which carry particular substituents in position 3 of the phenyl ring and which are substituted in position 5 of the pyrazole ring by hydroxyl, mercapto, lower alkoxy, alkylthio, haloalkoxy or haloalkylthio are suitable for controlling unwanted plants.

Furthermore, JP-A 03/072 460 discloses that 3-substituted phenyl-pyrazoles of the formula IIb

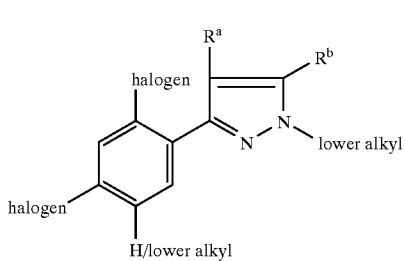

IIb in which $R^a$ is hydrogen, halogen or cyano and $R^6$ is lower alkoxy, haloalkoxy, alkylthio, haloalkylthio, alkylsulfinyl, haloalkylsulfinyl, alkylsulfonyl or haloalkylsulfonyl are herbicidally active.

EP-A 447 055 discloses that 1-(lower alkyl)3-(4-chloro-6halophenyl)-4-halo-5-difluoromethoxypyrazoles which carry an alkylthiocarbonyl, alkenylthiocarbonyl or benzylthiocarbonylmethoxy-carbonyl group in position 3 of the phenyl ring exhibit herbicidal activity.

In accordance of the teaching of JP-A 03/047 180 and JP-A 03/081 275 pyrazole derivatives, inter alia, of the formulae IIc and IId

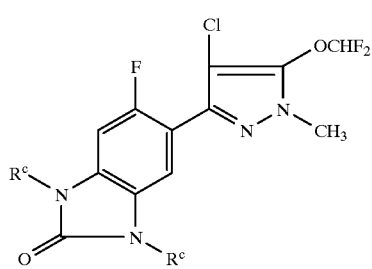

IIc

-continued

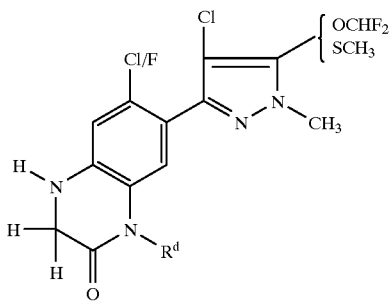

in which

R$^c$ is hydrogen, methyl or allyl and

R$^d$ is hydrogen, ethyl, allyl or propargyl are suitable as herbicides.

According to JP-A 02/300 173 and JP-A 03/093 774, specific 1-alkyl-3-phenylpyrazoles which may carry from one to four halogen atoms on the phenyl ring likewise exhibit herbicidal activity. Particular mention is made of 1-methyl-3-(2,4-dichlorophenyl)pyrazoles and three 1-methyl-5-chloro-3-(2-fluoro-4-chlorophenyl)pyrazoles.

Finally, WO 92/06962 describes herbicidal 4-halo-5-haloalkyl-3-phenylpyrazoles having various substituents on the phenyl ring.

The herbicidal properties of the known herbicides with respect to weed plants, however, are above to give only limited satisfaction.

It is an object of the present invention therefore to provide novel herbicidally active compounds which can be used to give better, targeted control of unwanted plants than hitherto.

We have found that this object is achieved by the substituted 3-phenylpyrazoles of the formula I. We have also found herbicidal compositions which comprise the compounds I and possess a very good herbicidal activity. Moreover, we have found methods of producing these compositions and methods of controlling unwanted plant growth using the compounds I.

With regard to the use of the substituted 3-phenylpyrazoles I as herbicides, preferred compounds I are those in which, in each case individually or in combination:

R$^1$ is hydrogen, nitro, halogen, $C_1$–$C_8$-alkyl, $C_1$–$C_8$-haloalkyl, $C_1$–$C_8$-alkyl—O—R$^6$, $C_1$–$C_8$-alkyl—O—CO—R$^6$, $C_1$–$C_8$-alkyl—S—R$^6$, $C_1$–$C_8$-alkyl—SO—R$^6$, $C_1$–$C_8$-alkyl—SO$_2$—R$^6$, —O—R$^6$, —SO$_2$—R$^6$, —SO$_2$—O—R$^6$, —SO$_2$-N(R$^7$, R$^8$), —N(R$^7$, R$^8$), —N(R$^8$, R$^{32}$), —N=N—CO—R$^9$, —N(R$^7$)—N(R$^8$)—CO—R$^9$, —N(R$^{10}$)—CO—R$^9$, —N(R$^{10}$)—SO$_2$—R$^{11}$, —N(SO$_2$—R$^{11}$) (SO$_2$—R$^{12}$), —A—CO—O—R$^6$, —A—CO—O—C(R$^{18}$, R$^{19}$)—CH$_2$—O—N=C(R$^{16}$, R$^{17}$), —A—CO—N(R$^7$, R$^8$), —A—CO—R$^{20}$, —A—CH(XR$^{21}$, YR$^{22}$), —(C$_1$–C$_4$-alkyl)—O—(C$_1$–C$_4$-alkyl)—C(R$^{19}$)=N—O—(C$_1$–C$_4$-alkyl), —A—CO—N(R$^7$)—C(R$^8$, R$^{18}$)—COOR$^6$, —SO$_2$—N(R$^7$)—C(R$^8$, R$^{18}$)—COOR$^6$, —SO$_2$—N(R$^7$)—C(R$^8$, R$^{18}$)—CO—N(R$^{32}$, R$^{33}$),

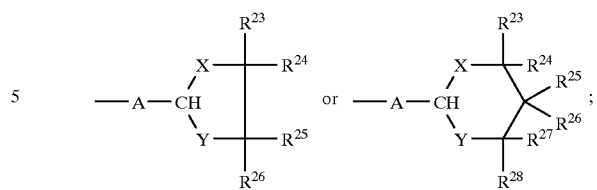

particular preference is given to hydrogen, nitro, $C_1$–$C_8$-alkyl, $C_1$–$C_8$-haloalkyl, $C_1$–$C_8$-alkyl—O—R$^6$, $C_1$–$C_8$-Alkyl—O—CO—R$^6$, $C_1$–$C_8$-alkyl—S—R$^6$, $C_1$–$C_8$-alkyl—SO—R$^6$, $C_1$–$C_8$-alkyl—SO$_2$—R$^6$, —SO$_2$-R$^6$, —SO$_2$—O—R$^6$, —SO$_2$—N(R$^7$, R$^8$), —N(R$^7$, R$^8$), —N(R$^7$)—N(R$^8$, R$^{32}$), —N=—CO—R$^9$, —N(R$^7$)—N(R$^8$)—CO—R$^9$, —N(R$^{10}$)—CO—R$^9$, —N(R$^{10}$)—SO$_2$—R$^{11}$, —N(SO$_2$—R$^{11}$) (SO$_2$—R$^{12}$), —A—CO—O—R$^6$, —A—CO—N(R$^7$, R$^8$), —A—CO—R$^{20}$, —A—CO—N(R$^7$)—C(R$^8$, R$^{18}$)—COOR$^6$, —SO$_2$—N(R$^7$)—C(R$^8$, R$^{18}$)—COOR$^6$, —SO$_2$—N(R$^7$)—C(R$^8$, R$^{18}$)—CO—N(R$^{32}$, R$^{33}$),

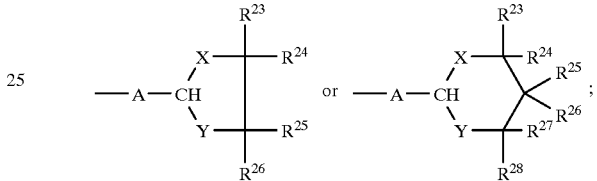

R$^2$ is cyano, trifluoromethyl or halogen;

R$^3$ is $C_1$–$C_4$-alkyl or $C_1$–$C_4$-haloalkyl;

R$^4$ is $C_1$–$C_4$-alkyl or $C_1$–$C_4$-haloalkyl;

R$^5$ is nitro, halogen, —COOR$^{29}$ or —CO—N(R$^{30}$, R$^{31}$);

particular preference is given to halogen;

Z is oxygen or sulfur;

X and Y are oxygen or sulfur;

A is a chemical bond, methylene, ethylene or vinylene

R$^6$ and R$^{29}$ independently of one another are hydrogen, $C_1$–$C_8$-alkyl, $C_1$–$C_8$-haloalkyl, $C_3$–$C_6$-cycloalkyl which may in turn carry one or two $C_1$–$C_3$-alkyl radicals, $C_3$–$C_6$-alkenyl, $C_3$–$C_6$-haloalkenyl, cyano-$C_1$–$C_4$-alkyl, $C_3$–$C_6$-alkynyl, $C_1$–$C_2$-alkoxy-$C_1$–$C_2$-alkyl, carboxyl-$C_1$–$C_6$-alkyl, ($C_1$–$C_4$-alkoxy)carbonyl-$C_1$–$C_4$-alkyl, cyclopropylmethyl, $C_1$–$C_4$-alkyl which is substituted by —C(R$^{19}$)=N—O—($C_1$–$C_4$-alkyl), —C(R$^{19}$)=N—O—O($C_1$–$C_4$-haloalkyl), —C(R$^{19}$)=N—O—($C_1$–$C_4$-alkyl)phenyl, phenyl, phenyl-$C_1$–$C_4$-alkyl, phenyl-$C_2$–$C_4$-alkenyl or phenoxy-$C_1$–$C_4$-alkyl, the phenyl ring being able in each case to be unsubstituted or in turn to carry from one to three radicals selected from the group consisting of halogen, nitro, cyano, $C_1$–$C_4$-alkyl, $C_1$–$C_4$-alkoxy, $C_1$–$C_4$-alkylthio, $C_1$–$C_4$-haloalkyl and $C_2$–$C_6$-alkenyl, 5- or 6-membered heteroaryl or heteroaryl-$C_1$–$C_6$-alkyl, the heteroaromatic radical containing in each case form one to three heteroatoms selected from a group consisting of one or two nitrogen atoms and one oxygen or sulfur atoms, and the heteroaromatic radical being able if desired to carry on each substitutable ring atom a radical selected from the group consisting of hydroxyl, halogen, $C_1$–$C_4$-haloalkyl, $C_1$–$C_4$-alkoxy, $C_1$–$C_4$-alkylthio and $C_1$–$C_4$-alkyl;

R$^7$, R$^8$, R$^{13}$, R$^{30}$, R$^{31}$, R$^{32}$ and R$^{33}$ independently of one another are hydrogen, $C_1$–$C_4$-alkyl, $C_1$–$C_4$-haloalkyl, $C_2$–$C_4$-alkenyl, $C_2$–$C_4$-alkynyl, $C_1$–$C_4$-alkoxy-$C_1$–$C_4$-alkyl, cyano-$C_1$–$C_4$-alkyl, carboxyl-$C_1$–$C_4$-alkyl, ($C_1$–$C_4$-alkoxy) carbonyl-$C_1$–$C_4$-alkyl, $C_3$–$C_6$-cycloalkyl, $C_1$–$C_4$-alkoxy, ($C_3$–$C_6$-cycloalkoxy)carbonyl-$C_1$–$C_4$-alkyl, tetrahydrofuran-2-on-3-yl, phenyl, phenyl-$C_1$–$C_4$-alkyl, the phenyl ring being able in each case to be unsubstituted or to carry from one to three radicals selected from the group consisting of halogen, nitro, cyano, $C_1$–$C_4$-alkyl, $C_1$–$C_4$-alkoxy and $C_1$–$C_4$-haloalkyl, 5- or 6-membered heteroaryl or heteroaryl-$C_1$–$C_4$-alkyl, the heteroaromatic radical containing from one to three heteroatoms selected from a group consisting of one or two nitrogen atoms and able if desired to carry on each substitutable ring atom a radical selected from the group consisting of hydroxyl, halogen, $C_1$–$C_4$-alkyl, $C_1$–$C_4$-alkoxy and $C_1$–$C_4$-haloalkyl;
or $R^7$ and $R^8$ and/or $R^{30}$ and $R^{31}$ together are a tetramethylene, pentamethylene or ethyleneoxyethylene chain which may if desired carry from one to three $C_1$–$C_4$-alkyl radicals and/or a radical —$COOR^6$;

$R^9$ is hydrogen, $C_1$–$C_4$-alkyl, $C_1$–$C_4$-haloalkyl, $C_1$–$C_4$-alkoxy-$C_1$–$C_4$-alkyl, $C_3$–$C_7$-cycloalkyl which may in turn carry from one to three radicals selected from the group consisting of halogen, $C_1$–$C_4$-alkyl and $C_1$–$C_4$-alkoxy, phenyl or phenyl-$C_1$–$C_6$-alkyl in which the phenyl ring may in each case be unsubstituted or may carry from one to three radicals selected from the group consisting of halogen, nitro, $C_1$–$C_4$-alkyl, $C_1$–$C_4$-alkoxy and $C_1$–$C_4$-haloalkyl;

$R^{10}$ is hydrogen, $C_1$–$C_4$-alkyl, $C_3$–$C_6$-alkenyl, $C_3$–$C_6$-alkynyl, $C_1$–$C_4$-alkoxy-$C_1$–$C_4$-alkyl or the equivalent of an agriculturally usable cation;

$R^{11}$ and $R^{12}$ independently of one another are $C_1$–$C_4$-alkyl, $C_1$–$C_4$-haloalkyl, phenyl or thienyl, the phenyl or thienyl ring being able to be unsubstituted or to carry from one to three radicals selected from the group consisting of halogen, nitro, $C_1$–$C_4$-alkyl, $C_1$–$C_4$-alkoxy, $C_1$–$C_4$-alkylthio and $C_1$–$C_4$-haloalkyl, or 5- or 6-membered heteroaryl containing from one to three heteroatoms selected from the group consisting of 2 nitrogen atoms and one oxygen atom, the heteroaromatic radical being able to be unsubstituted or if desired to carry on each substitutable ring member a substituent in each case selected from the group consisting of hydroxyl, halogen, $C_1$–$C_4$-alkyl and $C_1$–$C_4$-alkoxy;

$R^{16}$ is hydrogen or $C_1$–$C_4$-alkyl;

$R^{17}$ is $C_1$–$C_4$-alkyl, $C_3$–$C_6$-cycloalkyl or phenyl;

$R^{18}$ is hydrogen or $C_1$–$C_4$-alkyl;

$R^{19}$ is hydrogen or $C_1$–$C_4$-alkyl;

$R^{20}$ is hydrogen, $C_1$–$C_4$-alkyl, $C_2$–$C_4$-alkenyl, $C_1$–$C_4$-haloalkyl, $C_1$–$C_4$-alkoxy-$C_1$–$C_4$-alkyl or di-($C_1$–$C_4$-alkoxy)-$C_1$–$C_4$alkyl;

$R^{21}$ and $R^{22}$ independently of one another are $C_1$–$C_4$-alkyl, $C_1$–$C_4$-haloalkyl or $C_1$–$C_4$-alkoxy-$C_1$–$C_4$-alkyl;

$R^{23}$, $R^{24}$, $R^{25}$, $R^{26}$, $R^{27}$, $R^{28}$ independently of one another are hydrogen, cyano, $C_1$–$C_4$-alkyl, $C_1$–$C_4$-alkoxy or —CO—O—$R^{20}$.

The organic molecular moieties indicated for the substituents $R^1$ to $R^{34}$ or as radicals on (hetero) aromatic structures represent—like the definition halogen—collective terms for individual enumerations of the specific group members. All carbon chains, that is all alkyl, alkylcarbonyl, haloalkylcarbonyl, alkenyl, alkynyl, haloalkyl, haloalkenyl, haloalkynyl, cyanoalkyl, phenylalkyl, carboxyalkyl, alkoxy, alkylthio, alkylcarbonyl, alkoxy-carbonyl and alkylsulfonyl moieties and the α- alkylalkylidene moiety, may be straight-chain or branched. Halogenated substituents preferably carry from one to five identical or different halogen atoms.

Specific examples are:
for halogen: fluorine, chlorine, bromine and iodine, preferably fluorine and chlorine;
for $C_1$–$C_6$-alkyl and the $C_1$–$C_6$-alkyl moieties of carboxy-$C_1$–$C_6$-alkyl, ($C_1$–$C_8$-alkoxy)carbonyl-$C_1$–$C_6$-alkyl, $C_1$–$C_4$-alkoxy-($C_1$–$C_4$-alkoxy)carbonyl-$C_1$–$C_6$-alkyl, ($C_1$–$C_8$-alkoxy)carbonyl-$C_1$–$C_6$-alkyl, $C_3$–$C_9$-(α-alkylalkylidene)iminooxy-$C_1$–$C_6$-alkyl, phenyl-$C_1$–$C_6$-alkyl, phenoxy-$C_1$–$C_6$-alkyl, heteroaryl-$C_1$–$C_6$-alkyl, phenyl-$C_1$–$C_6$-alkyl and heteroaryloxy-$C_1$–$C_6$-alkyl: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, preferably $C_1$–$C_4$-alkyl, especially methyl and ethyl; for $C_1$–$C_8$-alkyl and the alkyl moiety of cyano-$C_1$–$C_8$-alkyl: $C_1$–$C_6$-alkyl as mentioned above and, for example, n-heptyl and n-octyl, preferably $C_1$–$C_6$-alkyl, especially methyl and ethyl;

for $C_1$–$C_4$-alkyl and the alkyl moieties of $C_1$–$C_6$-alkoxy-$C_1$–$C_4$-alkyl, $C_1$–$C_4$-alkoxy-$C_1$–$C_4$-alkyl, di-($C_1$–$C_4$-alkoxy)-$C_1$–$C_4$-alkyl, $C_1$–$C_4$-alkylthio-$C_1$–$C_4$-alkyl, ($C_1$–$C_6$-alkoxy)carbonyl-$C_1$–$C_4$-alkyl, di-[($C_1$–$C_6$-alkoxy)carbonyl]-$C_1$–$C_4$-alkyl, ($C_1$–$C_4$-alkoxy)carbonyl-$C_1$–$C_4$-alkyl, ($C_3$–$C_6$-cycloalkoxy)carbonyl-$C_1$–$C_4$-alkyl, $C_1$–$C_4$-alkoxy-($C_1$–$C_4$-alkoxy)carbonyl-$C_1$–$C_4$-alkyl, $C_1$–$C_4$-alkylsulfonyl-$C_1$–$C_4$-alkyl, (1,3-dioxolan-2-yl)-$C_1$–$C_4$-alkyl, (1,3-dioxan-2-yl)-$C_1$–$C_4$-alkyl and heteroaryl-$C_1$–$C_4$-alkyl: methyl, ethyl, n-propyl, 1-methylethyl, n-butyl, 1-methylpropyl, 2-methylpropyl and 1,1-dimethylethyl, preferably methyl and ethyl;

for $C_1$–$C_3$-alkyl radicals: methyl, ethyl, n-propyl and 1-methylethyl, preferably methyl;

for $C_2$–$C_8$-alkenyl: $C_2$–$C_6$-alkenyl such as ethenyl, prop-1-en-1-yl, prop-2-en-1-yl, 1-methylethenyl, n-buten-1-yl, n-buten-2-yl, n-buten-3-yl, 1-methyl-prop-1-en-1-yl, 2-methyl-prop-1-en-1-yl, 1-methyl-prop-2-en-1-yl, 2-methyl-prop-2-en-1-yl, n-penten-1-yl, n-penten-2-yl, n-penten-3-yl, n-penten-4-yl, 1-methyl-but-1-en-1-yl, 2-methyl-but-1-en-1-yl, 3-methyl-but-1-en-1-yl, 1-methyl-but-2-en-1-yl, 2-methyl-but-2-en-1-yl, 3-methyl-but-2-en-1-yl, 1-methyl-but-3-en-1-yl, 2-methyl-but-3-en-1-yl, 3-methyl-but-3-en-1-yl, 1,1-dimethyl-prop-2-en-1-yl, 1,2-dimethyl-prop-1-en-1-yl, 1,2-dimethyl-prop-2-en-1-yl, 1-ethyl-prop-1-en-2-yl, 1-ethyl- prop-2-en-1-yl, n-hex-1-en-1-yl, n-hex-2-en-1-yl, n-hex-3-en-1-yl, n-hex-4-en-1-yl, n-hex-5-en-1-yl, 1-methyl- pent-1en-1-yl, 2-methyl-pent-1-en-1-yl, 3-methyl- pent-1-en-1-yl, 4-methyl-pent-1-en-1-yl, 1-methyl- pent-2-en-1-yl, 2-methyl-pent-2-en-1-yl, 3-methyl- pent-2-en-1-yl, 4-methyl-pent-2-en-1-yl, 1-methyl- pent-3-en-1-yl, 2-methyl-pent-3-en-1-yl, 3-methyl- pent-3-en-1-yl, 4-methyl-pent-3-en-1-yl, 1-methyl- pent-4-en-1-yl, 2-methyl-pent-4-en-1-yl, 3-methyl- pent-4-en-1-yl, 4-methyl-pent-4-en-1-yl, 1,1-dimethyl- but-2-en-1-yl, 1,1-dimethyl-but-3-en-1-yl, 1,2-dimethyl- but-1-en-1-yl, 1,2-dimethyl-but-2-en-1-yl, 1,2-dimethyl- but-3-en-1-yl, 1,3-dimethyl-but-1-en-1-yl, 1,3-dimethyl- but-2-en-1-yl, 1,3-dimethyl-but-3-en-1-yl, 2,2-dimethyl- but-3-en-1-yl, 2,3-dimethyl-but-1-en-1-yl, 2,3-dimethyl- but-2-en-1-yl, 2,3-dimethyl-but-3-en-1-yl, 3,3-dimethyl-but-1-en-1-yl, 3,3-dimethyl-but-2-en-1-yl, 1-ethyl-but-1-en-1-yl, 1-ethyl-but-2-en-1-yl, 1-ethyl-but-3-en-1-yl, 2-ethyl-but-1-en-1-yl, 2-ethyl-but-2-en--1-yl, 2-ethyl-but-3-en-1-yl, 1,1,2-trimethylprop-2-en-1-yl, 1-ethyl-1-methyl-prop-2-en-1-yl, 1-ethyl-2-methyl-prop-1-en-1-yl and 1-ethyl-2-methyl-prop-2-en-1-yl, and, for example, for n-hept-2-en-1-yl, hept-3-en-1-yl, n-oct-2-en-1-yl and oct-3-en-1-yl, preferably $C_2$–$C_6$-alkenyl;

for C₃–C₆-alkenyl and the alkenyl moiety of heteroaryl-C₃–C₆-alkenyl: prop-1-en-1-yl, prop-2-en-1-yl, 1-methylethenyl, n-buten-1-yl, n-buten-2-yl, n-buten-3-yl, 1-methyl-prop-1-en-1-yl, 2-methyl-prop-1-en-1-yl, 1-methyl-prop-2-en-1-yl, 2-methyl-prop-2-en-1-yl, n-penten-1-yl, n-penten-2-yl, n-penten-3-yl, n-penten-4-yl, 1-methyl-but-1-en-1-yl, 2-methyl-but-1-en-1-yl, 3-methyl-but-1-en-1-yl, 1-methyl-but-2-en-1-yl, 2-methyl-but-2-en-1-yl, 3-methyl-but-2-en-1-yl, 1-methyl-but-3-en-1-yl, 2-methyl-but-3-en-1-yl, 3-methyl-but-3-en-1-yl, 1,1-dimethyl-prop-2-en-1-yl, 1,2-dimethyl-prop-1-en-1-yl, 1,2-dimethyl-prop-2-en-1-yl, 1-ethyl-prop-1-en-2-yl, 1-ethyl-prop-2-en-1-yl, n-hex-1-en-1-yl, n-hex-2-en-1-yl, n-hex-3-en-1-yl, n-hex-4-en-1-yl, n-hex-5-en-1-yl, 1-methyl-pent-1-en-1-yl, 2-methyl-pent-1-en-1yl, 3-methyl-pent-1-en-1-yl, 4-methyl-pent-1-en-1-yl, 1-methyl-pent-2-en-1-yl, 2-methyl-pent-2-en-1-yl, 3methyl-pent-2-en-1-yl, 4-methyl-pent-2-en-1-yl, 1-methyl-pent-3-en-1-yl, 2-methyl-pent-3-en-1-yl, 3-methyl-pent-3-en-1-yl, 4-methyl-pent-3-en-1-yl, 1-methyl-pent-4-en-1-yl, 2-methyl-pent-4-en-1-yl, 3-methyl-pent-4-en-1-yl, 4-methyl-pent-4-en-1-yl, 1,1-dimethyl-but-2-en-1-yl, 1,1-dimethyl-but-3-en-1-yl, 1,2-dimethyl-but-1-en-1-yl, 1,2-dimethyl-but-2-en-1-yl, 1,2-dimethyl-but-3-en-1-yl, 1,3-dimethyl-but-1-en-1-yl, 1,3-dimethyl-but-2-en-1-yl, 1,3-dimethyl-but-3-en-1-yl, 2,2-dimethyl-but-3-en-1-yl, 2,3-dimethyl-but-1-en-1-yl, 2,3-dimethyl-but-2-en-1-yl, 2,3-dimethyl-but-3-en-1-yl, 3,3-dimethyl-but-1-en-1-yl, 3,3-dimethyl-but-2-en-1-yl, 1-ethyl-but-1-en-1-yl, 1-ethyl-but-2-en-1-yl, 1-ethyl-but-3-en-1-yl, 2-ethyl-but-1-en-1-yl, 2-ethyl-but-2-en-1-yl, 2-ethyl-but-3-en-1-yl, 1,1,2-trimethyl-prop-2-en-1-yl, 1-ethyl-1-methyl-prop-2-en-1-yl, 1-ethyl-2-methyl-prop-1-en-1-yl and 1-ethyl-2-methyl-prop-2-en-1-yl, preferably C₃- or C₄-alkenyl;

for C₂–C₈-alkynyl, for example: ethynyl, prop-1-yn-1-yl, prop-2-yn-3-yl, n-but-1-yn-1-yl, n-but-1-yn-4-yl, n-but-2-yn-1-yl, n-pent-1-yn-1-yl, n-pent-1yn-3-yl, n-pent-1-yn-4-yl, n-pent-1-yn-5-yl, n-pent-2-yn-1-yl, n-pent-2-yn-4-yl, n-pent-2-yn-5-yl, 3-methyl-but-1-yn-1-yl, 3-methyl-but-1-yn-3-yl, 3-methyl-but-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methyl-pent-1-yn-1-yl, 3-methyl-pent-1-yn-3-yl, 3-methyl-pent-1-yn-4-yl, 3-methyl-pent-1-yn-5-yl, 4-methyl-pent-1-yn-1-yl, 4-methyl-pent-2-yn-4-yl and 4-methyl-pent-2-yn-5-yl, preferably C₂–C₆-alkynyl, especially ethynyl and prop-2-yn-3-yl;

for C₃–C₆-alkynyl and the alkynyl moiety of heteroaryl-C₃–C₆-alkynyl: prop-1-yn-1-yl, prop-2-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methyl-but-1-yn-1-yl, 3-methyl-but-1-yn-3-yl, 3-methyl-but-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methyl-pent-1-yn-1-yl, 3-methyl-pent-1-yn-3-yl, 3-methyl-pent-1-yn-4-yl, 3-methyl-pent-1-yn-5-yl, 4-methyl-pent-1-yn-1-yl, 4-methyl-pent-2-yn-4-yl and 4-methyl-pent-2-yn-5-yl, preferably C₃- or C₄-alkynyl, especially ethynyl and prop-2-yn-3-yl;

for C₁–C₈-haloalkyl: C₁–C₈-alkyl as mentioned above which is partially or completely substituted by fluorine, chlorine and/or bromine, ie. eg. chloromethyl, dichloromethyl, trichloromethyl, fluromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloropropyl and hepta-fluoropropyl, preferably C₁–C₆-haloalkyl;

for C₁–C₆-haloalkyl: C₁–C₆-alkyl as mentioned above which is partially or completely substituted by fluorine, chlorine and/or bromine, ie. eg. chloromethyl, dichloromethyl, trichloromethyl, fluoromethyl, difluoromethyl, trifluoromethyl, chlorofluoromentyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloropropyl and hepta-fluoropropyl, preferably C₁–C₄-haloalkyl, especially trifluoromethyl and 1,2-dichloroethyl;

for C₁–C₄-haloalkyl: C₁–C₄-alkyl as mentioned above which is partially or completely substituted by fluorine, chlorine and/or bromine, ie. eg. chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2fluoroethyl, 2-chloro-2,2-difluoroethyl, 2,2-dichloro-2-fluoroethyl, 2,2,2-trichloroethyl, pentafluoroethyl, 3-chloropropyl and hepta-fluoropropyl, preferably trifluoromethyl and 1,2-dichloroethyl;

for C₂–C₈-haloalkenyl: C₂–C₈-alkenyl as mentioned above which is partially or completely substituted by fluorine, chlorine and/or bromine, ie. eg. 2-chloroallyl, 3-chloroallyl and 3,3-dichloroallyl, preferably C₂–C₆-haloalkenyl;

for C₃–C₆-haloalkenyl: C₃–C₆-alkenyl as mentioned above which is partially or completely substituted by fluorine, chlorine and/or bromine, ie. eg. 2-chloroallyl, 3-chloroallyl and 3,3-dichloroallyl;

for C₂–C₈-haloalkynyl: C₂–C₈-alkynyl as mentioned above which is partially or completely substituted by fluorine, chlorine and/or bromine, preferably C₂–C₆-haloalkynyl;

for cyano-C₁–C₄-alkyl: cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4cyanobut-1-yl, 1-cyanobut-2-yl, 2-cyanobut-2-yl, 1-cyanobut-3-yl, 2-cyanobut-3-yl, 1-cyano-2-methyl-prop-3-yl, 2-cyano-2-methyl-prop-3-yl, 3-cyano-2-methyl-prop-3-yl and 2-cyanomethyl-prop-2-yl, preferably 2-cyanoeth-1-yl;

for cyano-C₁–C₈-alkyl: cyano-C₁–C₄-alkyl as mentioned above, preferably 2-cyanoeth-1-yl; for phenyl-C₁–C₄-alkyl: benzyl, 2-phenyleth-1-yl, 2-phenyleth-1-yl, 1-phenylprop-1-yl, 2-phenylprop-1-yl, 3-phenylprop-1-yl, 1-phenylprop-2-yl, 2-phenylprop-2-yl, 1-phenylbut-1-yl, 2-phenylbut-1-yl, 3-phenylbut-1-yl, 4-phenylbut-1-yl, 1-phenylbut-2-yl, 2-phenylbut-2-yl, 1-phenylbut-3yl, 2-phenylbut-3-yl, 1-phenyl-2-methyl-prop-3-yl, 2-phenyl-2-methyl-prop-3-yl, 3-phenyl-2-methyl-prop-3-yl and 2-benzyl-prop-2-yl;

for carboxy-C₁–C₄-alkyl: carboxymethyl, 1-carboxyethyl, 2-carboxyethyl, 1-carboxyprop-1-yl, 2-carboxyprop-1-yl, 3-carboxyprop-1-yl, 1-carboxybut-1-yl, 2-carboxybut-1-yl, 3-carboxybut-1-yl, 4-carboxybut-1-yl, 1-carboxybut-2-yl, 2-carboxybut-2-yl, 3-carboxybut-2-yl, 3-carboxybut-2-yl, 4-carboxybut-2-yl, 1-(carboxymethyl)eth-1-yl, 1-(carboxymethyl)-1-(methyl)-eth-1-yl and 1-(carboxymethyl)-prop-1-yl, preferably carboxymethyl and 2-carboxyethyl;

for carboxy-$C_1$–$C_6$-alkyl: carboxy-$C_1$–$C_4$-alkyl as mentioned above, and 5-carboxypent-1-yl, preferably carboxy-$C_1$–$C_4$-alkyl;

for $C_1$–$C_4$-alkoxy and alkoxy moieties of $C_1$–$C_4$-alkoxy-$C_1$–$C_4$-alkyl, di-($C_1$–$C_4$-alkoxy)-$C_1$–$C_4$-alkyl, ($C_1$–$C_4$-alkoxy)carbonyl-$C_1$–$C_4$-alkyl, $C_1$–$C_4$-alkoxy-($C_1$–$C_4$-alkoxy)carbonyl-$C_1$–$C_6$-alkyl, $C_1$–$C_4$-alkoxy-($C_1$–$C_4$-alkoxy)carbonyl-$C_1$–$C_4$-alkyl and $C_1$–$C_4$-alkoxy-$C_1$–$C_4$-alkoxy: methoxy, ethoxy, n-propoxy, 1-methylethoxy, n-butoxy, 1-methylpropoxy, 2-methylpropoxy and 1,1-dimethylethoxy, preferably methoxy, ethoxy and 1-methylethoxy;

for $C_1$–$C_6$-alkoxy and the alkoxy moiety $C_1$–$C_6$-alkoxy-$C_1$–$C_6$-alkyl: $C_1$–$C_4$-alkoxy as mentioned above, and n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy, preferably methoxy, ethoxy and 1-methylethoxy;

for $C_1$–$C_8$-alkoxy: $C_1$–$C_6$-alkoxy as mentioned above and, for example, n-heptoxy and n-octoxy, preferably $C_1$–$C_6$-alkoxy, especially methoxy, ethoxy and 1-methylethoxy;

for $C_1$–$C_4$-alkylthio and the alkylthio moiety of $C_1$–$C_4$-alkylthio-$C_1$–$C_4$-alkyl: methylthio, ethylthio, n-propylthio, 1-methylethylthio, n-butylthio, 1-methylpropylthio, 2-methylpropylthio and 1,1-dimethylethylthio, preferably methylthio, ethylthio and 1methylethylthio;

for $C_1$–$C_6$-alkylthio: $C_1$–$C_4$-alkylthio as mentioned above and n-pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, n-hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio, preferably methylthio, ethylthio and 1-methylethylthio;

for ($C_1$–$C_4$-alkyl)carbonyl: methylcarbonyl, ethylcarbonyl, n-propylcarbonyl, 1-methylethylcarbonyl, n-butylcarbonyl, 1-methylpropylcarbonyl, 2-methylpropylcarbonyl and 1,1-dimethylethylcarbonyl, preferably methylcarbonyl, ethylcarbonyl and n-propylcarbonyl;

for ($C_1$–$C_4$-haloalkyl)carbonyl: $C_1$–$C_4$-alkylcarbonyl as mentioned above which is partially or completely substituted by fluorine, chlorine and/or bromine, ie. eg. chloromethylcarbonyl, dichloromethylcarbonyl, trichloromethylcarbonyl, fluoromethylcarbonyl, difluoromethylcarbonyl, trifluoromethylcarbonyl, chlorofluoromethylcarbonyl, dichlorofluoromethylcarbonyl, chlorodifluoromethylcarbonyl, 1-fluoroethylcarbonyl, 2-fluoroethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2,2,2-trichloroethylcarbonyl, pentafluoroethylcarbonyl, 3-chloropropylcarbonyl and heptafluoropropylcarbonyl, preferably trifluoromethylcarbonyl and 1,2-dichloroethylcarbonyl;

for ($C_1$–$C_6$-alkoxy carbonyl and the alkoxycarbonyl moieties of ($C_1$–$C_6$-alkoxy)carbonyl-$C_1$–$C_4$-alkyl and di-[($C_1$–$C_6$-alkoxy)-carbonyl]-$C_1$–$C_4$-alkyl: methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl, 1,1-dimethylethoxycarbonyl, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,2-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl and 1-ethyl-2-methylpropoxycarbonyl, preferably ($C_1$–$C_4$-alkoxy)carbonyl, especially methoxycarbonyl, ethoxycarbonyl and 1-methylethoxycarbonyl;

for the alkoxycarbonyl moiety of ($C_1$–$C_8$-alkoxy)carbonyl-$C_1$–$C_6$-alkyl: ($C_1$–$C_6$-alkoxy)carbonyl as mentioned above and, for example, n-heptoxycarbonyl and n-octoxycarbonyl, preferably ($C_1$–$C_6$-alkoxy)carbonyl, especially methoxycarbonyl, ethoxycarbonyl and 1-methylethoxycarbonyl;

for the alkylsulfonyl moiety of $C_1$–$C_4$-alkylsulfonyl-$C_1$–$C_4$-alkyl: methylsulfonyl, ethylsulfonyl, n-propylsulfonyl, 1-methylethylsulfonyl, n-butylsulfonyl, 1-methylpropylsulfonyl, 2-methylpropylsulfonyl and 1,1-dimethylethylsulfonyl, preferably methylsulfonyl and ethylsulfonyl;

for the $C_3$–$C_9$-(α-alkylalkylidene) moiety of $C_3$–$C_9$-(α-alkylalkylidene)iminooxy-$C_1$–$C_6$-alkyl, for example: α-methylethylidene, α-methylpropylidene and α-ethyl-propylidene, especially αmethylethylidene;

for $C_3$–$C_6$-cycloalkyl: cyclopropyl, cyclobutyl, cyclopentyl and cyclohexyl, preferably cyclopropyl and cyclopentyl;

for $C_3$–$C_7$-cycloalkyl: $C_3$–$C_6$-cycloalkyl as mentioned above and cycloheptyl, preferably cyclopropyl and cyclopentyl;

for $C_3$–$C_8$-cycloalkyl: $C_3$–$C_6$-cycloalkyl as mentioned above and cycloheptyl and cyclooctyl, preferably cyclopropyl, cyclopentyl and cyclohexyl;

13 for $C_5$–$C_7$-cycloalkenyl: cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl and cyclohept-4-enyl, preferably cyclopent-1-enyl;

for the cycloalkoxycarbonyl moiety of ($C_3$–$C_6$-cycloalkoxy)carbonyl-$C_1$–$C_4$-alkyl: cyclopropoxycarbonyl, cyclobutoxycarbonyl, cyclopentoxycarbonyl and cyclohexoxycarbonyl, preferably cyclopropoxycarbonyl and cyclopentoxycarbonyl;

5- or 6-membered heteroaryl and the heteroaryl moiety of heteroaryl-$C_1$–$C_4$-alkyl: for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,3-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl, preferably 3-pyrazolyl, 2-pyridyl and 2-thienyl.

Particularly suitable agriculturally usable cations are those cations which do not have an adverse effect on the herbicidal activity of the compounds I, especially the ions of alkali metals, preferably sodium and potassium, of alkaline earth metals, preferably calcium, magnesium and barium, and of transition metals, preferably manganese, copper, zinc and iron, and the ammonium ion, which may if desired carry from one to three $C_1$–$C_4$-alkyl or hydroxy-$C_1$–$C_4$-alkyl substituents and/or a phenyl or benzyl substituent, preferably diisopropylammonium, tetramethylammonium, tetrabutylammonium, trimethylbenzylammonium and trimethyl-(2-hydroxyethyl)-ammonium, and also phosphonium ions, sulfonium ions, preferably tri-($C_1$–$C_4$-alkyl)sulfonium, and sulfoxonium ions, preferably tri-($C_1$–$C_4$-alkyl)sulfoxonium.

The 3-phenylpyrazole derivatives of the formula I can be obtained in a number of ways, preferably by one of the following processes:

A) Reaction of a β-ketocarboxylic acid derivative III with hydrazine or a hydrazine derivate in an inert solvent (cf. eg. JP-A 04/225 937 and JP-A 03/072 460) and alkylation of the product IV:

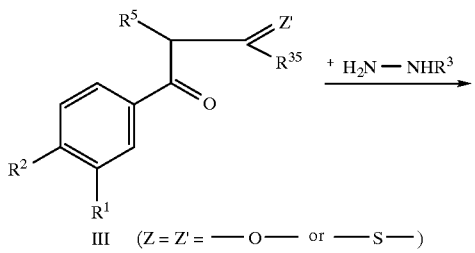

III    (Z = Z' = —O— or —S—)

14

-continued

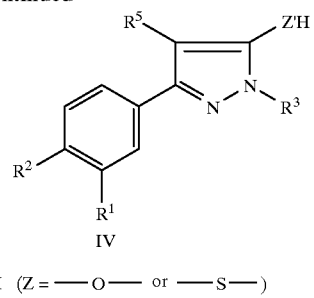

IV

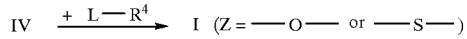

IV    I (Z = —O— or —S—)

L is a suitable leaving group such as halogen, —O-$SO_2CH_3$, —O—$SO_2CF_3$, —O—$SO_2C_4F_9$ or —O—$SO_2$(p—$CH_3$—$C_6H_4$);

$R^{35}$ is preferably $C_1$–$C_4$-alkoxy, $C_1$–$C_4$-alkylcarbonyloxy or halogen.

The solvent may be aprotic or protic. Examples of suitable solvents are organic acids such as acetic acid, hydrocarbons, halogenated hydrocarbons, ethers such as ethylene glycol dimethyl ether, alcohols such as methanol and ethanol, and sulfoxides.

The reaction temperature is determined primarily by the melting point of the compound III and the boiling point of the reaction mixture. It is preferably from about 60 to 120° C.

Generally from 0.95 to 5 times the molar quantity, advantageously from 1 to 1.4 times the quantity, of hydrazine or hydrazine derivative is employed, based on the β-ketocarboxylic acid derivative III.

The quantity of alkylating agent L-$R^4$ is commonly likewise from 0.95 to 5 times the molar quantity, based on the intermediate IV.

In view of the preferred radicals $R^3$ on the 3-phenylpyrazoles I, particular preference is given to those hydrazine derivatives which carry an alkyl group.

Alkylation is normally carried out with the halide, preferably the chloride or bromide, or with the sulfate of an alkane or haloalkane, if desired in the presence of an organic base, for example a trialkylamine or pyridine, or an inorganic base, for example an alkali metal carbonate.

The alkylation is advantageously carried out in an inert organic solvent, for example in an aliphatic or cyclic ether such as 1,2-dimethoxyethane, tetrahydrofuran or dioxane, in an aliphatic ketone such as acetone, in an amide such as dimethylformamide, in a sulfoxide such as dimethyl sulfoxide, or in a mixture of one of these solvents and water.

The reaction can generally be carried out at from 0° C. to the boiling temperature of the reaction mixture. It is preferably carried out from about 20 to 80° C.

When z=s the product can be oxidized to the sulfoxide or sulfone in a manner known per se (cf. eg. Houben-Weyl, Methoden der Organischen Chemie [Methods of Organic Chemistry], Vol. 9, Georg Thieme Verlag, Stuttgart, 4th Edition 1955, p. 211ff and 227ff; Org. Synth. Col. Vol. V, 791):

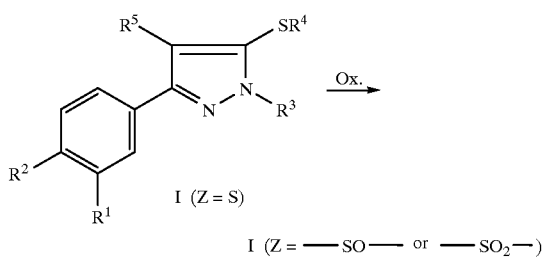

B) Halogenation of compounds I where $R^5$=hydrogen:

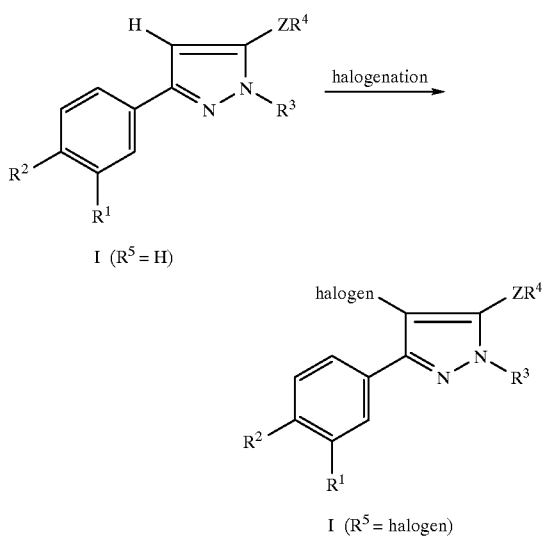

The reaction can be carried out in an inert solvent or diluent or without solvent.

Examples of suitable solvents are organic acids, inorganic acids, hydrocarbons, halogenated hydrocarbons, aromatic hydrocarbons, ethers, sulfides, sulfoxides and sulfones.

Examples of suitable halogenating agents are chlorine, bromine, N-bromosuccinimide, N-chlorosuccinimide or sulfuryl chloride. Depending on the starting compounds and halogenating agent, the addition of a free-radical initiator, for example an organic peroxide such as dibenzoyl peroxide or an azo compound such as azobisisobutyronitrile, or irradiation with light, may have an advantageous effect on the course of the reaction.

The quantity of halogenating agent is not critical. Both sub-stoichiometric amounts and large excesses of halogenating agent, based on the compound I where $R^5$=hydrogen which is to be halogenated, are possible.

If a free-radical initiator is used it is generally adequate to employ a catalytic amount.

The reaction temperature is normally from −100 to 200° C., ideally at from 10 to 100° C., or at the boiling point of the reaction mixture.

C) Nitration of compounds I where $R^1$=hydrogen:

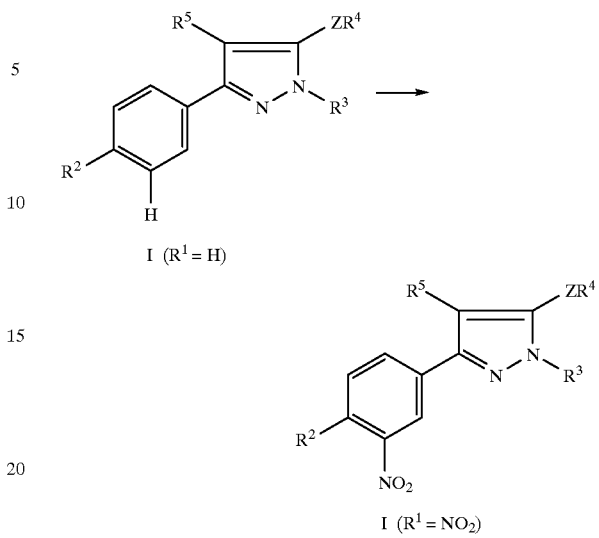

Examples of suitable nitrating reagents are nitric acid in various concentrations, including concentrated and fuming nitric acid, mixtures of sulfuric acid and nitric acid, acetyl nitrates and alkyl nitrates.

The reaction can either be carried out without solvent in an excess of the nitrating reagent or in an inert solvent or diluent, suitable examples being water, inorganic acids, organic acids, chlorinated hydrocarbons such as methylene chloride, anhydrides such as acetic anhydride, and mixtures of these solvents.

The starting compound I where $R^1$=H and the nitrating reagent are advantageously employed in approximately equimolar quantities; in order to optimize the conversion of the compound to be nitrated, however, it may be advantageous to use the nitrating reagent in excess, up to about 10 times the molar quantity. When the reaction is carried out without solvent in the nitrating reagent, the latter is present in an even greater excess.

The reaction temperature is normally from -31 100 to 200° C., preferably from −30 to 50° C.

The reaction mixture can be worked up in a known manner, for example by diluting the reaction solution with water and then isolating the product by filtration, crystallization or solvent extraction.

D) Reduction of compounds I where $R^1$=nitro:

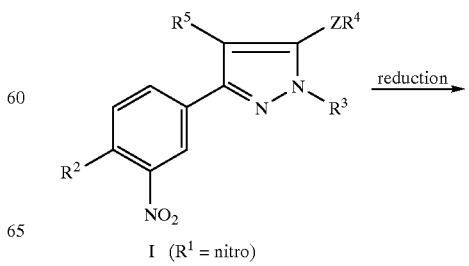

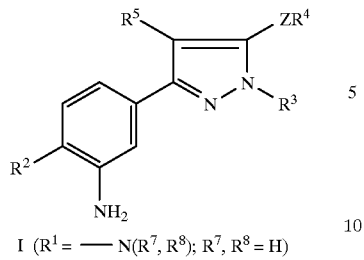

I (R¹ = —N(R⁷, R⁸); R⁷, R⁸ = H)

D1) Reduction with a metal such as iron, zinc or tin under acid reaction conditions or by means of complex hydrides such as lithium aluminium hydride and sodium borohydride:

The solvent, for example water, an alcohol such as methanol, ethanol or isopropanol or an ether such as diethyl ether, methyl tert-butyl ether, dioxane, tetrahydrofuran and ethylene glycol dimethyl ether, is dependent on the chosen reducing agent.

Reduction with a metal is preferably carried out without solvent in an inorganic acid, especially concentrated or dilute hydrochloric acid, or in an organic acid such as acetic acid. However, it is also possible to mix in with the acid an inert solvent as mentioned above.

The starting compound I (R¹=NO₂) and the reducing agent are advantageously employed in approximately equimolar quantities; in order to optimize the course of the reaction, however, it may be advantageous to use one of the two components in excess, up to about 10 times the molar quantity.

The quantity of acid is not critical. In order to maximize reduction of the starting compound it is advantageous to use at least an equivalent quantity of acid.

The reaction temperature is generally from −30 to 200° C., preferably 0 to 80° C.

After the end of the reaction the reaction mixture is normally diluted with water and the product is isolated by filtration, crystallization or extraction with a solvent which is substantially immiscible with water, for example with ethyl acetate, diethyl ether or methylene chloride. If desired, the product can subsequently be purified in the known manner.

D2) Catalytic hydrogenation with hydrogen:

Examples of suitable catalysts are Raney nickel, palladium on charcoal, palladium oxide, platinum and platinum oxide, a sufficient quantity of catalyst generally being from 0.05 to 10.0 mol%, based on the compound to be reduced.

The reaction is carried out either without solvent or in an inert solvent or diluent, for example in acetic acid, a mixture of acetic acid and water, ethyl acetate, ethanol or toluene.

After the catalyst has been separated off the reaction solution can be worked up to the product in a conventional manner.

Hydrogenation can be carried out at atmospheric pressure or superatmospheric pressure.

E) Compounds I in which R¹ is −N(R⁷,R⁸) and R⁷ and R⁸ are hydrogen can, for example, be alkylated, acylated, sulfonylated, hydroxylated or diazotized in a known manner (in this respect see Houben-Weyl, Methoden der Organischen Chemie [Methods of Organic Chemistry], Volume E16d, part 2, Georg Thieme Verlag, Stuttgart, 4th Edition 1992, pages 1241 to 1314 and the literature cited therein):

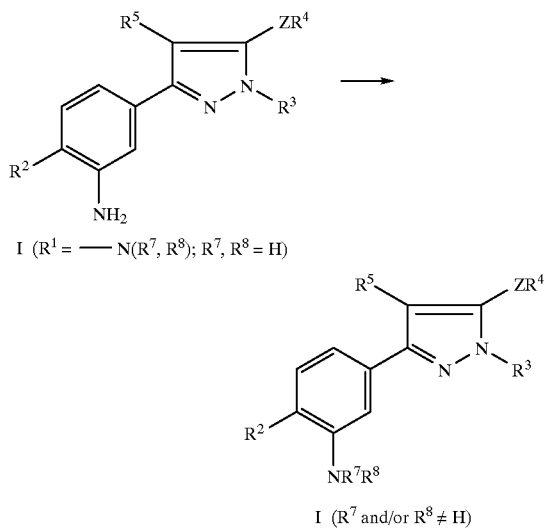

I (R¹ = —N(R⁷, R⁸); R⁷, R⁸ = H)

I (R⁷ and/or R⁸ ≠ H)

Further reactions are possible subsequently, for example Sandmeyer reactions {cf. eg. H. H. Hodgson, Chem. Rev. 40, (1947) 251 and Houben-Weyl, Methoden der Organischen Chemie [Methods of Organic Chemistry], Vol. 5/4, Georg Thieme Verlag, Stuttgart, 4th Edition 1960, p. 438}, Meerwein reactions {see eg. M. Doyle, B. Siegfried. R. C. Elliot, J. F. Dellaria, J. Org. Chem. 42, (1977) 2431}, boiling with phenol (see eg. Org. Synth. Coll. Vol. 3, (1955) 130} or the reduction of the diazonium salt of I (R¹=NH₂) to the corresponding arylhydrazine (see eg. Houben-Weyl, Methoden der Organischen Chemie [Methods of Organic Chemistry], Vol. E16a, Georg Thieme Verlag, Stuttgart, 4th Edition 1990, p. 656ff.). The arylhydrazines may in turn be acylated in a conventional manner (cf. in this respect eg. Houben-Weyl, Methoden der Organischen Chemie [Methods of Organic Chemistry], Vol. E16a, Georg Thieme Verlag, Stuttgart, 4th Edition 1990, p. 828ff.).

The acylhydrazines obtained in this way can in turn be oxidized to azo compounds (see eg. Houben-Weyl, Methoden der Organischen Chemie, Vol. E16d, Georg Thieme Verlag, Stuttgart, 4th Edition 1992, p. 102f.).

F) Halogenation of compounds I in which $R^1$ is methyl:

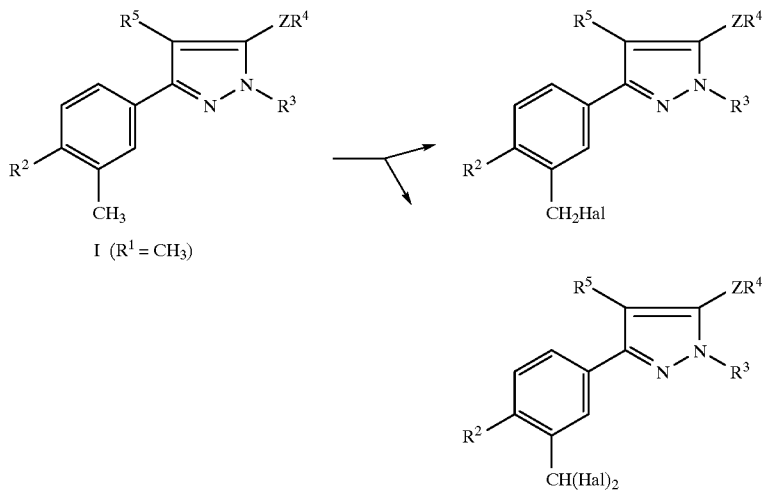

Hal = halogen, preferably chlorine or bromine.

With regard to solvents, proportions and the reaction temperature, reference is made to the comments under method B).

G) Nucleophilic substitution of a halogen atom in compounds I where $R^1$=$CH_2Hal$:

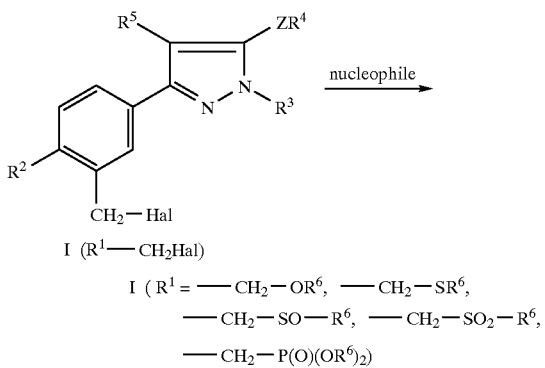

Examples of suitable nucleophiles are alkoxides, thioalkoxides, aryl or alkyl anions, amines, cyanides, alcohols, thiols or salts of carboxylic acids or trialkyl phosphites; use of the latter gives rise to phosphonates ($R^1$=—$CH_2$—$P(O)(OR^6)_2$; Arbuzov reaction; see eg. A. R. Katritzky, B. Pilarski, Org. Prep. Proced. Int. 22 (1990) 209).

Depending on the starting compound and nucleophile, it may be advantageous to add a base, for example an organic base such as a trialkylamine or diazobicycloundecene or an inorganic base such as potassium carbonate or sodium carbonate or an alkali metal hydroxide.

The quantity of base is preferably from 0.95 to 10 mol, in particular from about 1 to 3 mol, per mole of starting compound.

Particularly preferred solvents are dimethylformamide, dimethylacetamide, acetone, dimethyl sulfoxide, dioxane, water and a mixture of these solvents.

A further possibility is to carry out the reaction in a 2-phase system comprising water and an organic solvent which is substantially immiscible with water, for example methylene chloride. In this variant, in order to improve the course of the reaction it is advantageous to add a phase transfer catalyst, for example an ammonium salt such as benzyltrialkylammonium halide and tetrabutylammonium halide (with regard to phase transfer catalysis, see also Synthesis 1976, 113).

It is generally adequate to employ a catalytic quantity of phase transfer catalyst, for instance between 1 and 10 mol %, based on the starting compound.

The reaction temperature depends on the choice of nucleophile. When aryl or alkyl anions are used, this temperature is from about –150 to 0° C., preferably from –78 to –20° C. For the other nucleophiles mentioned above, it is usually necessary to employ a higher reaction temperature, for instance from 0 to 100° C.

Those end products I in which $R^1$ is —$CH_2$—$OR^6$ where $R^6$=($C_1$–$C_4$-alkyl)carbonyl, can be hydrolyzed subsequently in a manner known per se to give compounds I where $R^1$=—$CH_2OH$. The hydrolyzed products can then if desired be alkylated, acylated or sulfonated, to give further compounds within the definition for I where $R^1$=—$CH_2OR^6$ ($R^6 \neq H$) (see eg. Houben-Weyl, Methoden der Organischen Chemie [Methods of Organic Chemistry], Georg Thieme Verlag, Stuttgart: Vol. 6/1a, 4th Edition 1979, p. 262ff.; Vol. 8, 4th Edition 1952; p. 516ff.; Vol. 6/3, 4th Edition 1965, p. 10ff.; Vol. 9, 4th Edition 1955, p. 343ff. and 659ff.).

H) Acid hydrolysis of compounds I in which $R^1$ is dihalomethyl:

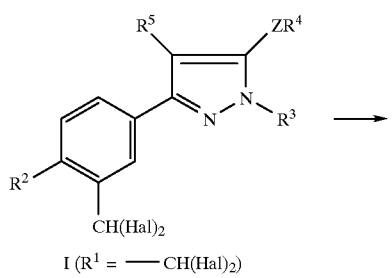

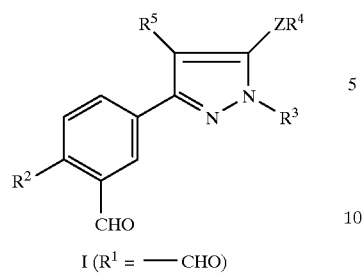

I (R¹ = ─CHO)

The hydrolysis is preferably carried out without solvent in an acid such as hydrochloric acid, sulfuric acid or acetic acid, specially concentrated sulfuric acid, or in a mixture of acetic acid and water (eg. 3:1).

The reaction temperature is usually from 0 to 120° C.

The reaction product can generally be worked up in a manner known per se.

I) Oxidation of compounds I in which R¹ is halomethyl in a manner known per se, eg. according to Kornblum (in this respect see in particular pages 179 to 181 of "Methods for the Oxidation of Organic Compounds" by Alan H. Haines, Academic Press 1988, in the series "Best Synthetic Methods"):

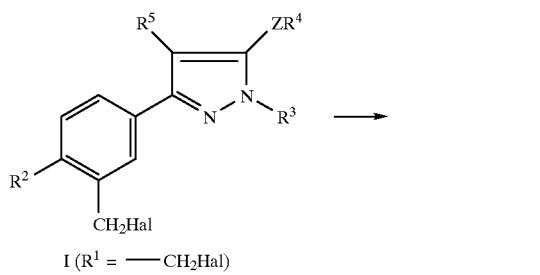

I (R¹ = ─CH₂Hal)

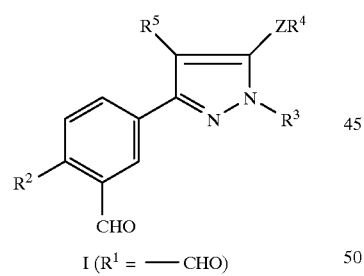

I (R¹ = ─CHO)

Dimethyl sulfoxide is one example of a suitable solvent.

K) Oxidation of compounds I in which R¹ is formyl:

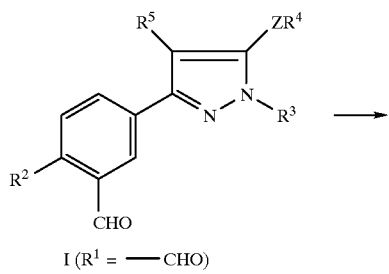

I (R¹ = ─CHO)

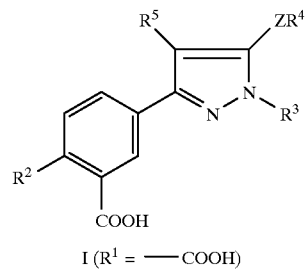

I (R¹ = ─COOH)

Examples of suitable inert solvents are water, hydrocarbons, aromatic hydrocarbons or pyridine and derivatives thereof.

Examples of suitable oxidizing agents are potassium permanganate, potassium dichromate, sodium perborate, sodium chlorite, hydrogen peroxide and oxygen.

The reaction temperature depends in particular on the reaction medium. It is preferably from 0 to 120° C.

Working up to give the product is carried out in the conventional manner.

The further reaction of the product to give the corresponding acid derivatives or ketone derivatives may take place in a manner known per se (see in this respect in particular parts 1 and 2 of Volume E5 of Houben-Weyl, Methoden der organischen Chemie [Methods of Organic Chemistry]).

L) Halosulfonation of compounds I in which R¹ is ─SO₂─Cl:

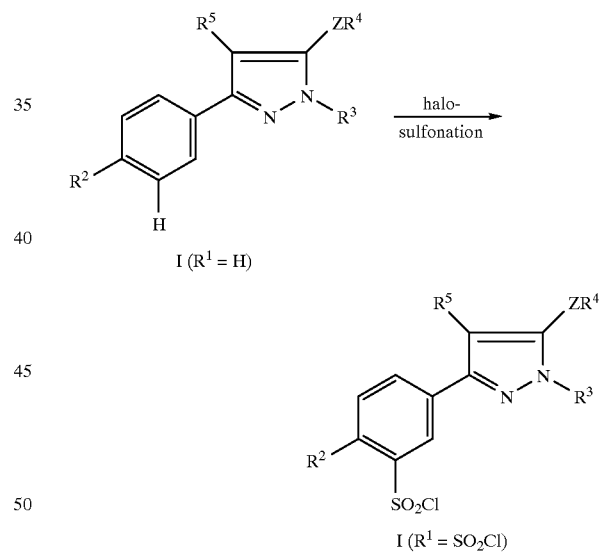

The halosulfonation can be carried out without solvent in an excess of sulfonating reagent or in an inert solvent, for example in a halogenated hydrocarbon, an ether, an alkanenitrile or a mineral acid.

Chlorosulfonic acid is both the preferred reagent and solvent.

The sulfonating reagent is normally employed in a slightly sub-stoichiometric quantity (up to about 95 mol %) or in an excess of from 1 to 5 times the molar quantity, based on the starting compound I (R¹=H). If the reaction is carried out without inert solvent then an even greater excess may be advantageous.

The reaction temperature is normally between 0° C. and the boiling point of the reaction mixture.

For working up the product, water for example is added to the reaction mixture, after which the product can be isolated in a conventional manner.

M) Reaction of compounds I in which $R^1$ is —$SO_2$—Cl with carbon, oxygen or nitrogen nucleophiles to give the corresponding sulfonic acids, sulfonates or sulfonamide derivates in a manner known per se (see in this respect in particular page 351 of "The Chemistry of Sulphonic Acids, Esters and their Derivatives", John Wiley & Sons 1991, in the series "The Chemistry of Functional Groups" and p. 530f. in Houben-Weyl, Methoden der Organischen Chemie [Methods of Organic Chemistry], Vol. 9, Georg Thieme Verlag, Stuttgart, 4th Edition 1995):

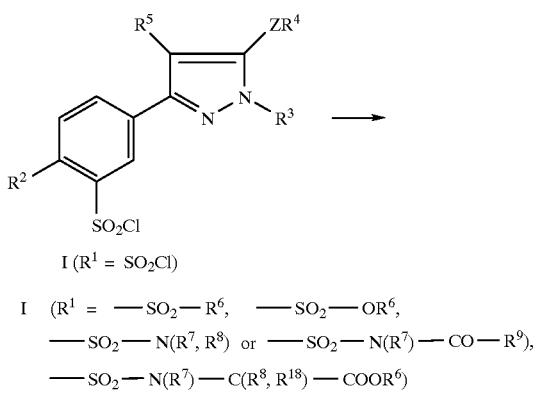

N) Reduction of compounds I in which $R^1$ is —$SO_2$—Cl to give the corresponding thiols in a manner known per se (see in this respect, in particular, page 216 of "The Chemistry of the Thiol Group", John Wiley & Sons 1974, in the series "The Chemistry of Functional Groups"):

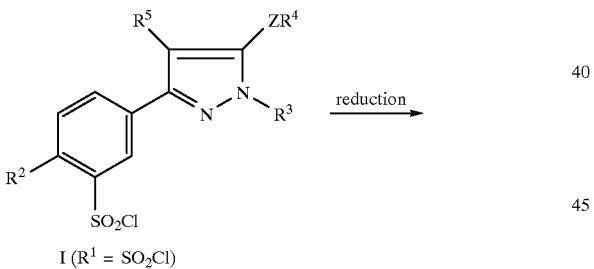

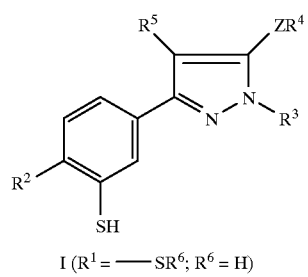

Examples of suitable reducing agents are transition metals such as iron, zinc and tin.

The compounds I in which $R^1$ is the thiol group can be converted in a manner known per se (cf. eg. p. 721 of "The Chemistry of Sulphonic Acids, Esters and their Derivatives", John Wiley & Sons 1991, in the series "The Chemistry of Functional Groups") to compounds of the formula I in which $R^1$ is —$SR^6$ ($R^6 \neq$ hydrogen). The group —$SR^6$ may in turn be oxidized in a manner known per se {in this context see the details under method A)} to —SO—$R^6$ and —$SO_2$—$R^6$.

O) Conversion of compounds I in which $R^1$ is formyl, in a manner known per se, to the corresponding oximes (see eg. Houben-Weyl, Methoden der Organischen Chemie [Methods of Organic Chemistry], Vol. 10/4, Georg Thieme Verlag, Stuttgart, 4th Edition 1968, p. 55ff. and p. 73ff.), acetals (see in this respect eg. Houben-Weyl, Methoden der Organischen Chemie [Methods of Organic Chemistry], Vol. 6/3, Georg Thieme Verlag, Stuttgart, 4th Edition 1965, p. 221ff. and p. 250ff.) or alkenes (cf. eg. Houben-Weyl, Methoden der Organischen Chemie [Methods of Organic Chemistry], Vol. 5/16, Georg Thieme Verlag, Stuttgart, 4th Edition 1972, p. 383ff.):

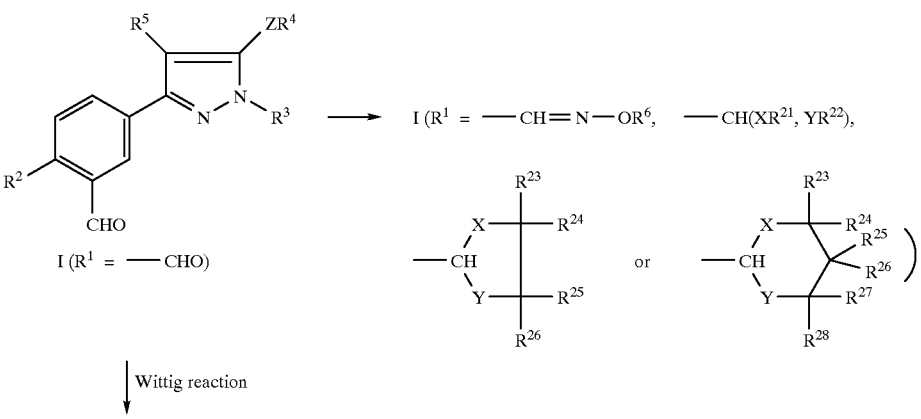

-continued

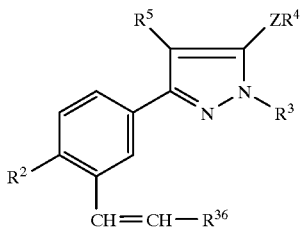

I  ($R^1$ = —CH=CH—$R^{36}$;  $R^{36}$ = —CO—$OR^6$,  —P(O)($OR^6$)$_2$,  —CO—O—N=C($R^{14}$, $R^{15}$),

—CO—O—$CH_2$—O—N=C($R^{16}$, $R^{17}$),  —CO—O—C($R^{18}$, $R^{19}$)—$CH_2$—O—N=C($R^{16}$, $R^{17}$),

—CO—N($R^7$, $R^8$),  —CS—N($R^7$, $R^8$),  —CO—NH—$SO_2$—($C_1$-$C_4$-alkyl),  —CO—$R^{20}$,

—CH=N—$OR^6$,  —CH($XR^{21}$, $YR^{22}$),  —C($R^{20}$)=N—O—$R^6$,

—CO—N($R^7$)—C($R^8$, $R^{18}$)—$COOR^6$,

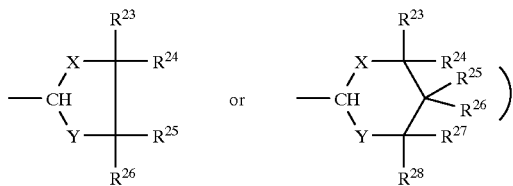

P) Nucleophilic cyanide substitution of compounds I where $R^1$=$NO_2$ and $R^2$=F:

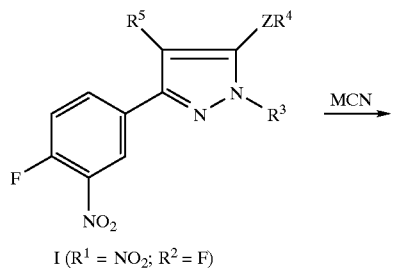

I ($R^1$ = $NO_2$; $R^2$ = F)

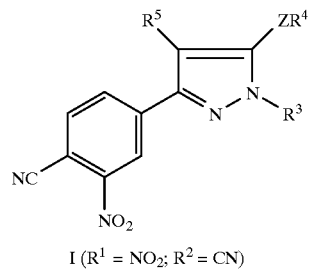

I ($R^1$ = $NO_2$; $R^2$ = CN)

M is a metallic or organic cation, preferably an alkali metal or tetraalkylammonium ion.

The reaction is normally carried out in a polar aprotic solvent such as dimethyl sulfoxide, N,N-dimethylformamide and sulfolane, the reaction temperature lying between its melting and boiling points, in particular at from 0 to 100° C.

It is preferred to employ a slight molar excess of the cyanide MCN. In order to optimize the conversion, however, it may be advantageous to use a large excess of MCN, for instance up to five times the molar quantity, based on the quantity of starting compound I where $R^2$=fluorine.

The reaction mixture can be worked up in a manner known per se, for example by diluting the reaction mixture with water and then isolating the product by filtration, crystallization or solvent extraction.

Q) Nucleophilic alcoholate substitution of compounds I where $R^1$=$NO_2$ and $R^2$=CN in a manner known per se (see eg. Houben-Weyl, Methoden der Organischen Chemie [Methods of Organic Chemistry], Vol. 6/3, Georg Thieme Verlag, Stuttgart, 4th Edition 1965, p. 75ff.); compounds I where $R^1$=$OR^6$, $R^2$=CN and $R^6$=lower alkyl can preferably be prepared in this manner:

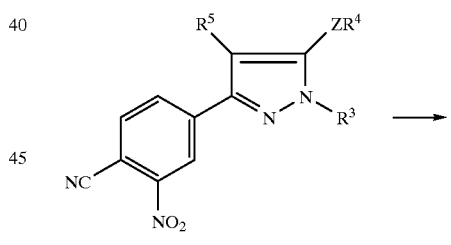

I ($R^1$ = $NO_2$; $R^2$ = CN)

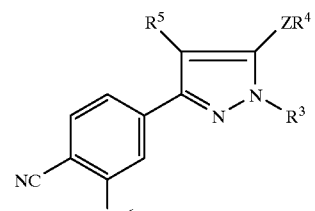

I ($R^1$ = $OR^6$,
$R^2$ = CN,
$R^6$ is preferably lower alkyl)

The product I ($R^1$=$OR^6$, $R^2$=CN) may if desired be cleaved in a manner known per se to give compounds I where $R^1$=OH ($R^2$=CN) (cf. eg. Houben-Weyl, Methoden der Organischen Chemie [Methods of Organic Chemistry], Vol. 6/1c, Georg Thieme Verlag Stuttgart, 4th Edition 1976, p. 313ff.).

Compounds I where $R^1$=hydroxyl, which are accessible in this manner or by means of the phenol boiling method described under E), may if desired be alkylated, acylated or sulfonated in a manner known per se, as described under G) for compounds I where $R^1$=—$CH_2OH$.

Unless otherwise indicated, the reactions described above are advantageously carried out at atmospheric pressure or under the autogenous pressure of the particular reaction mixture.

The preparation of the substituted 3-phenylpyrazoles I may produce isomer mixtures which, however, may if desired be separated into the pure isomers by the methods which are conventional for this purpose, such as crystallization or chromatography, possibly on an optically active adsorbate. Pure optically active isomers can advantageously be prepared from corresponding optically active starting compounds.

Substituted 3-phenylpyrazoles I in which $R^{10}$ is an alkali metal can be obtained by treating compounds I where $R^{10}$=hydrogen, for example with sodium hydroxide or potassium hydroxide in aqueous solution or in an organic solvent such as methanol, ethanol, acetone or toluene, or with sodium hydride in an organic solvent such as dimethylformamide.

Substituted 3-phenylpyrazoles I in which $R^{10}$ is an agriculturally usable cation other than an alkali metal may be prepared conventionally by salt exchange of the corresponding compound I where $R^{10}$=an alkali metal ion.

Compounds I in which $R^{10}$ is, for example, manganese, copper, zinc, iron, calcium, magnesium or barium ion may be prepared in a conventional manner from compounds I where $R^{10}$=sodium, and from compounds I where $R^{10}$= ammonium or phosphonium ion, using ammonia, phosphonium hydroxides, sulfonium hydroxides or sulfoxonium hydroxides.

Using the process described it is also possible to obtain all other salts of agriculturally usable cations of the compounds I, for example those derived from compounds I ($R^1$=— $SO_2$—$OR^6$; $R^6$=H), ($R^1$=—$SO_2$—$N(R^7)$—CO—$R^9$; $R^7$=H), ($R^1$=—$N(R^{10})$—$SO_2$—$R^{11}$; $R^{10}$=H), ($R^1$=— A—CO—NH—$SO_2$—($C_1$-$C_4$-alkyl)) or ($R^1$=—A—P(O) $(OR^6)_2$, $R^6$=H).

Those compounds I which carry a basic functional group, for example if $R^1$ is —$N(R^7,R^8)$, —$N(R^7)$—$N(R^8,R^{32})$, —N=N—$COR^9$ or —$N(R^7)$—$N(R^8)$—CO—$R^9$, and those compounds I containing the functional group >C=N—, can be converted into their acid addition salts by reaction with the corresponding acid.

The acid addition can be carried out in aqueous solution or in an organic solvent such as methanol, ethanol, acetone, toluene or ether. The acid addition salts of I may also be subjected to salt exchange, making it possible to obtain agriculturally usable salts with other anions.

The salt formation reactions normally proceed at a sufficient rate even at about 20° C.

The salts can be isolated by, for example, precipitation with an appropriate inert solvent or by evaporating off the solvent.

The substituted 3-phenylpyraxoles I and salts thereof are suitable, both as isomer mixtures and in the form of the pure isomers, as herbicides. They are able to give very good control of broad-leaved weeds and grass weeds in crops such as wheat, rice, maize, soybean and cotton without noticeably damaging the crop plants. This effect occurs especially at low application rates.

Depending on the particular application method, the compounds I or herbicidal compositions containing them can also be employed in a further range of crop plants for the elimination of unwanted plants. Examples of suitable crops are the following:

*Allium cepa, Ananas comosus, Arachis hypogaea, Asparagus officinalis, Beta vulgaris* ssp. *altissima, Beta vulgaris* ssp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis quineensis, Fragaria vesca, Glycine max, Gossypium hirsutum,* (*Gossypium arboreum, Gossypium herbaceum, Gossypium vitifolium*), *Helianthus annuus, Bevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum* (*N. rustica*), *Olea europaea, Oryza sativa, Phasedolus lunatus, Phaseolus vulgaris, Picea abies, Pinus* spp., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera* and *Zea mays.*

Moreover, the compounds I can also be employed in crops which are substantially resistant to the action of I as a result of breeding and/or genetic manipulation methods.

The compounds I or the herbicidal compositions containing them can be applied, for example, by spraying, atomizing, dusting, scattering or watering in the form of directly sprayable aqueous solutions, powders, suspensions, even high-percentage aqueous, oily or other suspensions or dispersions, emulsions, oil dispersions, pastes, dusting compositions, scattering compositions or granules. The application forms depend on the intended uses; if possible they should in each case guarantee the finest distribution of the active compounds according to the invention.

Suitable inert auxiliaries for the preparation of directly sprayable solutions, emulsions, pastes or oil dispersions are essentially: mineral oil fractions of medium to high boiling point, such as kerosene and diesel oil, coal-tar oils and oils of vegetable or animal origin, aliphatic, cyclic and aromatic hydrocarbons, eg. paraffins, tetrahydronaphthalene, alkylated naphthalenes and derivatives thereof, alkylated benzenes and derivatives thereof, alcohols such as methanol, ethanol, propanol, butanol and cyclohexanol, ketones such as cyclohexanone, strongly polar solvents, for example amines such as N-methylpyrrolidone, and water.

Aqueous application form can be prepared from emulsion concentrates, suspensions, pastes, wettable powders or water-dispersible granules by addition of water. To prepare emulsions, pastes or oil dispersions, the substances can be homogenized in water, as such or dissolved in an oil or solvent, by means of wetting agents, adhesives, dispersants or emulsifiers, However, concentrates consisting of active substance, wetting agent, adhesive, dispersant or emulsifier and possibly solvents or oil, which are suitable for dilution with water, can also be prepared.

Suitable surface-active substances are the alkali metal, alkaline earth metal or ammonium salts of aromatic sulfonic acids, eg. lignosulfonic acid, phenolsulfonic acid, naphthalenesulfonic acid and dibutylnaphthalenesulfonic acid, as well as of fatty acids, alkyl- and alkylarylsulfonates, alkyl sulfates, lauryl ether sulfates and fatty alcohol sulfates, and also salts of sulfated hexa-, hepta- and octadecanols as well as of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octyl phenol ethers, ethoxylated isooctyl-, octyl- or nonylphenol, alkylphenyl or tributylphenylpolyglycol ethers, alkylaryl polyether alcohols, isotridecyl alcohol, fatty alcohol ethylene oxide condensates, ethoxylated castor oil, polyoxyethylene alkyl ethers or polyoxypropylene alkyl ethers, lauryl alcohol polyglycol ether acetate, sorbitol esters, ligninsulfate waste liquors or methylcellulose.

Powder, scattering and dusting compositions can be prepared by mixing or conjoint grinding of the active substances with a solid carrier.

Granules, eg. coated, impregnated and homogeneous granules, can be prepared by binding the active compounds to solid carriers. Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground synthetic materials, fertilizers such as ammonium sulfate, ammonium phosphate, ammonium nitrate, ureas and plant products such as cereal flour, treebark meal, wood meal and nutshell meal, cellulose powder or other solid carriers.

The concentrations of the active compounds I in the ready-to-use formulations may be varied within a wide range, for instance between 0.01 and 95% by weight, preferably between 0.5 and 90% by weight. In this context the active compounds are employed in a purity of from 90% to 100%, preferably from 95% to 100% (according to NMR spectrum).

The formulation examples below illustrate the preparation of such formulations:

I. 20 parts by weight of compound No. Ia.071 are dissolved in a mixture which consists of 80 parts by weight of alkylated benzene, 10 parts by weight of the addition product of from 8 to 10 mol of ethylene oxide with 1 mol of oleic acid N-monoethanolamide, 5 parts by weight of the calcium salt of dodecylbenzenesulfonic acid and 5 parts by weight of the addition product of 40 mol of ethylene oxide with 1 mol of castor oil. By pouring out the solution and finely dispersing it in 100,000 parts by weight of water, an aqueous dispersion is obtained which contains 0.02% by weight of the active compound.

II. 20 parts by weight of compound No. Ia.047 are dissolved in a mixture which consists of 40 parts by weight of cyclohexanone, 30 parts by weight of isobutanol, 20 parts by weight of the addition product of 7 mol or ethylene oxide with 1 mol of isooctylphenol and 10 parts by weight of the addition product of 40 mol of ethylene oxide with 1 mol of castor oil. By pouring the solution into and finely dispersing it in 100,000 parts by weight of water, an aqueous dispersion is obtained which contains 0.02% by weight of the active compound.

III. 20 parts by weight of the active compound No. Ia.066 are dissolved in a mixture which consists of 25 parts by weight of cyclohexanone, 65 parts by weight of a mineral oil fraction with a boiling point of from 210 to 280° C. and 10 parts by weight of the addition product of 40 mol of ethylene oxide with 1 mol of castor oil. By pouring the solution into and finely dispersing it in 100,000 parts by weight of water, and aqueous dispersion is obtained which contains 0.02% by weight of the active compound.

IV. 20 parts by weight of the active compound No. Ia.122 are thoroughly mixed with 3 parts by weight of the sodium salt of diisobutylnaphthalene-α-sulfonic acid, 17 parts by weight of the sodium salt of a lignosulfonic acid from a sulfite waste liquor and 60 parts by weight of silica gel in powder form, and the mixture is ground in a hammer mill. By finely dispersing the mixture in 20,000 parts by weight of water, a spray mixture is obtained which contains 0.1% by weight of the active compound.

V. 3 parts by weight of the active compound No. Ia.161 are mixed with 97 parts by weight of finely divided kaolin. In this way, a dusting composition is obtained which contains 3% by weight of the active compound.

VI. 20 parts by weight of the active compound No. Ia.171 are intimately mixed with 2 parts by weight of the calcium salt of dodecylbenzenesulfonic acid, 8 parts by weight of fatty alcohol polyglycol ether, 2 parts by weight of the sodium salt of a phenol-urea-formaldehyde condensate and 68 parts by weight of a paraffinic mineral oil. A stable oily dispersion is obtained.

The application of the active compounds I or of the herbicidal composition can be carried out pre-emergence or post-emergence. If the active compounds are less tolerable for certain crop plants, then application techniques can be employed in which the herbicidal compositions are sprayed with the aid of spray equipment such that the leaves of the sensitive crop plants are if possible not affected, while the active compounds reach the leaves of unwanted plants growing under them or the uncovered soil surface (post-directed, lay-by).

Depending on the aim of control, time of year, target plants and growth stage, the application rates of active compound are from 0.001 to 3.0, preferably from 0.01 to 1, kg/ha of active substance (a.s.).

To widen the spectrum of action and to achieve synergistic effects, the substituted 3-phenylpyrazoles I can be mixed with numerous representatives of other herbicidal or growth-regulating active compound groups and applied jointly. For example, suitable co-components are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triziniones, uracils, benzofuran derivatives, cyclohexane-1, 3-dione derivative which carry eg. a carboxyl or carbimino group in position 2, quinolinecarboxylic derivatives, imidazolinones, sulfonamides, sulfonylureas, aryloxy- and heteroaryloxyphenoxypropionic acids and their salts, esters and amides and others.

Additionally, it may be useful to apply the compounds I on their own or together in combination with other herbicides, additionally mixed with further plant protection agents, for example with agents for controlling pests or phytopathogenic fungi or bacteria. Also of interest is the possibility of mixing with mineral salt solutions, which are employed for the elimination of nutritional and trace element deficiencies. Nonphytotoxic oils and oil concentrates can also be added.

PREPARATION EXAMPLES

Example 1

3-(4-Chlorophenyl)-5-difluoromethyl-1-methyl-1H-pyrazole 162 g (4.0 mol) of sodium hydroxide dissolved in 1 l of water were added to a solution of 169.1 g (0.811 mol) of 3-(4-chlorophenyl)-1-methyl-2-pyrazolin-5-one in 2.5 l of dioxane. Chlorodifluoromethane was passed into this mixture at 60–65° C. for 5 h, after which the reaction solution was stirred into 1.5 l of water. The mixture was worked up by extraction three times (in each case with about 1000 ml) with methyl tert-butyl ether. The combined organic phases were dried and concentrated under reduced pressure. The crude product was purified by chromatography on silica gel (eluent:hexane/ethyl acetate=7:3). Yield: 142.9 g; $^1$H-NMR (400 MHz, in CDCl$_3$): δ [ppm]=7.60 (d, 2H), 7.28 (d, 2H), 6.54 (t, 1H), 6.08 (s, 1H), 3.69 (s, 3H).

Precursor α: ethyl 4-chlorobenzoylacetate 200 g (1.29 mol) of 4-chloroacetophenone (dissolved in 500 ml of diethyl carbonate) were added dropwise at 60° C. to a mixture of 296.4 g (2.59 mol) of potassium tert-butylate and 2.25 l of diethyl carbonate. The suspension, which was stirrable with difficulty, was stirred at 60° C. for 3 h and then discharged into 2.7 l of 10% strength by weight sulfuric acid. The product was then extracted with ethyl acetate, the mixture being subsequently dried over magnesium sulfate and then concentrated under reduced pressure. The crude product obtained was purified by distillation. Yield: 268 g; b.p.: 130° C. at 0.4 mbar.

Precursor β): 3-(4-Chlorophenyl)-1-methyl-2-pyrazolin-5-one 71.2 g (1.55 mol) of methylhydrazine were added dropwise over the course of 40 minutes to a suspension of 267 g (1.19 mol) of ethyl 4-chlorobenzoylacetate in 1.5 l of acetate, the temperature rising to 50° C. When the addition was complete the reaction mixture was stirred at 100° C. for 2 h and then cooled, and finally about 1.5 l of ether and about 1.5 l of water were added. The solid product (about 66.5 g) was separated off and washed with a mixture of petroleum ether and diethyl ether (1:1). The organic phase, which still contained dissolved product, was washed with 4 times 500 ml of saturated aqueous sodium hydrogen carbonate solution and then concentrated (residual quantity about 200 ml). Addition of about 1000 ml of water led to precipitation of a further quantity of product. This product was also separated off and then washed with a 1:1 mixture of petroleum ether and diethyl ether. Total product quantity: 171 g; m.p. 189° C.

Example 2

4-Chloro-3-(4-chlorophenyl)-5-difluoromethyoxy-1-methyl-1H-pyrazole (No. Ia.162)

74.0 g (0.549 mol) of sulfuryl chloride dissolved in 200 ml of carbon tetrachloride were added slowly dropwise to a solution of 128.9 g (0.5 mol) of 3-(4-chlorophenyl)-5-difluoromethoxy-1-methyl-1H-pyrazole in 500 ml of carbon tetrachloride, the ensuing reaction being exothermic with evolution of gas. After the end of the reaction the mixture was stirred at about 20° C. for a further 2 h. The reaction solution was then washed with about 300 ml each of water, saturated sodium hydrogen carbonate solution and saturated sodium chloride solution, and then dried and concentrated. Yield: 139.3 g; $^1$H-NMR (270 MHz, in CDCl$_3$): δ [ppm]= 7.79 (d, 2H), 7.43 (d, 2H), 6.70 (t, 1H), 3.85 (s, 3H).

Example 3

3-(3-Bromomethyl-4-chlorophenyl)-4-chloro-5-difluoromethoxy-1-methyl-1H-pyrazole (No. Ia.74)

A mixture of 20.0 g (65 mmol) of 4-chloro-5-difluoromethoxy-3-(4-chloro-3-methylphenyl)-1-methyl-1H-pyrazole (prepared as described in Example 2), 17.4 g (98 mmol) of N-bromosuccinimide and 200 ml of carbon tetrachloride was refluxed for 3 h under irradiation with a UV lamp. The solid constituents were then filtered off and were washed with a little methylene chloride. The solvent was removed under reduced pressure, and then the residue was purified by chromatography on silica gel (eluent: methylene chloride/hexane=8:2). Yield: 11.0 g; $^1$H-NMR (270 MHz, in CDCl$_3$); δ [ppm]=7.98 (s, 1H), 7.80 (d, 1H), 7.46 (d, 1H), 6.70 (t, 1H), 4.64 (s, 2H), 3.87 (s, 3H).

Example 4

3-(3-Dibromomethyl-4-chlorophenyl)-4-chloro-5-difluoromethoxy-1-methyl-1H-pyrazole (No. Ia.161)

10.5 g (58.8 mmol) of N-bromosuccinimide were added to a solution of 3.0 g (9.8 mmol) of 4-chloro-5-difluoromethoxy-3-(4-chloro-3-methylphenyl)-1-methyl-1H-pyrazole in 100 ml of carbon tetrachloride. This mixture was refluxed for 1 hour under irradiation with a 150 watt mercury high-pressure lamp. The reaction mixture was then filtered. Concentration of the filtrate under reduced pressure given 3.9 g of crude product which was used without further purification for the following reactions. $^1$H-NMR (400 MHz, in CDCl$_3$): δ [ppm]=8.56 (s, 1H), 7.79 (d, 1H), 7.46 (d, 1H), 7.15 (d, 1H), 6.70 (t, 1H), 3.85 (s, 3H).

Example 5

4-Chloro-3-(4-chloro-3-formylphenyl)-5-difluoromethoxy-1-methyl-1H-pyrazole (No. Ia.106)

4.65 g (10 mmol) of 3-(3-dibromomethyl)-4-chlorophenyl)-4-chloro-5-difluoromethoxy-1-methyl-1H-pyrazole were added a little at a time at 85° C. to 7 ml of concentrated sulfuric acid. The mixture was then stirred at 100° C. for 5 minutes after which the reaction solution was stirred into 40 ml of ice-water. The solid product formed was separated off and dried. Yield: 3.0 g; $^1$H-NMR (270 MHz, in CDCl$_3$): δ [ppm]=10.50 (s, 1H), 8.45 (s, 1H), 8.06 (d, 1H), 7.52 (d, 1H), 6.71 (t, 1H), 3.82 (s, 3H).

Example 6

3-(3-Carboxy-4-chlorophenyl)-4-chloro-5-difluoromethoxy-1-methyl-1H-pyrazole (No. Ia.095)

A solution of 4 g (34 mmol) of sodium dihydrogen phosphate in 40 ml of water and then 12.5 ml of 35% hydrogen peroxide solution were added at 10–15° C. to a solution of 40 g (125 mmol) of 4-chloro-3-(4-chloro-3-formylphenyl)-5-difluoromethoxy-1-methyl-1H-pyrazole in 125 ml of acetonitrile. A solution of 18.1 g (200 mmol) of sodium chlorite in 158 ml of water was then added dropwise at 10° C. to the mixture. After stirring for one hour the mixture was acidified to pH 1 with 3N hydrochloric acid. The product then present in suspended form in the reaction mixture was separated off and recrystallized from methanol/water. Yield: 24.5 g.

Example 7

4-Chloro-3-(4-chloro-3-[N-(methoxycarbonylmethyl)-methylaminocarbonyl]-phenyl)-5-difluoromethoxy-1-methyl-1H-pyrazole (No. Ia.208)

3.5 g (25 mmol) of potassium carbonate (ground) and 1.2 g (8.4 mmol) of methyl methylaminoacetate hydrochloride were added to a solution of 3 g (8.4 mmol) of 4-chloro-3-(4-chloro-3-chloro-carbonylphenyl)-5-difluoromethoxy-1- methyl-1H-pyrazole in 80 ml of tetrahydrofuran. The mixture was then heated at 60° C. for 5 hours, then cooled and concentrated. Water and ethyl acetate were added to the residue. The organic phase was separated off, dried over magnesium sulfate and concentrated. The crude product obtained was purified by column chromatography on silica gel (eluent: hexane/ethyl acetate=1:1). Yield: 1.9 g.
Precursor α): 4-Chloro-3-(4-chloro-3-chlorocarbonylphenyl)-5-difluoromethyoxy-1-methyl-1H-pyrazole 11.2 g (88 mmol) of oxalyl chloride and one drop of dimethyl-formamide were added dropwise in succession to a solution of 11 g (29 mmol) of 3-(3-carboxy-4-chlorophenyl)-4-chloro-5-difluoromethoxy-1-methyl-1H-pyrazole in 100 ml toluene. The reaction mixture was stirred at room temperature for 5 hours and then concentrated. Yield: quantitative.

Example 8

4-Chloro-3-(4-chloro-3-[(2-methoxyimino)ethoxycarbonyl]phenyl-5-difluoromethoxy-1-methyl-1H-pyrazole (No. Ia.149)

1.7 g (12 mmol) of ground potassium carbonate were added to a solution of 3 g (8.9 mmol) of 3-(3-carboxy-4-chlorophenyl)-4-chloro-5-difluoromethoxy-1-methyl-1H-pyrazole in 60 ml of dimethylformamide. After dropwise addition of 1.0 g (8.9 mmol) of 1-chloro-2-methoxyiminoethane, the mixture was heated at 60° C. for 5 hours, then cooled and concentrated. Water was added to the residue, and the product was then extracted with ethyl acetate. The ethyl acetate solution was subsequently washed with water again, then dried over magnesium sulfate and concentrated. The crude product was purified by column chromatography on silica gel (eluent: hexane/ethyl acetate= 2:1). Yield: 1.3 g (as E/Z mixture).

Example 9

4-Chloro-3-[4-chloro-3-(ethoxyiminomethyl)-phenyl]-5-difluoromethoxy-1-methyl-1H-pyrazole (No. Ia.122)

2.6 g (8 mmol) of 4-chloro-3-formylphenyl)-5-difluoromethoxy-1-methyl-1H-pyrazole and 1.3 g (10 mmol) of 45% strength by weight aqueous ethoxyamine solution were heated at 50° C. for 3 hours. Subsequently a further 2 g of the same solution were added, and heating at 50° C., continued for 3 hours. The solution was stirred overnight at room temperature and then concentrated. The crude product was purified by column chromatography on silica gel (eluent: cyclohexane/ethyl acetate=50:1). Yield: 1.7 g.

Example 10

4-Chloro-3-[4-chloro-3-(4,4-diethoxy-3-oxobut-1-en1-yl)phenyl]-5-difluoromethoxy-1-methyl-1H-pyrazole (No. Ia.222)

5.1 g of (3,3-diethoxy-2-oxopropylidene)(triphenyl) phosphorane were added to a solution of 2 g (6.2 mmol) of 4-chloro-3-(4-chloro-3-formylphenyl)-5-difluoromethoxy-1-methyl-1H-pyrazole in 20 ml of dimethylformamide, and the mixture was hen heated at 80–90° C. for 5 hours. The mixture was then concentrated and the crude product thus obtained was purified by chromatography on silica gel (eluent: hexane/ethyl acetate=4:1). Yield: 2.1 g.

Example 11

4-Chloro-3-[4-chloro-3-(dimethoxymethyl)-phenyl]-5-difluoromethoxy-1-methyl-1H-pyrazole (No. Ia.107)

15 g of montmorillonite K10 were added to a solution of 16 ml of trimethyl orthoformate in 80 ml of dichloromethane. A solution of 6.4 g (20 mmol) of 4-chloro-3-(4-chloro-3-formylphenyl)-5-difluoromethoxy-1-methyl-1H-pyrazole in 20 ml of dichloromethane was added dropwise at 5° C. to this mixture. The mixture was then stirred at room temperature overnight. The solids were then separated off and the clear reaction solution which remained was concentrated. Yield: 6.7 g.

Example 12

4-Chloro-3-[4-chloro-3-(1,3-dithian-2-yl)-phenyl]-5-difluoromethoxy-1-methyl-1H-pyrazole (No. Ia.119)

0.5 g (4.6 mmol) of 1,3-propanedithiol was added to a solution of 1.7 g (4.6 mmol) of 4-chloro-3-[4-chloro-3-(dimethoxymethyl)phenyl]-5-difluoromethoxy-1-methyl-1H-pyrazole in 50 ml of toluene. The mixture was heated to 60–70° C. and then a spatula-tipful of p-toluenesulfonic acid was added. The reaction mixture was stirred at reflux temperature for 3 hours and then cooled and diluted with 50 ml of toluene. The organic phase was washed with 10% strength by weight sodium hydrogen carbonate solution and water and then dried over magnesium sulfate and concentrated. The crude product thus obtained was purified by chromatography on silica gel (eluent: hexane/ethyl acetate= 4:1). Yield: 1.8 g.

Example 13

3-(3-Acetoxymethyl-4-chlorophenyl)-4-chloro-5-difluoromethoxy-1-methyl-1H-pyrazole (No. Ia.148)

A solution of 6.8 g (18 mmol) of 3-(3-bromomethyl-4-chlorophenyl)-4-chloro-5-difluoromethoxy-1-methyl-1H-pyrazole and 1.5 g (18 mmol) of sodium acetate in 20 ml of dimethylformamide was stirred overnight and then stirred into 100 ml of cold water. The product was extracted from the aqueous phase using ethyl acetate. The ethyl acetate phase was dried over magneisum sulfate and concentrated. The crude product thus obtained was purified by silica gel chromatography (eluent: hexane/ethyl acetate=9:1). Yield: 4.7 g.

Example 14

4-Chloro-3-(4-chloro-3-hydroxymethylphenyl)-5-difluoromethoxy-1-methyl-1H-pyrazole (No. Ia.143)

6.3 ml (16 mmol) of 10% strength sodium hydroxide solution were added dropwise to a solution of 3.2 g (8.8 mmol) of 3-(3-acetoxymethyl-4-chlorophenyl)-4-chloro-5-difluoromethoxy-1-methyl-1H-pyrazole in 10 ml of dioxane and 10 ml of water. The mixture was stirred for 1 hour and then neutralized with 3N hydrochloric acid. The product was extracted from the aqueous phase with ethyl acetate, after which the organic phase was dried over magnesium sulfate and then concentrated. The crude product thus obtained was purified by column chromagraphy on silica gel (eluent: hexane/ethyl acetate=4:1). Yield: 1.3 g.

Example 15

4-Chloro-3-(4-chloro-3-methoxymethylphenyl)-5-difluoromethoxy-1-methyl-1H-pyrazole (No. Ia.075)

1.6 g (9.0 mmol) of a 30% strength by weight solution of sodium methylate in methanol was added dropwise to a solution of 2.3 g (6.0 mmol) of 3-(3-bromomethyl-4-chlorophenyl)-4-chloro-5-difluoromethoxy-1-methyl-1H-pyrazole in 60 ml of methanol. The reaction mixture was stirred at 40° C. for 3 hours and then concentrated. The residue was taken up in water and dichloromethane, after which concentrated hydrochloric acid was added until the acid reaction took place. Product remaining in the aqueous phase was extracted with dichloromethane. The combined dichloromethane phases were dried over magnesium sulfate and concentrated. Yield: 1.8 g.

Example 16

4-Chloro-3-[4-chloro-3-(ethylthiomethyl)-phenyl]-5-difluoromethoxy-1-methyl-1H-pyrazole (No. Ia.090)

1.3 g (16 mmol) of sodium thioethylate were added to a solution of 6 g (16 mmol) of 3-(3-bromomethyl-4-chlorophenyl)-4-chloro-5-difluoromethoxy-1-methyl-1H-pyrazole in 100 ml of acetone. The mixture was stirred overnight and then water was added. The product was extracted from the aqueous phase with ethyl acetate. The ethyl acetate phase was subsequently dried over magnesium sulfate and then concentrated. The crude product thus obtained was purified by column chromatography on silica gel (eluent: hexane/ethyl acetate=4:1). Yield: 4.5 g.

Example 17

4-Chloro-3-[4-chloro-3-(ethylsulfinylmethyl)-phenyl]-5-difluoromethoxy-1-methyl-1H-pyrazole (No. Ia.167)

1.4 g (4 mmol) of m-chloroperbenzoic acid were added a little at a time at 0° C. to a solution of 1.5 g (4 mmol) of 4-chloro-3-[4-chloro-3-(ethylthiomethyl)phenyl]-5-difluoromethoxy-1-methyl-1H-pyrazole in 40 ml of dichloromethane. The mixture was stirred at 0° for 30 minutes was subsequently stirred at room temperature for 4 hours and then the solids were removed by filtration. The filtrate was concentrated, and the crude product thus obtained was purified by chromatography on silica gel (eluent: hexane/ethyl acetate=1:1). Yield: 0.2 g.

Example 18

4-Chloro-3-[4-chloro-3-(ethylsulfonylmethyl) phenyl)-5-difluoromethoxy-1-methyl-1H-pyrazole (No. Ia.168)

0.2 g of disodium tungstate (VI) was added to a solution of 1.6 g (4.4 mmol) of 4-chloro-3-[4-chloro-3-(ethylthiomethyl)phenyl]-5-difluoromethoxy-1-methyl-1H-pyrazole in 12 ml of acetate acid. Then 2 ml of 30% strength hydrogen peroxide solution were added dropwise to this mixture. The reaction mixture was stirred for 1 hour and then 100 ml of water were added. The aqueous phase was separated off and the product was extracted therefrom with ethyl acetate. The ethyl acetate phase was then dried over magnesium sulfate and subsequently concentrated. The crude product thus obtained was purified by column chromatography on silica gel (eluent: hexane/ethyl acetate=4:1). Yield: 1.4 g.

Example 19

4-Chloro-3-(4-chloro-3-chlorosulfonylphenyl)-5-difluoromethoxy-1-methyl-1H-pyrazole (No. Ia.047)

47.9 g (0.16 mol) of 4-chloro-3-(4-chlorophenyl)-5-difluoromethoxy-1-methyl-1H-pyrazole were added a little at a time at 0° C. to 91 ml of chlorosulfonic acid. The mixture was stirred at 130° C. for 4 hours and then cooled, and the solution was poured carefully into ice-water. Product dissolved in the aqueous phase was extracted twice with dichloromethane. The combined organic phases were subsequently washed with saturated sodium hydrogen carbonate solution and with sodium chloride solution, then dried over magnesium sulfate and finally concentrated. Yield: 47.9 g.

Example 20

4-Chloro-3-[4-chloro-3-(cyclopropylaminosulfonyl)-phenyl]-5-difluoromethoxy-1-methyl-1H-pyrazole (No. Ia.171)

0.9 g (16 mmol) of cyclopropylamine was added to a solution of 3 g (7.6 mmol) of 4-chloro-3-(4-chloro-3-chlorosulfonylphenyl)-5-difluoromethoxy-1-methyl-1H-pyrazole in 25 ml of tetrahydrofuran. The mixture was stirred at room temperature for 4 hours and then concentrated to dryness. The solid residue was washed with a little diisopropyl ether. Yield: 3 g.

Example 21

4-Chloro-3-(4-chloro-3-[N-(methylaminocarbonylmethyl)-methylaminosulfonyl]-phenyl)-5-difluoromethoxy-1-methyl-1H-pyrazole (No. Ia.184)

2.5 g of 40% strength aqueous methylamine solution was added to a solution of 1.5 g (3.3 mmol) of 4-chloro-3-(4-chloro-3-[N-(methoxycarbonylmethyl)methyl)methylaminosulfonyl]phenyl)-5-difluoromethoxy-1-methyl-1H-pyrazole in 40 ml of tetrahydrofuran. The reaction mixture was stirred at 50° C. for 2 hours, and then a further 3 ml of the methylamine solution were added. The mixture was subsequently heated at 50° C. for 6 hours. It was then concentrated and the residue was taken up in ethyl acetate. The ethyl acetate phase was washed with water, dilute hydrochloric acid and saturated sodium chloride solution, then dried over magnesium sulfate and finally concentrated. Washing with a little hexane/ethyl acetate (9:1) gave 1.1 g of the target product.

Example 22

4-Chloro-3-(4-chloro-3-nitrophenyl)-5-difluoromethoxy-1-methyl-1H-pyrazole (No. Ia.059)

113.4 g (0.387 mol) of 4-chloro-3-(4-chlorophenyl)-5-difluoromethoxy-1-methyl-1H-pyrazole were added a little at a time at −40° C. to 500 ml of 98% strength nitric acid. The mixture was stirred at this temperature for 2 hours and then the solution was stirred into ice. The product was extracted from the aqueous phase with dichloromethane. The dichloromethane phase was subsequently washed a number of times with water and then with saturated sodium chloride solution. Drying over magnesium sulfate and removal of the dichloromethane gave 119.6 g of the target product.

Example 23

3-(3-Amino-4-chlorophenyl)-4-chloro-5-difluoromethoxy-1-methyl-1H-pyrazole (No. Ia.060)

155 ml of acetic acid were added to a suspension of 32.1 g (0.576 mol) of iron powder in 305 ml of ethanol. 64.9

(0.192 mol) of 4-chloro-3-(4-chloro-3-nitrophenyl)-5-difluoromethoxy-1-methyl-1H-pyrazole were added a little at a time to this mixture at 70–75° C. After 1 hour, 0.5 l of ethyl acetate was added and the solution was then filtered over a silica gel bed and subsequently concentrated. The residue was taken up in ethyl acetate. The ethyl acetate phase was washed with water, saturated sodium hydrogen carbonate solution and saturated sodium chloride solution, then dried over magnesium sulfate and finally concentrated. Yield: 56.4 g.

Example 24

4-Chloro-3-[4-chloro-3-(cyclopropylcarbonylamino)-phenyl]-5-difluoromethoxy-1-methyl-1H-pyrazole (No. Ia.142)

1.0 g (13 mmol) of pyridine and 0.7 g (6.5 mmol) of cyclopropanecarbonyl chloride were added to a solution of 2.0 g (6.5 mmol) of 3-(3-amino-4-chlorophenyl)-4-chloro-5-difluoromethoxy-1-methyl-1H-pyrazole in 30 ml of tetrahydrofuran. The solution was stirred at room temperature overnight and at 50° C. for 2 hours, an then concentrated. The residue was taken up in ethyl acetate. The ethyl acetate was washed in succession with cold 1N hydrochloric acid, water and saturated sodium chloride solution, then dried over magnesium sulfate and finally concentrated. Yield: 2.2 g.

Example 25

4-Chloro-3-(4-chloro-3-[di(methylsulfonyl)amino]-phenyl]-5-difluoromethoxy-1-methyl-1H-pyrazole (No. Ia.062)

2.3 g (22 mmol) of triethylamine were added to a solution of 3 g (10 mmol) of 3-(3-amino-4-chlorophenyl)-4-chloro-5-difluoromethoxy-1-methyl-1H-pyrazole in 50 ml of dichloromethane. 2.5 g (21 mmol) of methanesulfonyl chloride were added dropwise to this mixture at 0° C. The reaction mixture was stirred at room temperature for 2 hours and then washed with water. The organic phase was subsequently dried over magnesium sulfate and concentrated. The solid product was washed with a little diethyl ether. Yield: 3.1 g.

Example 26

4-Chloro-3-[4-chloro-3-(methylsulfonylamino)-phenyl]-5-difluoromethoxy-1-methyl-1H-pyrazole (No. Ia.061)

0.3 g (4.7 mmol) of potassium hydroxide (dissolved in a little water) was added to a solution of 0.9 g (2.3 mmol) of 4-chloro-3-(4-chloro-3-[di-(methylsulfonyl)-amino]-phenyl)-5-difluoromethoxy-1-methyl-1H-pyrazole in 30 ml of methanol. The mixture was stirred at room temperature for 18 hours and then concentrated. The residue was taken up in 1N hydrochloric acid and then extracted with ethyl acetate. Drying of the organic phase with magnesium sulfate followed by concentration gave 0.7 g of the target product.

Example 27

4-Chloro-3-[4-chloro-3-hydrozineophenyl]-5-difluoromethoxy-1-methyl-1H-pyrazole hydrochloride (No. Ia.189)

4.45 g (14.5 mmol) of 3-(3-amino-4-chlorophenyl)-4-chloro-5-difluoromethoxy-1-methyl-1H-pyrazole were heated briefly at 80° C. and thus dissolved in 26 ml of concentrated hydrochloric acid. The solution was then cooled to 0° C. and, at this temperature, a solution of 1.0 g (14.5 mmol) of sodium nitrite in 4 ml of water was added dropwise. Stirring at 0° C. was then continued for 30 minutes (diazonium salt solution).

The diazonium salt solution was added dropwise to a solution, cooled to 0–5° C., of 8.1 g (3.6 mmol) of tin(II) chloride dihydrate in 5 ml of concentrated hydrochloric acid. The reaction mixture was then stirred at room temperature for two hours and subsequently poured into 200 ml of water. The solid target product was isolated from the resulting suspension. Yield: 3.7 g.

Example 28

4-Chloro-3-[4-chloro-3-(2-ethoxycarbonylhydrazino)-phenyl]-5-difluoromethoxy-1-methyl-1H-pyrazole (No. Ia.190)

13.3 g (103 mmol) of ethyl diisopropylamne were added to a solution of 17.6 g (49 mmol) of 4-chloro-3-(4-chloro-3-hyudrazinophenyl)-5-difluoromethoxy-1-methyl-1H-pyrazole hydrochloride in 400 ml of tetrahydrofuran. 5.8 g (54 mmol) of ethyl chloroformate were added dropwise at 0° C. to this mixture, followed by stirring at room temperature for 30 hours. The suspension obtained was then filtered. The filtrate was concentrated and the residue was taken up in ethyl acetate. The ethyl acetate phase was washed with water and with saturated sodium chloride solution, then dried over magnesium sulfate and finally concentrated. Yield: 15.6 g.

Example 29

4-Chloro-3-[4-chloro-3-(2-ethoxycarbonylazo)-phenyl]-5-difluoromethoxy-1-methyl-1H-pyrazole (No. Ia.191)

A solution of 2.1 g (6.6 mmol) of m-chloroperbenzoic acid in 10 ml of dichloromethane was added dropwise to a solution of 2.1 g (5.3 mmol) of 4chloro-3-[4-chloro-3-(2-ethoxycarbonylhydrazino)-phenyl]-5-difluoromethoxy-1-methyl-1H-pyrazole in 15 ml of dichloromethane. The mixture was stirred at 35° C. for 30 minutes and poured into 50 ml of water. The organic phase was separated off and washed with 10% strength by weight sodium hydrogen carbonate solution, then dried over magnesium sulfate and finally concentrated. The crude product was purified by column chromatography on silica gel (eluent: hexane/ethyl acetate=4:1). Yield: 0.5 g.

Example 30

4-Chloro-3-(4-chloro-3-iodophenyl)-5-difluoromethoxy-1-methyl-1H-pyrazole (No. Ia.219)

A diazonium salt solution was prepared as described in Example 27 using 4.5 g (14.7 mmol) of 3-(3-amino-4-chlorophenyl)-4-chloro-5-difluoromethoxy-1-methyl-1H-pyrazole, 7 ml of concentrated hydrochloric acid, 1.1 g of (16.2 mmol) of sodium nitrite and 15 ml of water. This diazonium salt solution was added dropwise to 24.4 g (14.6 mmol) of potassium iodide in 30 ml of water. The mixture was stirred overnight and then extracted with dichloromethane. The dichloromethane phase was washed with sodium hydroxide solution and saturated sodium chloride solution, then dried over magnesium sulfate and finally concentrated. The crude product was purified by silica gel chromatography (eluent: hexane/ethyl acetate=6:1). Yield: 2.9 g.

Example 31

4-Chloro-3-(4-cyano-3-nitrophenyl)-5-difluoromethoxy-1-methyl-1H-pyrazole (No. If.059)

1.1 g (17 mmol) of potassium cyanide were added to a solution of 5.0 g (15.6 mmol) of 4-chloro-3-(4-fluoro-3-nitrophenyl)-5-difluoromethoxy-1-methyl-1H-pyrazole in 70 ml of dimethyl sulfoxide. The mixture was then stirred at 50° C. for 5 hours and at room temperature for 3 days. The reaction mixture was poured into ice-water and then the product was extracted with methyl tert-butyl ether. The ether phase was dried over magnesium sulfate and concentrated. The crude product was purified by column chromatography on silica gel (eluent: hexane/ethyl acetate=3:1). Yield: 2.7 g.

Example 32

4-Chloro-3-(4-cyano-3-methoxyphenyl)-5-difluoromethoxy-1-methyl-1H-pyrazole (No. If.001)

0.9 ml of a 30% strength by weight solution of sodium methylate in methanol was added to a solution of 1.4 g (4.3 mmol) of 4-chloro-3-(4-cyano-3-nitrophenyl)-5-difluoromethoxy-1-methyl-1H-pyrazole in 30 ml of methanol. The mixture was stirred at room temperature for 6 hours and then cooled to 0° C. for about 16 h. The solid reaction product was then isolated. Yield: 0.6 g.

Tables 1–7 below indicate further compounds which were prepared in the same way or can be prepared by methods which are either described above or known per se.

TABLE 1

I ($R^2, R^5 = Cl; R^3 = CH_3$;
$Z—R^4 = OCHF_2$)

| No. | $R^1$ | m.p./MS $[mz^{-1}]$/ $^1H$—NMR [ppm] |
|---|---|---|
| Ia.001 | —OCH$_3$ | |
| Ia.002 | —OC$_2$H$_5$ | |
| Ia.003 | —OCH$_2$—C$_2$H$_5$ | |
| Ia.004 | —OCH(CH$_3$)$_2$ | |
| Ia.005 | —OCH$_2$—CH$_2$—C$_2$H$_5$ | |
| Ia.006 | —OCH(CH$_3$)—C$_2$H$_5$ | |
| Ia.007 | —OCH$_2$—CH(CH$_3$)$_2$ | |
| Ia.008 | —OCH$_2$—CH$_2$—CH$_2$—C$_2$H$_5$ | |
| Ia.009 | —OCH$_2$—CH═CH$_2$ | |
| Ia.010 | —OCH$_2$—CH═CHCl | |
| Ia.011 | —OCH$_2$—C≡CH | |
| Ia.012 | —OCH(CH$_3$)—C≡CH | |
| Ia.013 | —OCH$_2$—CO—OCH$_3$ | |
| Ia.014 | —OCH$_2$—CO—OC$_2$H$_5$ | |
| Ia.015 | —OCH(CH$_3$)—CO—OCH$_3$ | |
| Ia.016 | —OCH(CH$_3$)—CO—OC$_2$H$_5$ | |
| Ia.017 | —O-cyclopentenyl | |
| Ia.018 | —OCH$_2$—CN | |
| Ia.019 | —OCH(CH$_3$)—CN | |
| Ia.020 | —OH | |
| Ia.021 | —OCH$_2$—CO—O—(CH$_2$)$_4$—CH$_3$ | |
| Ia.022 | —OCH(CH$_3$)—CO—O—(CH$_2$)$_4$—CH$_3$ | |
| Ia.023 | —OCH$_2$-phenyl | |
| Ia.024 | —SCH$_3$ | |
| Ia.025 | —SC$_2$H$_5$ | |
| Ia.026 | —SCH$_2$—C$_2$H$_5$ | |
| Ia.027 | —SCH(CH$_3$)$_2$ | |
| Ia.028 | —SCH$_2$—CH$_2$—C$_2$H$_5$ | |
| Ia.029 | —SCH(CH$_3$)—C$_2$H$_5$ | |
| Ia.030 | —SCH$_2$—CH(CH$_3$)$_2$ | |
| Ia.031 | —SCH$_2$—CH$_2$—CH$_2$—C$_2$H$_5$ | |
| Ia.032 | —SCH$_2$—CH═CH$_2$ | |
| Ia.033 | —SCH$_2$—CH═CH—Cl | |
| Ia.034 | —SCH$_2$—C≡CH | |
| Ia.035 | —SCH(CH$_3$)—C≡CH | |
| Ia.036 | —SCH$_2$—CO—OCH$_3$ | |
| Ia.037 | —SCH$_2$—CO—OC$_2$H$_5$ | |
| Ia.038 | —SCH(CH$_3$)—CO—OCH$_3$ | |
| Ia.039 | —SCH(CH$_3$)—CO—OC$_2$H$_5$ | |
| Ia.040 | —S-cyclopentyl | |
| Ia.041 | —SCH$_2$—CN | |
| Ia.042 | —SCH(CH$_3$)—CN | |

TABLE 1-continued $(R^2, R^5 = Cl; R^3 = CH_3;$
$Z-R^4 = OCHF_2)$

| No. | $R^1$ | m.p./MS [mz$^{-1}$]/ $^1$H—NMR [ppm] |
|---|---|---|
| Ia.043 | —SCH$_2$—CO—O—(CH$_2$)$_4$—CH$_3$ | |
| Ia.044 | —SCH(CH$_3$)—CO—O—(CH$_2$)$_4$—CH$_3$ | |
| Ia.045 | —SCH$_2$-phenyl | |
| Ia.046 | —SCH$_2$—(4-Cl-phenyl) | |
| Ia.047 | —SO$_2$—Cl | 102–105° C. |
| Ia.048 | —SO$_2$—NH$_2$ | 8.65(s, 1H), 8.05(d, 1H), 7.58(d, 1H), 6.70(t, 1H), 5.21(s, 2H), 3.84(s, 3H) |
| Ia.049 | —SO$_2$—NH—CH$_3$ | 8.67(s, 1H), 8.07(d, 1H), 7.60(d, 1H), 6.71(t, 1H), 4.95(d, 1H), 3.84(s, 3H), 2.69(d, 3H) |
| Ia.050 | —SO$_2$—N(CH$_3$)$_2$ | 8.60(s, 1H), 8.03(d, 1H), 7.60(d, 1H), 6.71(t, 1H), 3.85(s, 3H), 2.94(s, 6H) |
| Ia.051 | —SO$_2$—NH—C$_2$H$_5$ | |
| Ia.052 | —SO$_2$—N(CH$_3$)—C$_2$H$_5$ | |
| Ia.053 | —SO$_2$—N(C$_2$H$_5$)$_2$ | |
| Ia.054 | —SO$_2$—(pyrrolidin-1-yl) | 8.63(s, 1H), 8.02(d, 1H), 7.60(d, 1H), 6.71(t, 1H), 3.86(s, 3H), 3.50–3.40 (m, 4H), 2.00–1.87(m, 4H) |
| Ia.055 | —SO$_2$-(morpholin-4-yl) | |
| Ia.056 | —SO$_2$-NH-phenyl | |
| Ia.057 | —SO$_2$—N(CH$_3$)-phenyl | |
| Ia.058 | —SO$_2$—NH—CH$_2$-phenyl | |
| Ia.059 | —NO$_2$ | 92–93° C. |
| Ia.060 | —NH$_2$ | 7.28(s, 1H), 7.27(d, 1H), 7.21(d, 1H), 6.67(t, 1H), 4.11(s, 2H), 3.80(s, 3H) |
| Ia.061 | —NH—SO$_2$—CH$_3$ | 8.22(s, 1H), 7.68(d, 1H), 7.48(d, 1H), 6.86(s, 1H), 6.70(t, 1H), 3.84(s, 3H), 3.10(s, 3H) |
| Ia.062 | —N(SO$_2$—CH$_3$)$_2$ | 153–154° C. |
| Ia.063 | —NH—SO$_2$—C$_2$H$_5$ | 83° C. |
| Ia.064 | —N(SO$_2$—C$_2$H$_5$)$_2$ | 96° C. |
| Ia.065 | —NH—SO$_2$—CH$_2$—C$_2$H$_5$ | |
| Ia.066 | —NH—CHO | |
| Ia.067 | —NH—CO—CH$_3$ | 146° C. |
| Ia.068 | —NH—CO—C$_2$H$_5$ | |
| Ia.069 | —N(CO—CH$_3$)—SO$_2$—CH$_3$ | |
| Ia.070 | —N(CO—CH$_3$)—SO$_2$—C$_2$H$_5$ | |
| Ia.071 | —CH$_3$ | 7.74(s, 1H), 7.65(d, 1H), 7.39(d, 1H), 6.70(t, 1H), 3.85(s, 3H), 2.45(s, 3H) |
| Ia.072 | —CH=CH—CH$_3$ | |
| Ia.073 | —CH=CH—CH(OCH$_2$CH$_2$CH$_2$O) | 8.12(s, 1H), 7.72(d, 1H), 7.41(d, 1H), 7.21(d, 1H), 6.70(t, 1H), 6.29(d, 1H), 5.21(d, 1H), 4.28–4.14 (m, 2H), 4.00–3.88(m, 2H), 3.84(s, 3H), 2.30–2.13 (m, 1H), 1.481–1.34(m, 1H) |
| Ia.074 | —CH$_2$—Br | 7.98(s, 1H), 7.80(d, 1H), 7.46(d, 1H), 6.70(t, 1H), 4.64(s, 2H), 3.87(s, 3H) |
| Ia.075 | —CH$_2$—OCH$_3$ | 54–55° C. |
| Ia.076 | —CH$_2$—OC$_2$H$_5$ | 8.02(s, 1H), 7.73(d, 1H), |

TABLE 1-continued $(R^2, R^5 = Cl; R^3 = CH_3;$
$Z—R^4 = OCHF_2)$

| No. | $R^1$ | m.p./MS [mz$^{-1}$]/ $^1$H—NMR [ppm] |
|---|---|---|
| | | 7.41(d, 1H), 6.69(t, 1H), 4.67(s, 2H), 3.87(s, 3H), 3.63(q, 2H), 1.30(t, 3H) |
| Ia.077 | —CH$_2$—OCH$_2$—C$_2$H$_5$ | |
| Ia.078 | —CH$_2$—OCH(CH$_3$)$_2$ | 8.04(s, 1H), 7.73(d, 1H), 7.42(d, 1H), 6.70(t, 1H), 4.65(s, 2H), 3.84(s, 3H), 3.75(m, 1H), 1.25(d, 6H), |
| Ia.079 | —CH$_2$—O—(CH$_2$)$_3$—CH$_3$ | 8.00(s, 1H), 7.72(d, 1H), 7.39(d, 1H), 6.68(t, 1H), 4.62(s, 2H), 3.79(s, 3H), 3.57(t, 2H), 1.65(m, 2H), 1.44(m, 2H), 0.95(t, 3H) |
| Ia.080 | —CH$_2$—OCH(CH$_3$)—C$_2$H$_5$ | |
| Ia.081 | —CH$_2$—OCH$_2$—CH(CH$_3$)$_2$ | |
| Ia.082 | —CH$_2$—OCH$_2$—CH=CH$_2$ | |
| Ia.083 | —CH$_2$—OCH$_2$—C≡C—H | |
| Ia.084 | —CH$_2$—OCH$_2$—CO—OCH$_3$ | |
| Ia.085 | —CH$_2$—OCH$_2$—CO—OC$_2$H$_5$ | |
| Ia.086 | —CH$_2$—OCH(CH$_3$)—CO—OCH$_3$ | |
| Ia.087 | —CH$_2$—OCH(CH$_3$)—CO—OC$_2$H$_5$ | |
| Ia.088 | —CH$_2$—O-cyclopentyl | |
| Ia.089 | —CH$_2$—SCH$_3$ | 7.88(s, 1H), 7.73(d, 1H), 7.44(d, 1H), 6.71(t, 1H), 3.86(s, 2H), 3.83(s, 3H), 2.10(s, 3H) |
| Ia.090 | —CH$_2$—SC$_2$H$_5$ | 7.88(s, 1H), 7.72(d, 1H), 7.44(d, 1H), 6.70(t, 1H), 3.88(s, 2H), 3.82(s, 3H), 2.46(q, 2H), 1.25(t, 3H) |
| Ia.091 | —CH$_2$—SCH$_2$—C$_2$H$_5$ | |
| Ia.092 | —CH$_2$—SCH$_2$—CO—OCH$_3$ | 7.89(s, 1H), 7.75(d, 1H), 7.46(d, 1H), 6.69(t, 1H), 4.00(s, 2H), 3.84(s, 3H), 3.75(s, 3H), 3.22(s, 2H) |
| Ia.093 | —CH$_2$—SCH$_2$—CO—OC$_2$H$_5$ | 7.89(s, 1H), 7.75(d, 1H), 7.46(d, 1H), 6.69(t, 1H), 4.20(q, 2H), 4.00(s, 2H), 3.82(s, 3H), 3.19(s, 2H), 1.30(t, 3H) |
| Ia.094 | —CH$_2$—N(CH$_3$)$_2$ | |
| Ia.095 | —COOH | 178–180° C. |
| Ia.096 | —CO—OCH$_3$ | 84–85° C. |
| Ia.097 | —CO—OC$_2$H$_5$ | |
| Ia.098 | —CO—OCH$_2$—C$_2$H$_5$ | 8.31(s, 1H), 7.94(d, 1H), 7.51(d, 1H), 6.71(t, 1H), 5.31(m, 1H), 3.89(s, 3H), 1.42(d, 6H) |
| Ia.099 | —CO—OCH(CH$_3$)$_2$ | |
| Ia.100 | —CO—(CH$_2$)$_3$—CH$_3$ | |
| Ia.101 | —CO—OCH(CH$_3$)—C$_2$H$_5$ | |
| Ia.102 | —CO—OCH$_2$—CH(CH$_3$)$_2$ | |
| Ia.103 | —CO—O—(CH$_2$)$_4$—CH$_3$ | |
| Ia.104 | —CO—OCH$_2$—CH$_2$—OCH$_3$ | |
| Ia.105 | —CO—OCH$_2$—CH$_2$—OC$_2$H$_5$ | |
| Ia.106 | —CHO | 102–104° C. |
| Ia.107 | —CH(OCH$_3$)$_2$ | 8.16(s, 1H), 7.80(d, 1H), 7.44(d, 1H), 6.70(t, 1H), 5.68(s, 1H), 3.85(s, 3H), 3.39(s, 6H) |
| Ia.108 | —CH(OC$_2$H$_5$)$_2$ | |

TABLE 1-continued

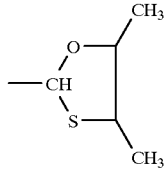

(R², R⁵ = Cl; R³ = CH₃;
Z—R⁴ = OCHF₂)

| No. | R¹ | m.p./MS [mz⁻¹]/ ¹H—NMR [ppm] |
|---|---|---|
| Ia.109 | —CH(OCH₂—C₂H₅)₂ | |
| Ia.110 | -(1,3-dioxolan-2-yl) | |
| Ia.111 | -(4-methyl-1,3-dioxolan-2-yl) | 8.23–8.16(m, 1H), 7.83 (d, 1H), 7.43(d, 1H), 6.70 (t, 1H), 6.38–6.22(m, 1H), 4.44–4.28(m, 2H), 3.81(s, 3H), 3.68–3.56 (m, 1H), 1.43–1.35(m, 3H) |
| Ia.112 | -(4-methyl-1,3-dithiolan-2-yl) | 8.58(d, 1H), 7.79(d, 1H), 7.51(d, 1H), 7.20(t, 1H), 6.12(s, 1H), 4.20–4.01 (m, 1H), 3.90(s, 3H), 3.65–3.46(m, 1H), 3.23–3.12(m, 1H), 1.59–1.48(m, 3H) |
| Ia.113 | -(4-vinyl-1,3-dioxolan-2-yl) | |
| Ia.114 | -(4,5-dimethyl-1,3-dioxolan-2-yl) | |
| Ia.115 | 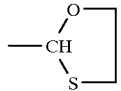 | |
| Ia.116 | 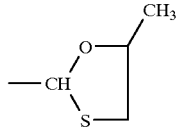 | |
| Ia.117 | 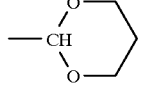 | |
| Ia.118 | 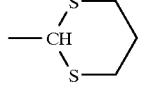 | |
| Ia.119 | | 8.24(s, 1H), 7.76(d, 1H), 7.44(d, 1H), 6.70(t, 1H), 5.68(s, 1H), 3.84(s, 3H), 3.22–2.90(m, 4H), 2.25–1.95(m, 2H) |
| Ia.120 | —CH=N—OH | |
| Ia.121 | —CH=N—OCH₃ | |
| Ia.122 | —CH=N—OC₂H₅ | 67–70° C. |
| Ia.123 | —CH=N—OCH₂—C₂H₅ | |
| Ia.124 | —CH=N—OCH(CH₃)₂ | |
| Ia.125 | —CH=N—OCH₂—CH₂—C₂H₅ | |
| Ia.126 | —CH=N—OCH₂—COOH | |

TABLE 1-continued $(R^2, R^5 = Cl; R^3 = CH_3;$
$Z-R^4 = OCHF_2)$

| No. | R¹ | m.p./MS [mz⁻¹]/ ¹H—NMR [ppm] |
|---|---|---|
| Ia.127 | —CH=N—OCH₂—CO—OCH₃ | |
| Ia.128 | —CH=N—OCH₂—CO—OC₂H₅ | |
| Ia.129 | —CH=N—OCH(CH₃)—CO—OH | |
| Ia.130 | —CH=N—OCH(CH₃)—CO—OCH₃ | |
| Ia.131 | —CH=N—OCH(CH₃)—OC₂H₅ | |
| Ia.132 | —NH—SO₂-(thiophen-2-yl) | |
| Ia.133 | —NH—SO₂-(thiophen-3-yl) | |
| Ia.134 | —NH—SO₂-(3-trifluoromethyl-phenyl) | |
| Ia.135 | —NH—SO₂—(2,6-dichlorophenyl) | |
| Ia.136 | —NH—SO₂—(4-chlorophenyl) | |
| Ia.137 | —NH—SO₂—(4-nitrophenyl) | |
| Ia.138 | —NH—SO₂—(5-chlorothiophen-2-yl) | |
| Ia.139 | —NH—CO—CH(Cl)—CH₂—Cl | 8.94(s, 1H), 7.68(d, 1H), 7.50(d, 1H), 7.28(s, 1H), 6.70(t, 1H), 4.81(t, 1H), 4.16–4.10(m, 2H), 3.82 (s, 3H) |
| Ia.140 | —NH—CO—CH₂—CH(CH₃)₂ | 8.90(s, 1H), 7.64(d, 1H), 7.55(d, 1H), 7.49(s, 1H), 6.70(t, 1H), 3.81(s, 3H), 2.32(d, 2H), 2.25(m, 1H), 1.05(d, 6H) |
| Ia.141 | —NH—CO—CH(CH₃)₂ | 9.00(s, 1H), 7.73(s, 1H), 7.55(d, 1H), 7.44(d, 1H), 6.68(t, 1H), 3.82(s, 3H), 2.62(m, 1H), 1.33(d, 6H) |
| Ia.142 | —NH—CO-cyclopropyl | 142° C. |
| Ia.143 | —CH₂—OH | 8.02(s, 1H), 7.78(d, 1H), 7.43(d, 1H), 6.71(t, 1H), 4.86(s, 2H), 3.83(s, 3H) |
| Ia.144 | —CH₂—OCH₂—CH=N—OCH₃ | |
| Ia.145 | —CH₂—OCH₂—C(CH₃)=N—OCH₃ | |
| Ia.146 | —CH₂—OCH(CH₃)—CH=N—OCH₃ | |
| Ia.147 | —CH₂—OCH₂—C(C₆H₅)=N—OCH₃ | |
| Ia.148 | —CH₂—O—CO—CH₃ | 7.93(s, 1H), 7.80(d, 1H), 7.46(d, 1H), 6.69(t, 1H), 5.27(s, 2H), 3.82(s, 3H), 2.18(s, 3H) |
| Ia.149 | —CO—OCH₂—CH=N—OCH₃ | 8.39(s, 1H), 7.94(d, 1H), 7.59–6.89(m, 1H), 7.51(d, 1H), 6.70(t, 1H), 5.12–4.91(m, 2H), 3.96–3.91(m, 3H), 3.82(s, 3H) |
| Ia.150 | —CO—OCH₂—C(CH₃)=N—OCH₃ | |
| Ia.151 | —CO—OCH(CH₃)—CH=N—OCH₃ | |
| Ia.152 | —CH=CH—CH=CH—CO—OC₂H₅ | |
| Ia.153 | —CH=CH—CH=CH—CO—NH—CH₃ | |
| Ia.154 | —CH=CH—COOH | |
| Ia.155 | —CH=CH—CO—OCH₃ | |
| Ia.156 | —CH=CH—CO—OC₂H₅ | 435[M]⁺, 362[M—COOC₂H₅]⁺ |
| Ia.157 | —CH=CH—CO—CH₃ | |
| Ia.158 | —CH=CH—CO—NH—CH₃ | |
| Ia.159 | —CH=CH—CO—N(CH₃)₂ | |
| Ia.160 | —CH=CH—CO—NH₂ | |
| Ia.161 | —CHBr₂ | 8.56(s, 1H), 7.79(d, 1H), 7.46(d, 1H), 7.15(d, 1H), 3.85(s, 3H) |
| Ia.162 | —H | 7.79(d, 2H), 7.43(d, 2H), 6.70(t, 1H), 3.85(s, 3H) |

TABLE 1-continued $(R^2, R^5 = Cl; R^3 = CH_3; Z—R^4 = OCHF_2)$

| No. | $R^1$ | m.p./MS $[mz^{-1}]$/ $^1H$—NMR [ppm] |
|---|---|---|
| Ia.163 | —CH$_2$—SCH(CH$_3$)$_2$ | 7.94(s, 1H), 7.71(d, 1H), 7.43(d, 1H), 6.71(t, 1H), 3.90(s, 2H), 3.82(s, 3H), 2.92(m, 1H), 1.33(d, 3H), 1.30(d, 3H) |
| Ia.164 | —CH$_2$—SCH(CH$_3$)—CH(CH$_3$)$_2$ | 7.91(s, 1H), 7.70(d, 1H), 7.40(d, 1H), 6.68(t, 1H), 3.89(s, 2H), 3.82(s, 3H), 2.71(m, 1H), 1.89(m, 1H), 1.22(d, 3H), 0.93(d, 6H) |
| Ia.165 | —CH$_2$—SCH$_2$—CH$_2$—OCH$_3$ | 7.92(s, 1H), 7.72(d, 1H), 7.44(d, 1H), 6.71(t, 1H), 3.93(s, 2H), 3.82(s, 3H), 3.57(t, 2H), 3.35(s, 3H), 2.69(t, 2H) |
| Ia.166 | —CH$_2$—SCH$_2$—CO—OCH(CH$_3$)$_2$ | 7.90(s, 1H), 7.73(d, 1H), 7.43(d, 1H), 6.68(t, 1H), 5.07(m, 1H), 4.02(s, 2H), 3.82(s, 3H), 3.15(s, 2H), 1.17(d, 6H) |
| Ia.167 | —CH$_2$—SO—C$_2$H$_5$ | 110–112° C. |
| Ia.168 | —CH$_2$—SO$_2$—C$_2$H$_5$ | 108–110° C. |
| Ia.169 | —SO$_3^-$ Na$^+$ | 8.48(s, 1H), 7.83(d, 1H), 7.54(d, 1H), 7.41(t, 1H), 3.80(s, 3H) |
| Ia.170 | —SO$_2$-(1-piperidyl) | |
| Ia.171 | —SO$_2$—NH-cyclopropyl | 120–123° C. |
| Ia.172 | —SO$_2$—NH—CH$_2$—CO—OCH$_3$ | 8.64(s, 1H), 8.08(d, 1H), 7.61(d, 1H), 6.71(t, 1H), 5.67(s, 1H), 3.89(d, 2H), 3.84(s, 3H), 3.67(s, 3H) |
| Ia.173 | —SO$_2$—NH—CH$_2$—CO—OC$_2$H$_5$ | 8.63(s, 1H), 8.06(d, 1H), 7.60(d, 1H), 6.72(t, 1H), 5.68(s, 1H), 4.11(q, 2H), 3.86(s, 2H), 3.80(s, 3H), 1.20(t, 3H) |
| Ia.174 | —SO$_2$—NH—CH(CH(CH$_3$)$_2$)—CO—OC$_2$H$_5$ | 8.61(d, 1H), 8.44(s, 1H), 8.05(d, 1H), 7.78(d, 1H), 7.49(t, 1H), 3.84(s, 3H), 3.79(q, 2H), 3.54(m, 1H), 1.98(m, 1H), 1.00(t, 3H), 0.90(d, 3H), 0.80(d, 3H) |
| Ia.175 | —SO$_2$—NH—CH(CH(CH$_3$)$_2$)—CO—OCH$_3$ | 82–84° C. |
| Ia.176 | —SO$_2$—NH—CH(CH$_3$)—CO—OC$_2$H$_5$ | 93° C. |
| Ia.177 | —SO$_2$—NH—CH(CH$_2$CH(CH$_3$)$_2$)—CO—OCH$_3$ | 499[M]$^+$, 440[M—COOCH$_3$]$^+$ |
| Ia.178 | —SO$_2$—NH—CH(4-chlorophenyl-methyl)—CO—OC$_2$H$_5$ | 8.30(s, 1H), 8.01(d, 1H), 7.53(d, 1H), 7.40(t, 1H), 7.20(s, 4H), 4.10(m, 1H), 3.88(q, 2H), 3.80(s, 3H), 3.05–2.88(m, 2H), 1.01(t, 3H) |
| Ia.179 | —SO$_2$—NH-(tetrahydro-furan-2-on-3-yl) | 72–74° C. |
| Ia.180 | —SO$_2$—N(CH$_3$)—CH$_2$—CO—OC$_2$H$_5$ | 471[M]$^+$, 398[M—COOC$_2$H$_5$]$^+$ |
| Ia.181 | —SO$_2$—N(CH$_3$)—CH$_2$—CO—OCH$_3$ | 8.66(s, 1H), 8.02(d, 1H), 7.58(d, 1H), 6.71(t, 1H), 4.19(s, 3H), 3.82(s, 2H); 3.70(s, 3H), 3.02(s, 3H) |
| Ia.182 | —SO$_2$-(2-methoxycarbonyl-pyrrolidin-1-yl) | 8.65(s, 1H), 8.01(d, 1H), 7.59(d, 1H), 6.70(t, 1H), 4.63(m, 1H), 3.84(s, 3H), |

TABLE 1-continued

[Structure: 3-(4-chloro-3-R¹-phenyl)-4-chloro-5-(difluoromethoxy)-1-methyl-pyrazole]

($R^2, R^5$ = Cl; $R^3$ = $CH_3$;
Z—$R^4$ = $OCHF_2$)

| No. | R¹ | m.p./MS [mz⁻¹]/ ¹H—NMR [ppm] |
|---|---|---|
| Ia.183 | —SO₂-(2-ethoxycarbonyl-piperid-1-yl) | 3.71(m, 2H), 3.62(s, 3H), 3.47(m, 2H), 2.75(m, 2H) 8.68(s, 1H), 8.00(d, 1H), 7.55(d, 1H), 6.80(t, 1H), 4.80–3.76(m, 2H), 4.10 (q, 2H), 3.84(s, 3H), 3.40 (t, 1H), 2.25—1.81(m, 2H), 1.68(m, 2H), 1.45–1.30 (m, 2H), 1.21(t, 3H) |
| Ia.184 | —SO₂—N(CH₃)—CH₂—CO—NH(CH₃) | 77–79° C. |
| Ia.185 | —SO₂—N(CH₃)—CH₂—CO—N(CH₃)₂ | 142° C. |
| Ia.186 | —NH—SO₂—C(CH₃)₂—Cl | 8.38(s, 1H), 7.62(d, 1H), 7.40(d, 1H), 7.05(s, 1H), 6.69(t, 1H), 3.81(s, 3H), 1.94(s, 6H) |
| Ia.187 | —N(SO₂—C(CH₃)₂—Cl)₂ | |
| Ia.188 | —N(SO₂-(3,5-dimethyl-isoxazol-4-yl))₂ | 144–146° C. |
| Ia.189 | —NH—NH₃⁺Cl⁻ | 150–152° C. |
| Ia.190 | —NH—NH—CO—OC₂H₅ | 7.43(s, 1H), 7.31(d, 1H) 7.29(d, 1H), 7.06(s, 1H) 6.67(t, 3H), 6.32(s, 1H), 4.18(q, 2H), 3.80(s, 3H), 1.25(t, 3H) |
| Ia.191 | —N=N—CO—OC₂H₅ | 8.18(s, 1H), 8.07(d, 1H), 7.66(d, 1H), 6.70(t, 1H), 4.53(q, 2H), 3.82(s, 3H), 1.50(t, 3H) |
| Ia.192 | [1,3-dioxolane with two CO—OC₂H₅ groups and CH] | 8.31(s, 1H), 7.77(d, 1H), 7.42(d, 1H), 6.68(t, 1H), 6.52(s, 1H), 5.03(s, 1H), 4.88(s, 1H), 4.38(q, 2H), 4.25(q, 2H), 3.81(s, 3H), 1.48(t, 3H), 1.24(t, 3H) |
| Ia.193 | —CH=CH—CH[1,3-dioxane-CH₃] | 8.13(s, 1H), 7.72(d, 1H), 7.40(d, 1H), 7.28–7.19 (m, 1H), 6.69(t, 1H), 6.37–6.25(m, 1H), 5.22 (d, 1H), 4.20(d, 1H), 3.98–3.85(m, 2H), 3.80 (s, 3H), 1.82–1.71(m, 1H), 1.58–1.47(m, 1H), 1.30 (d, 3H) |
| Ia.194 | —CH=CH—CO-(2-methoxycarbonyl-pyrrolidin-1-yl) | 8.25(s, 1H), 7.83(d, 1H), 7.80(m, 1H), 7.68(m, 1H) 7.40(t, 1H), 7.08(d, 1H), 4.43(m, 1H), 3.81(s, 3H), 3.80–3.45(m, 4H), 3.65(s, 3H), 2.30–2.15 (m, 2H) |
| Ia.195 | —CH=CH—P(O)(OH)₂ | |
| Ia.196 | —CH=CH—P(O)(OC₂H₅)₂ | |
| Ia.197 | —CH₂—P(O)(OH)₂ | |
| Ia.198 | —CH₂—P(O)(OC₂H₅)₂ | 7.93(m, 1H), 7.75(m, 1H), 7.58(d, 1H), 7.37(t, 1H), 4.05–3.90(m, 4H), 3.80(s, 3H), 3.45(d, 2H), |

TABLE 1-continued

($R^2, R^5 = Cl$; $R^3 = CH_3$;
Z—$R^4$ = $OCHF_2$)

| No. | $R^1$ | m.p./MS [mz$^{-1}$]/ $^1$H—NMR [ppm] |
|---|---|---|
| | | 1.30–1.15(m, 6H) |
| Ia.199 | —P(O)(OH)$_2$ | |
| Ia.200 | —P(O)(OC$_2$H$_5$)$_2$ | |
| Ia.201 | —OCH$_2$—CO—OCH$_2$—CH=N—OCH$_3$ | |
| Ia.202 | —CO—OCH$_2$—CH=N—OCH$_2$—CH=CH$_2$ | |
| Ia.203 | —CO—OCH$_2$—CH=N—OCH$_2$—CH=CHCl | |
| Ia.204 | —CO—OCH$_2$—CH=N—OCH$_2$—CH$_2$—C$_2$H$_5$ | |
| Ia.205 | —CO—OCH$_2$—CH=N—OCH$_2$—phenyl | |
| Ia.206 | —CO—NH—CH$_2$—CO—OCH$_3$ | 8.22(s, 1H), 7.90(d, 1H), 7.48(d, 1H), 6.82(s, 1H), 6.70(t, 1H), 4.31(s, 2H), 3.89(s, 3H), 3.88(s, 3H) |
| Ia.207 | —CO—NH—CH(CH(CH$_3$)$_2$)—CO—OC$_2$H$_5$ | 8.20(s, 1H), 7.89(d, 1H), 7.49(d, 1H), 6.78(s, 1H), 6.69(t, 1H), 4.80(d, 1H), 4.26(q, 2H), 3.83(s, 3H), 2.35(m, 1H), 1.31(t, 3H), 1.08(d, 3H), 1.02(d, 3H) |
| Ia.208 | —CO—N(CH$_3$)—CH$_2$—CO—OCH$_3$ | 421[M]$^+$ |
| Ia.209 | —CO—N(CH$_3$)—CH$_2$—CO—OC$_2$H$_5$ | 435[M]$^+$, 362 [M—COOC$_2$H$_5$]$^+$, |
| Ia.210 | —C(SCH$_3$)=N—OH | |
| Ia.211 | —C(SCH$_3$)=N—OCH$_2$—CO—OC$_2$H$_5$ | |
| Ia.212 | —C(SCH$_3$)=N—O—CO—CH$_3$ | |
| Ia.213 | —C(CN)=N—OH | |
| Ia.214 | —C(CN)=N—OCH$_2$—CO—OC$_2$H$_5$ | |
| Ia.215 | —C(CN)=N—O—CO—CH$_3$ | |
| Ia.216 | —CO—NH-(tetrahydro-furan-2-on-3-yl) | 8.25(s, 1H), 7.94(d, 1H), 7.50(d, 1H), 6.88(s, 1H), 6.70(t, 1H), 4.77(m, 1H), 4.58(t, 1H), 4.38(m, 1H), 3.84(s, 3H), 3.32(m, 1H), 3.06(m, 1H) |
| Ia.217 | —Cl | 8.00(m, 1H), 7.73(m, 1H), 7.50(d, 1H), 6.68(t, 1H), 3.81(s, 3H) |
| Ia.218 | —Br | 8.16(m, 1H), 7.80(m, 1H), 7.50(d, 1H), 6.69(t, 1H), 3.82(s, 3H) |
| Ia.219 | —I | 93–95° C.; 8.37(s, 1H), 7.83(d, 1H), 7.48(d, 1H), 6.68(t, 1H), 3.83(s, 3H) |
| Ia.220 | —CN | |
| Ia.221 | —CH=CH—CO—CH(OCH$_3$)$_2$ | |
| Ia.222 | —CH=CH—CO—CH(OC$_2$H$_5$)$_2$ | 8.29–8.21(m, 2H), 7.84 (m, 1H), 7.48(d, 1H), 7.20 –7.13(m, 1H), 6.68(t, 1H), 4.88(s, 1H), 3.86(s, 3H), 3.80–3.61(m, 4H), 1.30–1.20(m, 6H) |
| Ia.223 | —CH=CH—CO—CH(1,3-dioxan-2-yl) | |

TABLE 1-continued (R², R⁵ = Cl; R³ = CH₃; Z—R⁴ = OCHF₂)

| No. | R¹ | m.p./MS [mz⁻¹]/ ¹H—NMR [ppm] |
|---|---|---|
| Ia.224 | —CH=CH—CO—CH(OCH₂CH₂CH₂O) (1,3-dioxane) | |
| Ia.225 | —O—CO—CH₃ | |
| Ia.226 | —O—CO—C₂H₅ | |
| Ia.227 | —O—CO—CH₂-phenyl | |
| Ia.228 | —O—CO-cyclohexyl | |
| Ia.229 | —O—CO—CH₂—OCH₃ | |
| Ia.230 | —O—CO—NH—CH₃ | |
| Ia.231 | —O—CO—N(CH₃)₂ | |
| Ia.232 | —O—CONH-phenyl | |
| Ia.233 | —O—CO—NH—C₂H₅ | |
| Ia.234 | —O—CO—N(C₂H₅)₂ | |
| Ia.235 | —O—CO—NH₂ | |
| Ia.236 | —O—CS—N(CH₃)₂ | |
| Ia.237 | —O—CS—N(C₂H₅)₂ | |
| Ia.238 | —O—CS—NH₂ | |
| Ia.239 | —CO—NH—CH₃ | |
| Ia.240 | —CO—NH—C₂H₅ | |
| Ia.241 | —CO—NH—CH₂—C₂H₅ | |
| Ia.242 | —CO—NH—CH(CH₃)₂ | |
| Ia.243 | —CO—NH—CH₂—CH₂—C₂H₅ | |
| Ia.244 | —CO—N(CH₃)₂ | |
| Ia.245 | —CO—N(C₂H₅)₂ | |
| Ia.246 | —CO—N(pyrrolidine) | |
| Ia.247 | —CO—N(piperidine) | |
| Ia.248 | —CO—N(morpholine) | |

TABLE 2

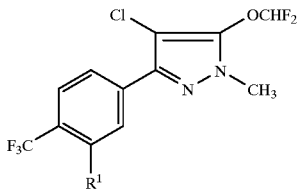

I ($R^2$ = $CF_3$; $R^3$ = $CH_3$; Z-$R^4$ = $OCHF_2$; $R^5$ = Cl)

| No. | $R^1$ | m.p./MS [mz$^{-1}$]/ $^1$H—NMR [ppm] |
|---|---|---|
| Ia.001 | —OCH$_3$ | |
| Ia.002 | —OC$_2$H$_5$ | |
| Ia.003 | —OCH$_2$—C$_2$H$_5$ | |
| Ia.004 | —OCH(CH$_3$)$_2$ | |
| Ia.005 | —OCH$_2$—CH$_2$—C$_2$H$_5$ | |
| Ia.006 | —OCH(CH$_3$)—C$_2$H$_5$ | |
| Ia.007 | —OCH$_2$—CH(CH$_3$)$_2$ | |
| Ia.008 | —OCH$_2$—CH$_2$—CH$_2$—C$_2$H$_5$ | |
| Ia.009 | —OCH$_2$—CH=CH$_2$ | |
| Ia.010 | —OCH$_2$—CH=CHCl | |
| Ia.011 | —OCH$_2$—C≡CH | |
| Ia.012 | —OCH(CH$_3$)C≡CH | |
| Ia.013 | —OCH$_2$—CO—OCH$_3$ | |
| Ia.014 | —OCH$_2$—CO—OC$_2$H$_5$ | |
| Ia.015 | —OCH(CH$_3$)—CO—OCH$_3$ | |
| Ia.016 | —OCH(CH$_3$)—CO—OC$_2$H$_5$ | |
| Ia.017 | —O-cyclopentenyl | |
| Ia.018 | —OCH$_2$—CN | |
| Ia.019 | —OCH(CH$_3$)—CN | |
| Ia.020 | —OH | |
| Ia.021 | —OCH$_2$—CO—O—(CH$_2$)$_4$—CH$_3$ | |
| Ia.022 | —OCH(CH$_3$)—CO—O—(CH$_2$)$_4$—CH$_3$ | |
| Ia.023 | —OCH$_2$-phenyl | |
| Ia.024 | —SCH$_3$ | |
| Ia.025 | —SC$_2$H$_5$ | |
| Ia.026 | —SCH$_2$—C$_2$H$_5$ | |
| Ia.027 | —SCH(CH$_3$)$_2$ | |
| Ia.028 | —SCH$_2$—CH$_2$—C$_2$H$_5$ | |
| Ia.029 | —SCH(CH$_3$)—C$_2$H$_5$ | |
| Ia.030 | —SCH$_2$—CH(CH$_3$)$_2$ | |
| Ia.031 | —SCH$_2$—CH$_2$—CH$_2$—C$_2$H$_5$ | |
| Ia.032 | —SCH$_2$—CH=CH$_2$ | |
| Ia.033 | —SCH$_2$—CH=CH—Cl | |
| Ia.034 | —SCH$_2$—C≡CH | |
| Ia.035 | —SCH(CH$_3$)—C≡CH | |
| Ia.036 | —SCH$_2$—CO—OCH$_3$ | |
| Ia.037 | —SCH$_2$—CO—OC$_2$H$_5$ | |
| Ia.038 | —SCH(CH$_3$)—CO—OCH$_3$ | |
| Ia.039 | —SCH(CH$_3$)—CO—OC$_2$H$_5$ | |
| Ia.040 | —S-cyclopentyl | |
| Ia.041 | —SCH$_2$—CN | |
| Ia.042 | —SCH(CH$_3$)—CN | |
| Ia.043 | —SCH$_2$—CO—O—(CH$_2$)$_4$—CH$_3$ | |
| Ia.044 | —SCH(CH$_3$)—CO—O—(CH$_2$)$_4$—CH$_3$ | |
| Ia.045 | —SCH$_2$-phenyl | |
| Ia.046 | —SCH$_2$—(4-Cl-phenyl) | |
| Ia.047 | —SO$_2$—Cl | |
| Ia.048 | —SO$_2$—NH$_2$ | |
| Ia.049 | —SO$_2$—NH—CH$_3$ | |
| Ia.050 | —SO$_2$—N(CH$_3$)$_2$ | |
| Ia.051 | —SO$_2$—NH—C$_2$H$_5$ | |
| Ia.052 | —SO$_2$—N(CH$_3$)—C$_2$H$_5$ | |
| Ia.053 | —SO$_2$—N(C$_2$H$_5$)$_2$ | |
| Ia.054 | —SO$_2$—(pyrrolidin-1-yl) | |
| Ia.055 | —SO$_2$-(morpholin-4-yl) | |
| Ia.056 | —SO$_2$—NH-phenyl | |
| Ia.057 | —SO$_2$—N(CH$_3$)-phenyl | |
| Ia.058 | —SO$_2$—NH—CH$_2$-phenyl | |
| Ia.059 | —NO$_2$ | |
| Ia.060 | —NH$_2$ | |
| Ia.061 | —NH—SO$_2$—CH$_3$ | |
| Ia.062 | —N(SO$_2$—CH$_3$)$_2$ | |
| Ia.063 | —NH—SO$_2$—C$_2$H$_5$ | |
| Ia.064 | —N(SO$_2$—C$_2$H$_5$)$_2$ | |
| Ia.065 | —NH—SO$_2$—CH$_2$—C$_2$H$_5$ | |

TABLE 2-continued

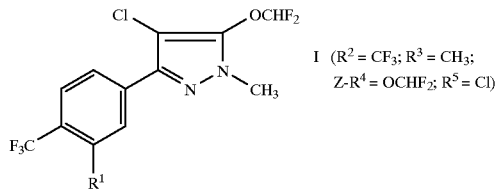

I ($R^2$ = $CF_3$; $R^3$ = $CH_3$; Z-$R^4$ = $OCHF_2$; $R^5$ = Cl)

| No. | $R^1$ | m.p./MS [mz$^{-1}$]/ $^1$H—NMR [ppm] |
|---|---|---|
| Ia.066 | —NH—CHO | |
| Ia.067 | —NH—CO—CH$_3$ | |
| Ia.068 | —NH—CO—C$_2$H$_5$ | |
| Ia.069 | —N(CO—CH$_3$)—SO$_2$—CH$_3$ | |
| Ia.070 | —N(CO—CH$_3$)—SO$_2$—C$_2$H$_5$ | |
| Ia.071 | —CH$_3$ | |
| Ia.072 | —CH=CH—CH$_3$ | |
| Ia.073 | —CH$_2$—Br | |
| Ia.074 | —CH$_2$—OCH$_3$ | |
| Ia.075 | —CH$_2$—OC$_2$H$_5$ | |
| Ia.076 | —CH$_2$—OCH$_2$—C$_2$H$_5$ | |
| Ia.077 | —CH$_2$—OCH(CH$_3$)$_2$ | |
| Ia.078 | —CH$_2$—O—(CH$_2$)$_3$—CH$_3$ | |
| Ia.079 | —CH$_2$—OCH(CH$_3$)—C$_2$H$_5$ | |
| Ia.080 | —CH$_2$—OCH$_2$—CH(CH$_3$)$_2$ | |
| Ib.081 | —CH$_2$—OCH$_2$—CH=CH$_2$ | |
| Ib.082 | —CH$_2$—OCH$_2$—C≡CH | |
| Ib.083 | —CH$_2$—OCH$_2$—CO—OCH$_3$ | |
| Ib.084 | —CH$_2$—OCH$_2$—CO—OC$_2$H$_5$ | |
| Ib.085 | —CH$_2$—OCH(CH$_3$)—CO—OCH$_3$ | |
| Ib.086 | —CH$_2$—OCH(CH$_3$)—CO—OC$_2$H$_5$ | |
| Ib.087 | —CH$_2$O-cyclopentyl | |
| Ib.088 | —CH$_2$—SCH$_3$ | |
| Ib.089 | —CH$_2$—SC$_2$H$_5$ | |
| Ib.090 | —CH$_2$—SCH$_2$—C$_2$H$_5$ | |
| Ib.091 | —CH$_2$—SCH$_2$—CO—OCH$_3$ | |
| Ib.092 | —CH$_2$—SCH$_2$—CO—OC$_2$H$_5$ | |
| Ib.093 | —CH$_2$—N(CH$_3$)$_2$ | |
| Ib.094 | —COOH | |
| Ib.095 | —CO—OCH$_3$ | |
| Ib.096 | —CO—OC$_2$H$_5$ | |
| Ib.097 | —CO—OCH$_2$—C$_2$H$_5$ | |
| Ib.098 | —CO—OCH(CH$_3$)$_2$ | |
| Ib.099 | —CO—O—(CH$_2$)$_3$—CH$_3$ | |
| Ib.100 | —CO—OCH(CH$_3$)—C$_2$H$_5$ | |
| Ib.101 | —CO—OCH$_2$—CH(CH$_3$)$_2$ | |
| Ib.102 | —CO—O—(CH$_2$)$_4$—CH$_3$ | |
| Ib.103 | —CO—OCH$_2$—CH$_2$—OCH$_3$ | |
| Ib.104 | —CO—OCH$_2$—CH$_2$—OC$_2$H$_5$ | |
| Ib.105 | —CHO | |
| Ib.106 | —CH(OCH$_3$)$_2$ | |
| Ib.107 | —CH(OC$_2$H$_5$)$_2$ | |
| Ib.108 | —CH(OCH$_2$—C$_2$H$_5$)$_2$ | |
| Ib.109 | —(1,3-Dioxolan-2-yl) | |
| Ib.110 | -(4-Methyl-1,3-dioxolan-2-yl) | |
| Ib.111 | -(4-Vinyl-1,3-dioxolan-2-yl) | |
| Ib.112 | -(4,5-Dimethyl-1,3-dioxolan-2-yl) | |
| Ib.113 | ![structure] | |
| Ib.114 | ![structure] | |

TABLE 2-continued

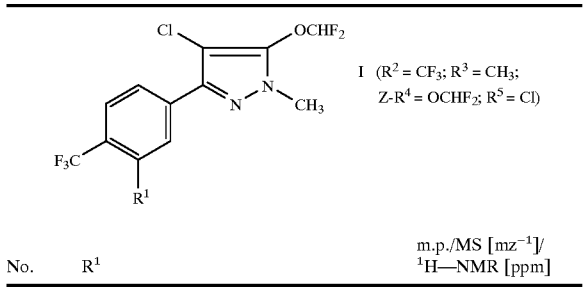

I (R² = CF₃; R³ = CH₃; Z-R⁴ = OCHF₂; R⁵ = Cl)

| No. | R¹ | m.p./MS [mz⁻¹]/ ¹H—NMR [ppm] |
|---|---|---|
| Ib.115 | (4-methyl-1,3-oxathiolan-2-yl) | |
| Ib.116 | (1,3-dioxan-2-yl) | |
| Ib. 117 | (1,3-dithian-2-yl) | |
| Ib.118 | —CH=N—OH | |
| Ib.119 | —CH=N—OCH₃ | |
| Ib.120 | —CH=N—OC₂H₅ | |
| Ib.121 | —CH=N—OCH₂—C₂H₅ | |
| Ib.122 | —CH=N—OCH(CH₃)₂ | |
| Ib.123 | —CH=N—OCH₂—CH₂—C₂H₅ | |
| Ib.124 | —CH=N—OCH₂—COOH | |
| Ib.125 | —CH=N—OCH₂—CO—OCH₃ | |
| Ib.126 | —CH=N—OCH₂—CO—OC₂H₅ | |
| Ib.127 | —CH=N—OCH(CH₃)—CO—OH | |
| Ib.128 | —CH=N—OCH(CH₃)—CO—OCH₃ | |
| Ib.129 | —CH=N—OCH(CH₃)—OC₂H₅ | |
| Ib.130 | —NH—SO₂-(thiophen-2-yl) | |
| Ia.131 | —NH—SO₂-(thiophen-3-yl) | |
| Ia.132 | —NH—SO₂-(3-trifluoromethylphenyl) | |
| Ia.133 | —NH—SO₂-(2,6-dichlorophenyl) | |
| Ib.134 | —NH—SO₂-(4-chlorophenyl) | |
| Ib.135 | —NH—SO₂-(4-nitrophenyl) | |
| Ib.136 | —NH—SO₂-(5-chlorothiophen-2-yl) | |
| Ib.137 | —CH₂—OCH₂—CH=N—OCH₃ | |
| Ib.138 | —CH₂—OCH₂—C(CH₃)=N—OCH₃ | |
| Ib.139 | —CH₂—OCH(CH₃)—CH=N—OCH₃ | |
| Ib.140 | —CH₂—OCH₂—C(C₆H₅)=N—OCH₃ | |
| Ib.141 | —CO—OCH₂—CH=N—OCH₃ | |
| Ib.142 | —CO—OCH₂—C(CH₃)=N—OCH₃ | |
| Ib.143 | —CO—OCH(CH₃)—CH=N—OCH₃ | |
| Ib.144 | —CH=CH—CH=CH—CO—OC₂H₅ | |
| Ib.145 | —CH=CH—CH=CH—CO—NH—CH₃ | |
| Ib.146 | —CH=CH—COOH | |
| Ib.147 | —CH=CH—OCH₃ | |
| Ib.148 | —CH=CH—CO—OC₂H₅ | |
| Ib.149 | —CH=CH—CO—CH₃ | |
| Ib.150 | —CH=CH—CO—NH—CH₃ | |
| Ib.151 | —CH=CH—CO—N(CH₃)₂ | |
| Ib.152 | —CH=CH—CO—NH₂ | |
| Ib.153 | —CHBr₂ | |
| Ib.154 | —H | 8.03(d, 2H), 7.70(d, 2H), 6.71(t, 1H), 3.85(s, 3H) |
| Ib.155 | —P(O)(OH)₂ | |
| Ib.156 | —P(O)(OC₂H₅)₂ | |
| Ib.157 | —CH₂—P(O)(OH)₂ | |

TABLE 2-continued

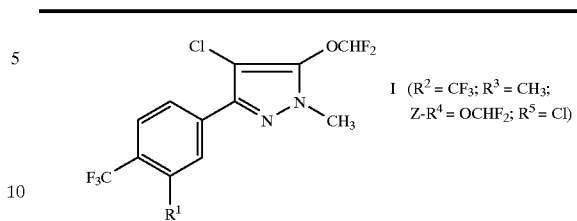

I (R² = CF₃; R³ = CH₃; Z-R⁴ = OCHF₂; R⁵ = Cl)

| No. | R¹ | m.p./MS [mz⁻¹]/ ¹H—NMR [ppm] |
|---|---|---|
| Ib.158 | —CH₂—P(O)(OC₂H₅)₂ | |
| Ib.159 | —CH=CH—P(O)(OH)₂ | |
| Ib.160 | —CH=CH—P(O)(OC₂H₅)₂ | |
| Ib.161 | —Cl | |
| Ib.162 | —Br | |
| Ib.163 | —I | |
| Ib.164 | —CN | |
| Ib.165 | —O—CO—CH₃ | |
| Ib.166 | —CO—N(CH₃)₂ | |

TABLE 3

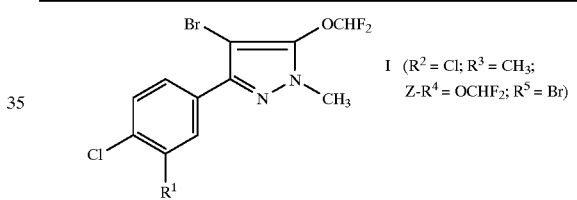

I (R² = Cl; R³ = CH₃; Z-R⁴ = OCHF₂; R⁵ = Br)

| No. | R¹ | m.p./MS [mz⁻¹]/ ¹H—NMR [ppm] |
|---|---|---|
| Ic.001 | —OCH₃ | |
| Ic.002 | —OCH₂—C≡CH | |
| Ic.003 | —SCH(CH₃)₂ | |
| Ic.004 | —SCH₂—C≡CH | |
| Ic.005 | —SO₂—Cl | |
| Ic.006 | —SO₂—NH—CH₃ | |
| Ic.007 | —NH—SO₂—CH₃ | |
| Ic.008 | —CH₃ | |
| Ic.009 | —CH₂Br | |
| Ic.010 | —CHBr₂ | |
| Ic.011 | —CH₂—OCH₃ | |
| Ic.012 | —CH₂—OCH₂—CH≡CH | |
| Ic.013 | —CHO | |
| Ic.014 | -(1,3-dioxolan-2-yl) | |
| Ic.015 | —CH=N—OC₂H₅ | |
| Ic.016 | —CH=CH—CO—OC₂H₅ | |
| Ic.017 | —NO₂ | |
| Ic.018 | —NH₂ | |
| Ic.019 | —H | |
| Ic.020 | —SO₂—CH₃ | |
| Ic.021 | —COOH | |
| Ic.022 | —CO—OC₂H₅ | |
| Ic.023 | —OCH₂—CO—OC₂H₅ | |
| Ic.024 | —P(O)(OH)₂ | |
| Ic.025 | —Cl | |
| Ic.026 | —Br | |
| Ic.027 | —CN | |
| Ic.028 | —O—CO—CH₃ | |
| Ic.029 | —CO—N(CH₃)₂ | |

TABLE 4

I ($R^2$ = Cl; $R^3$ = $CH_3$; Z-$R^4$ = $SCHF_2$; $R^5$ = Br)

[Structure: 3-(4-chloro-3-$R^1$-phenyl)-4-bromo-5-(difluoromethylthio)-1-methylpyrazole]

| No. | $R^1$ | m.p./MS [mz$^{-1}$]/ $^1$H—NMR [ppm] |
|---|---|---|
| Ic.001 | —$OCH_3$ | |
| Ic.002 | —$OCH_2$—C≡CH | |
| Ic.003 | —SCH($CH_3$)$_2$ | |
| Ic.004 | —$SCH_2$—C≡CH | |
| Ic.005 | —$SO_2$—Cl | |
| Ic.006 | —$SO_2$—NH—$CH_3$ | |
| Ic.007 | —NH—$SO_2$—$CH_3$ | |
| Ic.008 | —$CH_3$ | |
| Ic.009 | —$CH_2Br$ | |
| Ic.010 | —$CHBr_2$ | |
| Ic.011 | —$CH_2$—$OCH_3$ | |
| Ic.012 | —$CH_2$—$OCH_2$—CH≡CH | |
| Ic.013 | —CHO | |
| Ic.014 | -(1,3-dioxolan-2-yl) | |
| Ic.015 | —CH=N—$OC_2H_5$ | |
| Ic.016 | —CH=CH—CO—$OC_2H_5$ | |

TABLE 4-continued

I ($R^2$ = Cl; $R^3$ = $CH_3$; Z-$R^4$ = $SCHF_2$; $R^5$ = Br)

| No. | $R^1$ | m.p./MS [mz$^{-1}$]/ $^1$H—NMR [ppm] |
|---|---|---|
| Ic.017 | —$NO_2$ | |
| Ic.018 | —$NH_2$ | |
| Ic.019 | —H | |
| Ic.020 | —$SO_2$—$CH_3$ | |
| Ic.021 | —COOH | |
| Ic.022 | —CO—$OC_2H_5$ | |
| Ic.023 | —$OCH_2$—CO—$OC_2H_5$ | |
| Ic.024 | —P(O)(OH)$_2$ | |
| Ic.025 | —Cl | |
| Ic.026 | —Br | |
| Ic.027 | —CN | |
| Ic.028 | —O—CO—$CH_3$ | |
| Ic.029 | —CO—N($CH_3$)$_2$ | |

TABLE 5

I ($R^2$ = F; $R^3$ = $CH_3$; Z-$R^4$ = $OCHF_2$; $R^5$ = Cl)

| No. | $R^1$ | m.p./MS [mz$^{-1}$]/ $^1$H—NMR [ppm] |
|---|---|---|
| Ic.001 | —$OCH_3$ | |
| Ie.002 | —$OC_2H_5$ | |
| Ie.003 | —$OCH_2$—$C_2H5$ | |
| Ie.004 | —OCH($CH_3$)$_2$ | |
| Ie.005 | —$OCH_2$—$CH_2$—$C_2H_5$ | |
| Ie.006 | —OCH($CH_3$)—$C_2H_5$ | |
| Ie.007 | —$OCH_2$—CH($CH_3$)$_2$ | |
| Ie.008 | —$OCH_2$—$CH_2$—$CH_2$—$C_2H_5$ | |
| Ie.009 | —$OCH_2$—CH=$CH_2$ | |
| Ie.010 | —$OCH_2$—CH=CHCl | |
| Ie.011 | —$OCH_2$—C≡CH | |
| Ie.012 | —OCH($CH_3$)—C≡CH | |
| Ie.013 | —$OCH_2$—CO—$OCH_3$ | |
| Ie.014 | —$OCH_2$—CO—$OC_2H_5$ | |
| Ie.015 | —OCH($CH_3$)—CO—$OCH_3$ | |
| Ie.016 | —OCH($CH_3$)—CO—$C_2H_5$ | |
| Ie.017 | —O—cyclopentenyl | |
| Ie.018 | —$OCH_2$—CN | |
| Ie.019 | —OCH($CH_3$)—CN | |
| Ie.020 | —OH | |
| Ie.021 | —$OCH_2$—CO—O—$(CH_2)_4$—$CH_3$ | |
| Ie.022 | —OCH($CH_3$)—CO—O—$(CH_2)_4$—$CH_3$ | |
| Ie.023 | —$OCH_2$-phenyl | |
| Ie.024 | —$SCH_3$ | |
| Ie.025 | —$SC_2H_5$ | |
| Ie.026 | —$SCH_2$—$C_2H_5$ | |
| Ie.027 | —SCH($CH_3$)$_2$ | |
| Ie.028 | —$SCH_2$—$CH_2$—$C_2H_5$ | |

TABLE 5-continued

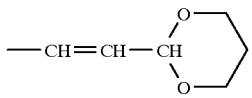

I ($R^2$ = F; $R^3$ = $CH_3$; Z-$R^4$ = $OCHF_2$; $R^5$ = Cl)

| No. | $R^1$ | m.p./MS [mz$^{-1}$]/ $^1$H—NMR [ppm] |
|---|---|---|
| Ie.029 | —SCH($CH_3$)—$C_2H_5$ | |
| Ie.030 | —S$CH_2$—CH($CH_3$)$_2$ | |
| Ie.031 | —S$CH_2$—$CH_2$—$CH_2$—$C_2H_5$ | |
| Ie.032 | —S$CH_2$—CH=$CH_2$ | |
| Ie.033 | —S$CH_2$—CH=CH—Cl | |
| Ie.034 | —S$CH_2$—C≡CH | |
| Ie.035 | —SCH($CH_3$)—C≡CH | |
| Ie.036 | —S$CH_2$—CO—O$CH_3$ | |
| Ie.037 | —S$CH_2$—CO—O$C_2H_5$ | |
| Ie.038 | —SCH($CH_3$)—CO—O$CH_3$ | |
| Ie.039 | —SCH($CH_3$)—CO—O$C_2H_5$ | |
| Ie.040 | —S-cyclopentyl | |
| Ie.041 | —S$CH_2$—CN | |
| Ie.042 | —SCH($CH_3$)—CN | |
| Ie.043 | —S$CH_2$—CO—O—($CH_2$)$_4$—$CH_3$ | |
| Ie.044 | —SCH($CH_3$)—CO—O—($CH_2$)$_4$—$CH_3$ | |
| Ie.045 | —S$CH_2$-phenyl | |
| Ie.046 | —S$CH_2$—(4-Cl-phenyl) | |
| Ie.047 | —$SO_2$—Cl | 8.53(m, 1H), 8.30(m, 1H), 7.40(t, 1H), 6.71(t, 1H), 3.84(s, 3H) |
| Ie.048 | —$SO_2$—$NH_2$ | |
| Ie.049 | —$SO_2$—NH—$CH_3$ | |
| Ie.050 | —$SO_2$—N($CH_3$)$_2$ | 8.40(m, 1H), 8.10(m, 1H), 7.28(m, 1H), 6.70(t, 1H), 3.82(s, 3H), 2.87(s, 6H) |
| Ie.051 | —$SO_2$—NH—$C_2H_5$ | |
| Ie.052 | —$SO_2$—N($CH_3$)—$C_2H_5$ | |
| Ie.053 | —$SO_2$—N($C_2H_5$)$_2$ | |
| Ie.054 | —$SO_2$-(pyrrolidin-1-yl) | |
| Ie.055 | —$SO_2$-(morpholin-4-yl) | |
| Ie.056 | —$SO_2$—NH-phenyl | |
| Ie.057 | —$SO_2$—N($CH_3$)-phenyl | |
| Ie.058 | —$SO_2$—NH—$CH_2$-phenyl | |
| Ie.059 | —$NO_2$ | 8.65(m, 1H), 8.19(m, 1H), 7.35(m, 1H), 6.71(t, 1H), 3.85(s, 3H) |
| Ie.060 | —$NH_2$ | 7.30–6.95(m, 3H), 6.65(t, 1H), 3.90–3.70(m, 5H) |
| Ie.061 | —NH—$SO_2$—$CH_3$ | |
| Ie.062 | —N($SO_2$—$CH_3$)$_2$ | |
| Ie.063 | —NH—$SO_2$—$C_2H_5$ | |
| Ie.064 | —N($SO_2$—$C_2H_5$)$_2$ | |
| Ie.065 | —NH—$SO_2$—$CH_2$—$C_2H_5$ | |
| Ie.066 | —NH—CHO | |
| Ie.067 | —NH—CO—$CH_3$ | 333[M]$^+$, 291[M—$C_2H_2O$]$^+$ |
| Ie.068 | —NH—CO—$C_2H_5$ | |
| Ie.069 | —N(CO—$CH_3$)—$SO_2$—$CH_3$ | |
| Ie.070 | —N(CO—$CH_3$)—$SO_2$—$C_2H_5$ | |
| Ie.071 | —$CH_3$ | |
| Ie.072 | —CH=CH—$CH_3$ | |
| Ie.073 | —CH=CH—CH(O—$CH_2$—$CH_2$—$CH_2$—O) (1,3-dioxane) | |
| Ie.074 | —$CH_2$—Br | |
| Ie.075 | —$CH_2$—O$CH_3$ | |
| Ie.076 | —$CH_2$—O$C_2H_5$ | |
| Ie.077 | —$CH_2$—O$CH_2$—$C_2H_5$ | |
| Ie.076 | —$CH_2$—OCH($CH_3$)$_2$ | |
| Ie.079 | —$CH_2$—O—($CH_2$)$_3$—$CH_3$ | |
| Ie.080 | —$CH_2$—OCH($CH_3$)—$C_2H_5$ | |
| Ie.081 | —$CH_2$—O$CH_2$—CH($CH_3$)$_2$ | |

TABLE 5-continued

I ($R^2$ = F; $R^3$ = $CH_3$; Z-$R^4$ = $OCHF_2$; $R^5$ = Cl)

| No. No. | $R^1$ | m.p./MS [mz$^{-1}$]/ $^1$H—NMR [ppm] |
|---|---|---|
| Ie.082 | —$CH_2$—$OCH_2$—CH=$CH_2$ | |
| Ie.083 | —$CH_2$—$OCH_2$—C≡CH | |
| Ie.084 | —$CH_2$—$OCH_2$—CO—$OCH_3$ | |
| Ie.085 | —$CH_2$—$OCH_2$—CO—$OC_2H_5$ | |
| Ie.086 | —$CH_2$—$OCH(CH_3)$—CO—$OCH_3$ | |
| Ie.087 | —$CH_2$—$OCH(CH_3)$—CO—$OC_2H_5$ | |
| Ie.088 | —$CH_2$—O—cyclopentyl | |
| Ie.089 | —$CH_2$—$OCH_3$ | |
| Ie.090 | —$CH_2$—$SC_2H_5$ | |
| Ie.091 | —$CH_2$—$SCH_2$—$C_2H_5$ | |
| Ie.092 | —$CH_2$—$SCH_2$—CO—$OCH_3$ | |
| Ie.093 | —$CH_2$—$SCH_2$—CO—$OC_2H_5$ | |
| Ie.094 | —$CH_2$—$N(CH_3)_2$ | |
| Ie.095 | —COOH | |
| Ie.096 | —CO—$OCH_3$ | |
| Ie.097 | —CO—$OC_2H_5$ | |
| Ie.098 | —CO—$OCH_2$—$C_2H_5$ | |
| Ie.099 | —CO—$OCH(CH_3)_2$ | |
| Ie.100 | —CO—O—$(CH_2)_3$—$CH_3$ | |
| Ie.101 | —CO—$OCH(CH_3)$—$C_2H_5$ | |
| Ie.102 | —CO—$OCH_2$—$CH(CH_3)_2$ | |
| Ie.103 | —CO—$O(CH_2)_4$—$CH_3$ | |
| Ie.104 | —CO—$OCH_2$—$CH_2$—$OCH_3$ | |
| Ie.105 | —CO—$OCH_2$—$CH_2$—$OC_2H_5$ | |
| Ie.106 | —CHO | |
| Ie.107 | —$CH(OCH_3)_2$ | |
| Ie.108 | —$CH(OC_2H_5)_2$ | |
| Ie.109 | —$CH(OCH_2$—$C_2H_5)_2$ | |
| Ie.110 | -(1,3-dioxolan-2-yl) | |
| Ie.111 | -(4-methyl-1,3-dioxolan-2-yl) | |
| Ie.112 | -(-4-methyl-1,3-dithiolan-2-yl) | |
| Ie.113 | -(4-vinyl-1,3-dioxolan-2-yl) | |
| Ie.114 | -(4,5-dimethyl-1,3-di-oxolan-2-yl) | |

Ie.115

Ie.116

Ie.117

Ie.118

TABLE 5-continued

Structure: pyrazole with Cl, OCHF$_2$, N-CH$_3$, and 4-fluorophenyl substituent bearing R$^1$; I (R$^2$ = F; R$^3$ = CH$_3$; Z-R$^4$ = OCHF$_2$; R$^5$ = Cl)

| No. | R$^1$ | m.p./MS [mz$^{-1}$]/ $^1$H—NMR [ppm] |
|---|---|---|
| Ie.119 | —CH(1,3-dithian-2-yl) (—CH with S—CH$_2$CH$_2$CH$_2$—S ring) | |
| Ie.120 | —CH=N—OH | |
| Ie.121 | —CH=N—OCH$_3$ | |
| Ie.122 | —CH=N—OC$_2$H$_5$ | |
| Ie.123 | —CH=N—OCH$_2$C$_2$H$_5$ | |
| Ie.124 | —CH=N—OCH(CH$_3$)$_2$ | |
| Ie.125 | —CH=N—OCH$_2$—CH$_2$—C$_2$H$_5$ | |
| Ie.126 | —CH=N—OCH$_2$—COOH | |
| Ie.127 | —CH=N—OCH$_2$—CO—OCH$_3$ | |
| Ie.128 | —CH=N—OCH$_2$—CO—OC$_2$H$_5$ | |
| Ie.129 | —CH=N—OCH(CH$_3$)—COOH | |
| Ie.130 | —CH=N—OCH(CH$_3$)—CO—OCH$_3$ | |
| Ie.131 | —CH=N—OCH(CH$_3$)—OC$_2$H$_5$ | |
| Ie.132 | —NH—SO$_2$-(thiophen-2-yl) | |
| Ie.133 | —NH—SO$_2$-(thiophen-3-yl) | |
| Ie.134 | —NH—SO$_2$-(3-trifluoromethylphenyl) | |
| Ie.135 | —NH—SO$_2$-(2,6-dichlorophenyl) | |
| Ie.136 | —NH—SO$_2$-(4-chlorophenyl) | |
| Ie.137 | —NH—SO$_2$-(4-nitrophenyl) | |
| Ie.138 | —NH—SO$_2$-(5-chlorothiophen-2-yl) | |
| Ie.139 | —NH—CO—CH(Cl)—CH$_2$—Cl | |
| Ie.140 | —NH—CO—CH$_2$—CH(CH$_3$)$_2$ | |
| Ie.141 | —NH—CO—CH(CH$_3$)$_2$ | |
| Ie.142 | —NH—CO—cyclopropyl | |
| Ie.143 | —CH$_2$—OH | |
| Ie.144 | —CH$_2$—OCH$_2$—CH=N—OCH$_3$ | |
| Ie.145 | —CH$_2$—OCH$_2$—C(CH$_3$)=N—OCH$_3$ | |
| Ie.146 | —CH$_2$—OCH(CH$_3$)—CH=N—OCH$_3$ | |
| Ie.147 | —CH$_2$—OCH$_2$—C(C$_6$H$_5$)=N—OCH$_3$ | |
| Ie.148 | —CH$_2$—O—CO—CH$_3$ | |
| Ie.149 | —CO—OCH$_2$—CH=N—OCH$_3$ | |
| Ie.150 | —CO—OCH$_2$—C(CH$_3$)=N—OCH$_3$ | |
| Ie.151 | —CO—OCH(CH$_3$)—CH=N—OCH$_3$ | |
| Ie.152 | —CH=CH—CH=CH—CO—OC$_2$H$_5$ | |
| Ie.153 | —CH=CH—CH=CH—CO—NH—CH$_3$ | |
| Ie.154 | —CH=CH—COOH | |
| Ie.155 | —CH=CH—CO—OCH$_3$ | |
| Ie.156 | —CH=CH—CO—OC$_2$H$_5$ | |
| Ie.157 | —CH=CH—CO—CH$_3$ | |
| Ie.158 | —CH=CH—CO—NH—CH$_3$ | |
| Ie.159 | —CH=CH—CO—N(CH$_3$)$_2$ | |
| Ie.160 | —CH=CH—CO—NH$_2$ | |
| Ie.161 | —CHBr$_2$ | |
| Ie.162 | —H | 7.90–7.80(m, 2H), 7.16–7.06 (m, 2H), 6.69(t, 1H), 3.81 (s, 3H) |
| Ie.163 | —CH$_2$—SCH(CH$_3$)$_2$ | |
| Ie.164 | —CH$_2$—SCH(CH$_3$)—CH(CH$_3$)$_2$ | |
| Ie.165 | —CH$_2$—SCH$_2$—CH$_2$—OCH$_3$ | |
| Ie.166 | —CH$_2$—SCH$_2$—CO—OCH(CH$_3$)$_2$ | |
| Ie.167 | —CH$_2$—SO—C$_2$H$_5$ | |
| Ie.168 | —CH$_2$—SO$_2$—C$_2$H$_5$ | |
| Ie.169 | —SO$_3^-$ Na$^+$ | |
| Ie.170 | —SO$_2$—(1-piperidyl) | |
| Ie.171 | —SO$_2$—NH-cyclopropyl | |
| Ie.172 | —SO$_2$—NH—CH$_2$—CO—OCH$_3$ | 8.41(m, 1H), 8.10(m, 1H), 7.28(m, 1h), 6.69(t, 1H), 5.50(s, 1H), 3.95(s, 2H), |

TABLE 5-continued

I ($R^2 = F$; $R^3 = CH_3$; Z-$R^4$ = OCHF$_2$; $R^5$ = Cl)

| No. No. | $R^1$ | m.p./MS [mz$^{-1}$]/ $^1$H—NMR [ppm] |
|---|---|---|
| | | 3.83(s, 3H), 3.70(s, 3H) |
| Ie.173 | —SO$_2$—NH—CH$_2$—CO—OC$_2$H$_5$ | |
| Ie.174 | —SO$_2$—NH—CH(CH(CH$_3$)$_2$)CO—OCH$_3$ | |
| Ie.175 | —SO$_2$—NH—CH(CH(CH$_3$)$_2$)CO—OC$_2$H$_5$ | 8.40(m, 1H), 8.07(m, 1H), 7.25(m, 1H), 6.69(T, 1H), 5.42(d, 1H), 4.26(m. 1H), 3.96–3.86(m, 2H), 3.81(s, 3H), 2.12(m, 1H), 1.04(t, 3H), 1.00(t, 3H), 0.89(t, 3H) |
| Ie.176 | —SO$_2$—NH—CH(CH$_3$)—CO—OC$_2$H$_5$ | |
| Ie.177 | —SO$_2$—NH—CH(CH$_2$CH(CH$_3$)$_2$)—CO—OCH$_3$ | |
| Ie.178 | —SO$_2$—NH—CH(4-chlorophenyl-methyl)-CO—OC$_2$H$_5$ | |
| Ie.179 | —SO$_2$—NH—(tetrahydrofuran-2-on-3-yl) | |
| Ie.180 | —SO$_2$—N(CH$_3$)—CH$_2$—CO—OC$_2$H$_5$ | 8.44(m, 1H), 8.09(m, 1H), 7.25(m, 1H), 6.70(t, 1H), 4.14(q, 2H), 3.84(s, 3H), 3.05(s, 3H), 1.22(t, 3H) |
| Ia.181 | —SO$_2$—N(CH$_3$)—CH$_2$—CO—OCH$_3$ | 8.26–8.10(m, 2H), 7.62(m, 1H) 7.38(t, 1H), 4.17(s, 2H), 3.82(s, 3H), 3.58(s, 3H), 2.94(s, 3H) |
| Ia.182 | —SO$_2$-(2-methoxycarbonyl-pyrrolidin-1-yl) | |
| Ia.183 | —SO$_2$-(2-ethoxycarbonyl-piperid-1-yl) | |
| Ia.184 | —SO$_2$—N(CH$_3$)—CH$_2$—CO—NH(CH$_3$) | |
| Ia.185 | —SO$_2$—N(CH$_3$)—CH$_2$—CO—N(CH$_3$)$_2$ | |
| Ia.186 | —NH—SO$_2$—C(CH$_3$)$_2$—Cl | |
| Ia.187 | —N(SO$_2$—C(CH$_3$)$_2$—Cl)$_2$ | |
| Ia.188 | —N(SO$_2$-(3,5-dimethylisox-azol-4-yl))$_2$ | |
| Ia.189 | —NH—NH$_3^+$ Cl$^-$ | |
| Ia.190 | —NH—NH—CO—OC$_2$H$_5$ | |
| Ia.191 | —N=N—CO—OC$_2$H$_5$ | |
| Ia.192 | (structure: —CH with two O linkages to CH groups bearing CO—OC$_2$H$_5$) | |
| Ia.193 | —CH=CH—CH (1,3-dioxane with CH$_3$) | |
| Ia.194 | —CH=CH—CO-(2-methoxycarbon-yl-pyrrolidin-1-yl) | |
| Ia.185 | —CH=CH—P(O)(OH)$_2$ | |
| Ia.196 | —CH=CH—P(O)(OC$_2$H$_5$)$_2$ | |
| Ia.197 | —CH$_2$—P(O)(OH)$_2$ | |
| Ia.198 | —CH$_2$—P(O)(OC$_2$H$_5$)$_2$ | |
| Ia.199 | —P(O)(OH)$_2$ | |
| Ia.200 | —P(O)(OC$_2$H$_5$)$_2$ | |
| Ia.201 | —OCH$_2$—CO—OCH$_2$—CH=N—OCH$_3$ | |
| Ia.202 | —CO—OCH$_2$—CH=N—OCH$_2$—CH=CH$_2$ | |

TABLE 5-continued

[Structure: 4-chloro-3-(4-fluoro-R¹-phenyl)-5-(difluoromethoxy)-1-methyl-pyrazole]

I ($R^2$ = F; $R^3$ = $CH_3$; Z-$R^4$ = $OCHF_2$; $R^5$ = Cl)

| No. No. | R¹ | m.p./MS [mz⁻¹]/ ¹H—NMR [ppm] |
|---|---|---|
| Ia.203 | —CO—OCH₂—CH=N—OCH₂—CH=CHCl | |
| Ia.204 | —CO—OCH₂—CH=N—N—OCH₂—CH₂—C₂H₅ | |
| Ia.205 | —CO—OCH₂—CH=N—OCH₂—phenyl | |
| Ia.206 | —CO—NH—CH₂—CO—OCH₃ | |
| Ia.207 | —CO—NH—CH(CH(CH₃)₂)—CO—OC₂H₅ | |
| Ia.208 | —CO—N(CH₃)—CH₂—CO—OCH₃ | |
| Ia.209 | —CO—N(CH₃)—CH₂—CO—OC₂H₅ | |
| Ia.210 | —C(SCH₃)=N—OH | |
| Ia.211 | —C(SCH₃)=N—OCH₂—CO—OC₂H₅ | |
| Ia.212 | —C(SCH₃)=N—O—CO—CH₃ | |
| Ia.213 | —C(CN)=N—OH | |
| Ia.214 | —C(CN)=N—OCH₂—CO—OC₂H₅ | |
| Ia.215 | —C(CN)=N—O—CO—CH₃ | |
| Ia.216 | —CO—NH-(tetrahydro-furan-2-on-3-yl) | |
| Ia.217 | —Cl | |
| Ia.218 | —Br | |
| Ia.219 | —I | |
| Ia.220 | —CN | |
| Ia.221 | —CH=CH—CO—CH(OCH₃)₂ | |
| Ia.222 | —CH=CH—CO—CH(OC₂H₅)₂ | |
| Ia.223 | —CH=CH—CO—CH(1,3-dioxolan-2-yl) | |
| Ia.224 | —CH=CH—CO—CH(1,3-dioxan-2-yl) | |
| Ia.225 | —O—CO—CH₃ | |
| Ia.226 | —O—CO—C₂H₅ | |
| Ia.227 | —O—CO—CH₂-phenyl | |
| Ia.228 | —O—CO-cyclohexyl | |
| Ia.229 | —O—CO—CH₂—OCH₃ | |
| Ia.230 | —O—CO—NH—CH₃ | |
| Ia.231 | —O—CO—N(CH₃)₂ | |
| Ia.232 | —O—CONH-phenyl | |
| Ia.233 | —O—CO—NH—C₂H₅ | |
| Ia.234 | —O—CO—N(C₂H₅)₂ | |
| Ia.235 | —O—CO—NH₂ | |
| Ia.236 | —O—CS—N(CH₃)₂ | |
| Ia.237 | —O—CS—N(C₂H₅)₂ | |
| Ia.238 | —O—CS—NH₂ | |
| Ia.239 | —CO—NH—CH₃ | |
| Ia.240 | —CO—NH—C₂H₅ | |
| Ia.241 | —CO—NH—CH₂—C₂H₅ | |
| Ia.242 | —CO—NH—CH(CH₃)₂ | |
| Ia.243 | —CO—NH—CH₂—CH₂—C₂H₅ | |
| Ia.244 | —CO—N(CH₃)₂ | |
| Ia.245 | —CO—N(C₂H₅)₂ | |
| Ia.246 | —CO—N(pyrrolidin-1-yl) | |

TABLE 5-continued

[Structure: 4-chloro-3-(4-fluoro-3-R¹-phenyl)-5-(difluoromethoxy)-1-methyl-1H-pyrazole]

I (R² = F; R³ = CH₃; Z-R⁴ = OCHF₂; R⁵ = Cl)

| No. No. | R¹ | m.p./MS [mz⁻¹]/ ¹H—NMR [ppm] |
|---|---|---|
| Ia.247 | —CO—N(piperidinyl) | |
| Ia.248 | —CO—N(morpholinyl) | |

TABLE 6

[Structure: 4-chloro-3-(4-cyano-3-R¹-phenyl)-5-(difluoromethoxy)-1-methyl-1H-pyrazole]

I (R² = CN; R³ = CH₃; Z—R⁴ = OCHF₂; R⁵ = Cl)

| No. | R¹ | m.p./MS [mz⁻¹]/ ¹H—NMR [ppm] |
|---|---|---|
| If.001 | —OCH₃ | 7.60(s, 1H), 7.59(s, 1H), 7.53(s, 1H), 6.69(t, 1H) 4.01(s, 3H), 3.86(s, 3H) |
| If.002 | —OC₂H₅ | |
| If.003 | —OCH₂—C₂H₅ | |
| If.004 | —OCH(CH₃)₂ | |
| If.005 | —OCH₂—CH₂—C₂H₅ | |
| If.006 | —OCH(CH₃)—C₂H₅ | |
| If.007 | —OCH₂—CH(CH₃)₂ | |
| If.008 | —OCH₂—CH₂—CH₂—C₂H₅ | |
| If.009 | —OCH₂—CH=CH₂ | |
| If.010 | —OCH₂—CH=CHCl | |
| If.011 | —OCH₂—C≡CH | 116–118° C. |
| If.012 | —OCH(CH₃)—C≡CH | |
| If.013 | —OCH₂—CO—OCH₃ | |
| If.014 | —OCH₂—CO—OC₂H₅ | 104–107° C. |
| If.015 | —OCH(CH₃)—CO—OCH₃ | |
| If.016 | —OCH(CH₃)—CO—OC₂H₅ | |
| If.017 | —O-cyclopentenyl | |
| If.018 | —OCH₂—CN | |
| If.019 | —OCH(CH₃)—CN | |
| If.020 | —OH | 163–166° C. |
| If.021 | —OCH₂—CO—O—(CH₂)₄—CH₃ | |
| If.022 | —OCH(CH₃)—CO—O—(CH₂)₄—CH₃ | |
| If.023 | —OCH₂-phenyl | |
| If.024 | —SCH₃ | |
| If.025 | —SC₂H₅ | |
| If.026 | —SCH₂—C₂H₅ | |
| If.027 | —SCH(CH₃)₂ | |
| If.028 | —SCH₂—CH₂—C₂H₅ | |
| If.029 | —SCH(CH₃)—C₂H₅ | |

TABLE 6-continued (R² = CN; R³ = CH₃;
Z—R⁴ = OCHF₂; R⁵ = Cl)

| No. | R¹ | m.p./MS [mz⁻¹]/ ¹H—NMR [ppm] |
|---|---|---|
| If.030 | —SCH₂—CH(CH₃)₂ | |
| If.031 | —SCH₂—CH₂—CH₂—C₂H₅ | |
| If.032 | —SCH₂—CH=CH₂ | |
| If.033 | —SCH₂—CH=CH—Cl | |
| If.034 | —SCH₂—C≡CH | |
| If.035 | —SCH(CH₃)—C≡CH | |
| If.036 | —SCH₂—CO—OCH₃ | |
| If.037 | —SCH₂—CO—OC₂H₅ | |
| If.038 | —SCH(CH₃)—CO—OCH₃ | |
| If.039 | —SCH(CH₃)—CO—OC₂H₅ | |
| If.040 | —S-cyclopentyl | |
| If.041 | —SCH₂—CN | |
| If.042 | —SCH(CH₃)—CN | |
| If.043 | —SCH₂—CO—O—(CH₂)₄—CH₃ | |
| If.044 | —SCH(CH₃)—CO—O—(CH₂)₄—CH₃ | |
| If.045 | —SCH₂-phenyl | |
| If.046 | —SCH₂—(4-Cl-phenyl) | |
| If.047 | —SO₂—Cl | |
| If.048 | —SO₂—NH₂ | |
| If.049 | —SO₂—NH—CH₃ | |
| If.050 | —SO₂—N(CH₃)₂ | |
| If.051 | —SO₂—NH—C₂H₅ | |
| If.052 | —SO₂—N(CH₃)—C₂H₅ | |
| If.053 | —SO₂—N(C₂H₅)₂ | |
| If.054 | —SO₂—(pyrrolidin-1-yl) | |
| If.055 | —SO₂-(morpholin-4-yl) | |
| If.056 | —SO₂-NH-phenyl | |
| If.057 | —SO₂—N(CH₃)-phenyl | |
| If.058 | —SO₂—NH—CH₂-phenyl | |
| If.059 | —NO₂ | 8.93(m, 1H), 8.41(m, 1H), 7.95(d, 1H), 6.71(t, 1H), 3.88(s, 3H) |
| If.060 | —NH₂ | |
| If.061 | —NH—SO₂—CH₃ | |
| If.062 | —N(SO₂—CH₃)₂ | |
| If.063 | —NH—SO₂—C₂H₅ | |
| If.064 | —N(SO₂—C₂H₅)₂ | |
| If.065 | —NH—SO₂—CH₂—C₂H₅ | |
| If.066 | —NH—CHO | |
| If.067 | —NH—CO—CH₃ | |
| If.068 | —NH—CO—C₂H₅ | |
| If.069 | —N(CO—CH₃)—SO₂—CH₃ | |
| If.070 | —N(CO—CH₃)—SO₂—C₂H₅ | |
| If.071 | —CH₃ | |
| If.072 | —CH=CH—CH₃ | |
| If.073 | —CH=CH—CH(—O—CH₂—CH₂—CH₂—O—) | |
| If.074 | —CH₂—Br | |
| If.075 | —CH₂—OCH₃ | |
| If.076 | —CH₂—OC₂H₅ | |
| If.077 | —CH₂—OCH₂—C₂H₅ | |
| If.078 | —CH₂—OCH(CH₃)₂ | |
| If.079 | —CH₂—O—(CH₂)₃—CH₃ | |
| If.080 | —CH₂—OCH(CH₃)—C₂H₅ | |
| If.081 | —CH₂—OCH₂—CH(CH₃)₂ | |
| If.082 | —CH₂—OCH₂—CH=CH₂ | |

TABLE 6-continued $(R^2 = CN; R^3 = CH_3;$
$Z-R^4 = OCHF_2; R^5 = Cl)$

| No. | R$^1$ | m.p./MS [mz$^{-1}$]/ $^1$H—NMR [ppm] |
|---|---|---|
| If.083 | —CH$_2$—OCH$_2$—C≡C—H | |
| If.084 | —CH$_2$—OCH$_2$—CO—OCH$_3$ | |
| If.085 | —CH$_2$—OCH$_2$—CO—OC$_2$H$_5$ | |
| If.086 | —CH$_2$—OCH(CH$_3$)—CO—OCH$_3$ | |
| If.087 | —CH$_2$—OCH(CH$_3$)—CO—OC$_2$H$_5$ | |
| If.088 | —CH$_2$—O-cyclopentyl | |
| If.089 | —CH$_2$—SCH$_3$ | |
| If.090 | —CH$_2$—SC$_2$H$_5$ | |
| If.091 | —CH$_2$—SCH$_2$—C$_2$H$_5$ | |
| If.092 | —CH$_2$—SCH$_2$—CO—OCH$_3$ | |
| If.093 | —CH$_2$—SCH$_2$—CO—OC$_2$H$_5$ | |
| If.094 | —CH$_2$—N(CH$_3$)$_2$ | |
| If.095 | —COOH | |
| If.096 | —CO—OCH$_3$ | |
| If.097 | —CO—OC$_2$H$_5$ | |
| If.098 | —CO—OCH$_2$—C$_2$H$_5$ | |
| If.099 | —CO—OCH(CH$_3$)$_2$ | |
| If.100 | —CO—O—(CH$_2$)$_3$—CH$_3$ | |
| If.101 | —CO—OCH(CH$_3$)—C$_2$H$_5$ | |
| If.102 | —CO—OCH$_2$—CH(CH$_3$)$_2$ | |
| If.103 | —CO—O—(CH$_2$)$_4$—CH$_3$ | |
| If.104 | —CO—OCH$_2$—CH$_2$—OCH$_3$ | |
| If.105 | —CO—OCH$_2$—CH$_2$—OC$_2$H$_5$ | |
| If.106 | —CHO | |
| If.107 | —CH(OCH$_3$)$_2$ | |
| If.108 | —CH(OC$_2$H$_5$)$_2$ | |
| If.109 | —CH(OCH$_2$—C$_2$H$_5$)$_2$ | |
| If.110 | -(1,3-dioxolan-2-yl) | |
| If.111 | -(4-methyl-1,3-dioxolan-2-yl) | |
| If.112 | -(4-methyl-1,3-dithiolan-2-yl) | |
| If.113 | -(4-vinyl-1,3-dioxolan-2-yl) | |
| If.114 | -(4,5-dimethyl-1,3-dioxolan-2-yl) | |

If.115

If.116

If.117

If.118

TABLE 6-continued ($R^2$ = CN; $R^3$ = $CH_3$;
Z—$R^4$ = $OCHF_2$; $R^5$ = Cl)

| No. | $R^1$ | m.p./MS [$mz^{-1}$]/ $^1H$—NMR [ppm] |
|---|---|---|
| If.119 | —CH(S—CH₂—CH₂—CH₂—S) (1,3-dithianyl) | |
| If.120 | —CH=N—OH | |
| If.121 | —CH=N—OCH₃ | |
| If.122 | —CH=N—OC₂H₅ | |
| If.123 | —CH=N—OCH₂—C₂H₅ | |
| If.124 | —CH=N—OCH(CH₃)₂ | |
| If.125 | —CH=N—OCH₂—CH₂—C₂H₅ | |
| If.126 | —CH=N—OCH₂—COOH | |
| If.127 | —CH=N—OCH₂—CO—OCH₃ | |
| If.128 | —CH=N—OCH₂—CO—OC₂H₅ | |
| If.129 | —CH=N—OCH(CH₃)—COOH | |
| If.130 | CH=N—OCH(CH₃)—CO—OCH₃ | |
| If.131 | —CH=N—OCH(CH₃)—OC₂H₅ | |
| If.132 | —NH—SO₂-(thiophen-2-yl) | |
| If.133 | —NH—SO₂-(thiophen-3-yl) | |
| If.134 | —NH—SO₂-(3-trifluoromethylphenyl) | |
| If.135 | —NH—SO₂—(2,6-dichlorophenyl) | |
| If.136 | —NH—SO₂—(4-chlorophenyl) | |
| If.137 | —NH—SO₂—(4-nitrophenyl) | |
| If.138 | —NH—SO₂—(5-chlorothiophen-2-yl) | |
| If.139 | —NH—CO—CH(Cl)—CH₂—Cl | |
| If.140 | —NH—CO—CH₂—CH(CH₃)₂ | |
| If.141 | —NH—CO—CH(CH₃)₂ | |
| If.142 | —NH—CO-cyclopropyl | |
| If.143 | —CH₂—OH | |
| If.144 | —CH₂—OCH₂—CH=N—OCH₃ | |
| If.145 | —CH₂—OCH₂—C(CH₃)=N—OCH₃ | |
| If.146 | —CH₂—OCH(CH₃)—CH=N—OCH₃ | |
| If.147 | —CH₂—OCH₂—C(C₆H₅)=N—OCH₃ | |
| If.148 | —CH₂—O—CO—CH₃ | |
| If.149 | —CO—OCH₂—CH=N—OCH₃ | |
| If.150 | —CO—OCH₂—C(CH₃)=N—OCH₃ | |
| If.151 | —CO—OCH(CH₃)—CH=N—OCH₃ | |
| If.152 | —CH=CH—CH=CH—CO—OC₂H₅ | |
| If.153 | —CH=CH—CH=CH—CO—NH—CH₃ | |
| If.154 | —CH=CH—COOH | |
| If.155 | —CH=CH—CO—OCH₃ | |
| If.156 | —CH=CH—CO—OC₂H₅ | |
| If.157 | —CH=CH—CO—CH₃ | |
| If.158 | —CH=CH—CO—NH—CH₃ | |
| If.159 | —CH=CH—CO—N(CH₃)₂ | |
| If.160 | —CH=CH—CO—NH₂ | |
| If.161 | —CHBr₂ | |
| If.162 | —H | |
| If.163 | —CH₂—SCH(CH₃)₂ | |
| If.164 | —CH₂—SCH(CH₃)—CH(CH₃)₂ | |
| If.165 | —CH₂—SCH₂—CH₂—OCH₃ | |
| If.166 | —CH₂—SCH₂—CO—OCH(CH₃)₂ | |
| If.167 | —CH₂—SO—C₂H₅ | |
| If.168 | —CH₂—SO₂—C₂H₅ | |
| If.169 | —SO₃⁻Na⁺ | |
| If.170 | —SO₂-(1-piperidyl) | |
| If.171 | —SO₂—NH-cyclopropyl | |
| If.172 | —SO₂—NH—CH₂—CO—OCH₃ | |
| If.173 | —SO₂—NH—CH₂—CO—OC₂H₅ | |

TABLE 6-continued $(R^2 = CN; R^3 = CH_3; Z-R^4 = OCHF_2; R^5 = Cl)$

| No. | $R^1$ | m.p./MS $[mz^{-1}]$/ $^1H$—NMR [ppm] |
|---|---|---|
| If.174 | —SO$_2$—NH—CH(CH(CH$_3$)$_2$)CO—OCH$_3$ | |
| If.175 | —SO$_2$—NH—CH(CH(CH$_3$)$_2$)CO—OC$_2$H$_5$ | |
| If.176 | —SO$_2$—NH—CH(CH$_3$)—CO—OC$_2$H$_5$ | |
| If.177 | —SO$_2$—NH—CH(CH$_2$CH(CH$_3$)$_2$)—CO—OCH$_3$ | |
| If.178 | —SO$_2$—NH—CH(4-chlorophenyl-methyl)—CO—OC$_2$H$_5$ | |
| If.179 | —SO$_2$—NH-(tetrahydrofuran-2-on-3-yl) | |
| If.180 | —SO$_2$—N(CH$_3$)—CH$_2$—CO—OC$_2$H$_5$ | |
| If.181 | —SO$_2$—N(CH$_3$)—CH$_2$—CO—OCH$_3$ | |
| If.182 | —SO$_2$-(2-methoxycarbonyl-pyrrolidin-1-yl) | |
| If.183 | —SO$_2$-(2-ethoxycarbonyl-piperid-1-yl) | |
| If.184 | —SO$_2$—N(CH$_3$)—CH$_2$—CO—NH(CH$_3$) | |
| If.185 | —SO$_2$—N(CH$_3$)—CH$_2$—CO—N(CH$_3$)$_2$ | |
| If.186 | —NH—SO$_2$—C(CH$_3$)$_2$—Cl | |
| If.187 | —N(SO$_2$—C(CH$_3$)$_2$—Cl)$_2$ | |
| If.188 | —N(SO$_2$-(3,5-dimethyl-isoxazol-4-yl))$_2$ | |
| If.189 | —NH—NH$_3^+$Cl$^-$ | |
| If.190 | —NH—NH—CO—OC$_2$H$_5$ | |
| If.191 | —N=N—CO—OC$_2$H$_5$ | |
| If.192 | (structure) | |
| If.193 | (structure) | |
| If.194 | —CH=CH—CO-(2-methoxycarbonylpyrrolidin-1-yl) | |
| If.195 | —CH=CH—P(O)(OH)$_2$ | |
| If.196 | —CH=CH—P(O)(OC$_2$H$_5$)$_2$ | |
| If.197 | —CH$_2$—P(O)(OH)$_2$ | |
| If.198 | —CH$_2$—P(O)(OC$_2$H$_5$)$_2$ | |
| If.199 | —P(O)(OH)$_2$ | |
| If.200 | —P(O)(OC$_2$H$_5$)$_2$ | |
| If.201 | —OCH$_2$—CO—OCH$_2$—CH=N—OCH$_3$ | |
| If.202 | —CO—OCH$_2$—CH=N—OCH$_2$—CH=CH$_2$ | |
| If.203 | —CO—OCH$_2$—CH=N—OCH$_2$—CH=CHCl | |
| If.204 | —CO—OCH$_2$—CH=N—N—OCH$_2$—CH$_2$—C$_2$H$_5$ | |
| If.205 | —CO—OCH$_2$—CH=N—OCH$_2$—phenyl | |
| If.206 | —CO—NH—CH$_2$—CO—OCH$_3$ | |
| If.207 | —CO—NH—CH(CH(CH$_3$)$_2$)—CO—OC$_2$H$_5$ | |
| If.208 | —CO—N(CH$_3$)—CH$_2$—CO—OCH$_3$ | |
| If.209 | —CO—N(CH$_3$)—CH$_2$—CO—OC$_2$H$_5$ | |
| If.210 | —C(SCH$_3$)=N—OH | |

TABLE 6-continued

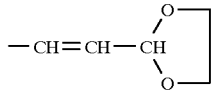

($R^2$ = CN; $R^3$ = CH$_3$;
Z—$R^4$ = OCHF$_2$; $R^5$ = Cl)

| No. | $R^1$ | m.p./MS [mz$^{-1}$]/ $^1$H—NMR [ppm] |
|---|---|---|
| If.211 | —C(SCH$_3$)=N—OCH$_2$—CO—OC$_2$H$_5$ | |
| If.212 | —C(SCH$_3$)=N—O—CO—CH$_3$ | |
| If.213 | —C(CN)=N—OH | |
| If.214 | —C(CN)=N—OCH$_2$—CO—OC$_2$H$_5$ | |
| If.215 | —C(CN)=N—O—CO—CH$_3$ | |
| If.216 | —CO—NH-(tetrahydro-furan-2-on-3-yl) | |
| If.217 | —Cl | 149–152° C. |
| If.218 | —Br | |
| If.219 | —I | |
| If.220 | —CN | |
| If.221 | —CH=CH—CO—CH(OCH$_3$)$_2$ | |
| If.222 | —CH=CH—CO—CH(OC$_2$H$_5$)$_2$ | |
| If.223 | 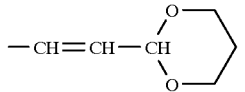 | |
| If.224 | | |
| If.225 | —O—CO—CH$_3$ | |
| If.226 | —O—CO—C$_2$H$_5$ | |
| If.227 | —O—CO—CH$_2$-phenyl | |
| If.228 | —O—CO-cyclohexyl | |
| If.229 | —O—CO—CH$_2$—OCH$_3$ | |
| If.230 | —O—CO—NH—CH$_3$ | |
| If.231 | —O—CO—N(CH$_3$)$_2$ | |
| If.232 | —O—CO—NH-phenyl | |
| If.233 | —O—CO—NH—C$_2$H$_5$ | |
| If.234 | —O—CO—N(C$_2$H$_5$)$_2$ | |
| If.235 | —O—CO—NH$_2$ | |
| If.236 | —O—CS—N(CH$_3$)$_2$ | |
| If.237 | —O—CS—N(C$_2$H$_5$)$_2$ | |
| If.238 | —O—CS—NH$_2$ | |

TABLE 7

($R^2$ = Br; $R^3$ = $CH_3$;
Z—$R^4$ = $OCHF_2$; $R^5$ = Cl)

| No. | $R^1$ | m.p./MS [mz$^{-1}$]/ $^1$H—NMR [ppm] |
|---|---|---|
| Ig.001 | —$OCH_3$ | |
| Ig.002 | —$OC_2H_5$ | |
| Ig.003 | —$OCH_2$—$C_2H_5$ | |
| Ig.004 | —$OCH(CH_3)_2$ | |
| Ig.005 | —$OCH_2$—$CH_2$—$C_2H_5$ | |
| Ig.006 | —$OCH(CH_3)$—$C_2H_5$ | |
| Ig.007 | —$OCH_2$—$CH(CH_3)_2$ | |
| Ig.008 | —$OCH_2$—$CH_2$—$CH_2$—$C_2H_5$ | |
| Ig.009 | —$OCH_2$—CH=$CH_2$ | |
| Ig.010 | —$OCH_2$—CH=CHCl | |
| Ig.011 | —$OCH_2$—C≡CH | |
| Ig.012 | —$OCH(CH_3)$C≡CH | |
| Ig.013 | —$OCH_2$—CO—$OCH_3$ | |
| Ig.014 | —$OCH_2$—CO—$OC_2H_5$ | |
| Ig.015 | —$OCH(CH_3)$—CO—$OCH_3$ | |
| Ig.016 | —$OCH(CH_3)$—CO—$OC_2H_5$ | |
| Ig.017 | —O-cyclopentenyl | |
| Ig.018 | —$OCH_2$—CN | |
| Ig.019 | —$OCH(CH_3)$—CN | |
| Ig.020 | —OH | |
| Ig.021 | —$OCH_2$—CO—O—$(CH_2)_4$—$CH_3$ | |
| Ig.022 | —$OCH(CH_3)$—CO—O—$(CH_2)_4$—$CH_3$ | |
| Ig.023 | —$OCH_2$-phenyl | |
| Ig.024 | —$SCH_3$ | |
| Ig.025 | —$SC_2H_5$ | |
| Ig.026 | —$SCH_2$—$C_2H_5$ | |
| Ig.027 | —$SCH(CH_3)_2$ | |
| Ig.028 | —$SCH_2$—$CH_2$—$C_2H_5$ | |
| Ig.029 | —$SCH(CH_3)$—$C_2H_5$ | |
| Ig.030 | —$SCH_2$—$CH(CH_3)_2$ | |
| Ig.031 | —$SCH_2$—$CH_2$—$CH_2$—$C_2H_5$ | |
| Ig.032 | —$SCH_2$—CH=$CH_2$ | |
| Ig.033 | —$SCH_2$—CH=CH—Cl | |
| Ig.034 | —$SCH_2$—C≡CH | |
| Ig.035 | —$SCH(CH_3)$—C≡CH | |
| Ig.036 | —$SCH_2$—CO—$OCH_3$ | |
| Ig.037 | —$SCH_2$—CO—$OC_2H_5$ | |
| Ig.038 | —$SCH(CH_3)$—CO—$OCH_3$ | |
| Ig.039 | —$SCH(CH_3)$—CO—$OC_2H_5$ | |
| Ig.040 | —S-cyclopentyl | |
| Ig.041 | —$SCH_2$—CN | |
| Ig.042 | —$SCH(CH_3)$—CN | |
| Ig.043 | —$SCH_2$—CO—O—$(CH_2)_4$—$CH_3$ | |
| Ig.044 | —$SCH(CH_3)$—CO—O—$(CH_2)_4$—$CH_3$ | |
| Ig.045 | —$SCH_2$-phenyl | |
| Ig.046 | —$SCH_2$—(4-Cl-phenyl) | |
| Ig.047 | —$SO_2$—Cl | |
| Ig.048 | —$SO_2$—$NH_2$ | |
| Ig.049 | —$SO_2$—NH—$CH_3$ | |
| Ig.050 | —$SO_2$—$N(CH_3)_2$ | |
| Ig.051 | —$SO_2$—NH—$C_2H_5$ | |
| Ig.052 | —$SO_2$—$N(CH_3)$—$C_2H_5$ | |
| Ig.053 | —$SO_2$—$N(C_2H_5)_2$ | |
| Ig.054 | —$SO_2$—(pyrrolidin-1-yl) | |
| Ig.055 | —$SO_2$-(morpholin-4-yl) | |
| Ig.056 | —$SO_2$-NH-phenyl | |
| Ig.057 | —$SO_2$—$N(CH_3)$-phenyl | |
| Ig.058 | —$SO_2$—NH—$CH_2$-phenyl | |
| Ig.059 | —$NO_2$ | |
| Ig.060 | —$NH_2$ | |
| Ig.061 | —NH—$SO_2$—$CH_3$ | |

TABLE 7-continued ($R^2$ = Br; $R^3$ = $CH_3$;
Z—$R^4$ = $OCHF_2$; $R^5$ = Cl)

| No. | $R^1$ | m.p./MS [$mz^{-1}$]/$^1$H—NMR [ppm] |
|---|---|---|
| Ig.062 | —N($SO_2$—$CH_3$)$_2$ | |
| Ig.063 | —NH—$SO_2$—$C_2H_5$ | |
| Ig.064 | —N($SO_2$—$C_2H_5$)$_2$ | |
| Ig.065 | —NH—$SO_2$—$CH_2$—$C_2H_5$ | |
| Ig.066 | —NH—CHO | |
| Ig.067 | —NH—CO—$CH_3$ | |
| Ig.068 | —NH—CO—$C_2H_5$ | |
| Ig.069 | —N(CO—$CH_3$)—$SO_2$—$CH_3$ | |
| Ig.070 | —N(CO—$CH_3$)—$SO_2$—$C_2H_5$ | |
| Ig.071 | —$CH_3$ | |
| Ig.072 | —CH=CH—$CH_3$ | |
| Ig.073 | —CH=CH—CH(O—$CH_2$—$CH_2$—O) (1,3-dioxan-2-yl ring) | |
| Ig.074 | —$CH_2$—Br | |
| Ig.075 | —$CH_2$—$OCH_3$ | |
| Ig.076 | —$CH_2$—$OC_2H_5$ | |
| Ig.077 | —$CH_2$—$OCH_2$—$C_2H_5$ | |
| Ig.078 | —$CH_2$—OCH($CH_3$)$_2$ | |
| Ig.079 | —$CH_2$—O—($CH_2$)$_2$—$C_2H_5$ | |
| Ig.080 | —$CH_2$—OCH($CH_3$)—$C_2H_5$ | |
| Ig.081 | —$CH_2$—$OCH_2$—CH($CH_3$)$_2$ | |
| Ig.082 | —$CH_2$—$OCH_2$—CH=$CH_2$ | |
| Ig.083 | —$CH_2$—$OCH_2$—C≡CH | |
| Ig.084 | —$CH_2$—$OCH_2$—CO—$OCH_3$ | |
| Ig.085 | —$CH_2$—$OCH_2$—CO—$OC_2H_5$ | |
| Ig.086 | —$CH_2$—OCH($CH_3$)—CO—$OCH_3$ | |
| Ig.087 | —$CH_2$—OCH($CH_3$)—CO—$OC_2H_5$ | |
| Ig.088 | —$CH_2$—O-cyclopentyl | |
| Ig.089 | —$CH_2$—$SCH_3$ | |
| Ig.090 | —$CH_2$—$SC_2H_5$ | |
| Ig.091 | —$CH_2$—$SCH_2$—$C_2H_5$ | |
| Ig.092 | —$CH_2$—$SCH_2$—CO—$OCH_3$ | |
| Ig.093 | —$CH_2$—$SCH_2$—CO—$OC_2H_5$ | |
| Ig.094 | —$CH_2$—N($CH_3$)$_2$ | |
| Ig.095 | —COOH | |
| Ig.096 | —CO—$OCH_3$ | |
| Ig.097 | —CO—$OC_2H_5$ | |
| Ig.098 | —CO—$OCH_2$—$C_2H_5$ | |
| Ig.099 | —CO—OCH($CH_3$)$_2$ | |
| Ig.100 | —CO—O—($CH_2$)$_2$—$C_2H_5$ | |
| Ig.101 | —CO—OCH($CH_3$)—$C_2H_5$ | |
| Ig.102 | —CO—$OCH_2$—CH($CH_3$)$_2$ | |
| Ig.103 | —CO—O—($CH_2$)$_4$—$CH_3$ | |
| Ig.104 | —CO—$OCH_2$—$CH_2$—$OCH_3$ | |
| Ig.105 | —CO—$OCH_2$—$CH_2$—$OC_2H_5$ | |
| Ig.106 | —CHO | |
| Ig.107 | —CH($OCH_3$)$_2$ | |
| Ig.108 | —CH($OC_2H_5$)$_2$ | |
| Ig.109 | —CH($OCH_2$—$C_2H_5$)$_2$ | |
| Ig.110 | -(1,3-dioxolan-2-yl) | |
| Ig.111 | -(4-methyl-1,3-dioxolan-2-yl) | |
| Ig.112 | -(4-methyl-1,3-dithiolan-2-yl) | |
| Ig.113 | -(4-vinyl-1,3-dioxolan-2-yl) | |
| Ig.114 | -(4,5-dimethyl-1,3-dioxolan-2-yl) | |

TABLE 7-continued

[Structure I: pyrazole with Cl at 4-position, OCHF$_2$ at 5-position, N-CH$_3$, 3-phenyl substituted with Br (para) and R$^1$ (meta)]

($R^2$ = Br; $R^3$ = CH$_3$;
Z—$R^4$ = OCHF$_2$; $R^5$ = Cl)

| No. | R$^1$ | m.p./MS [mz$^{-1}$]/ $^1$H—NMR [ppm] |
|---|---|---|
| Ig.115 | —CH(O—CH(CH$_3$)—S—)(cyclic, with CH$_3$ on carbons) | |
| Ig.116 | —CH(O—CH$_2$—S—)(cyclic) | |
| Ig.117 | —CH(O—CH(CH$_3$)—S—)(cyclic) | |
| Ig.118 | —CH(O—CH$_2$—CH$_2$—O—)(cyclic) | |
| Ig.119 | —CH(S—CH$_2$—CH$_2$—S—)(cyclic) | |
| Ig.120 | —CH=N—OH | |
| Ig.121 | —CH=N—OCH$_3$ | |
| Ig.122 | —CH=N—OC$_2$H$_5$ | |
| Ig.123 | —CH=N—OCH$_2$—C$_2$H$_5$ | |
| Ig.124 | —CH=N—OCH(CH$_3$)$_2$ | |
| Ig.125 | —CH=N—OCH$_2$—CH$_2$—C$_2$H$_5$ | |
| Ig.126 | —CH=N—OCH$_2$—COOH | |
| Ig.127 | —CH=N—OCH$_2$—CO—OCH$_3$ | |
| Ig.128 | —CH=N—OCH$_2$—CO—OC$_2$H$_5$ | |
| Ig.129 | —CH=N—OCH(CH$_3$)—COOH | |
| Ig.130 | —CH=N—OCH(CH$_3$)—CO—OCH$_3$ | |
| Ig.131 | —CH=N—OCH(CH$_3$)—OC$_2$H$_5$ | |
| Ig.132 | —NH—SO$_2$-(thiophen-2-yl) | |
| Ig.133 | —NH—SO$_2$-(thiophen-3-yl) | |
| Ig.134 | —NH—SO$_2$-(3-trifluoromethylphenyl) | |
| Ig.135 | —NH—SO$_2$—(2,6-dichlorophenyl) | |
| Ig.136 | —NH—SO$_2$—(4-chlorophenyl) | |
| Ig.137 | —NH—SO$_2$—(4-nitrophenyl) | |
| Ig.138 | —NH—SO$_2$—(5-chlorothiophen-2-yl) | |
| Ig.139 | —NH—CO—CH(Cl)—CH$_2$—Cl | |
| Ig.140 | —NH—CO—CH$_2$—CH(CH$_3$)$_2$ | |
| Ig.141 | —NH—CO—CH(CH$_3$)$_2$ | |
| Ig.142 | —NH—CO-cyclopropyl | |
| Ig.143 | —CH$_2$—OH | |

TABLE 7-continued (R² = Br; R³ = CH₃;
Z—R⁴ = OCHF₂; R⁵ = Cl)

| No. | R¹ | m.p./MS [mz⁻¹]/ $^1$H—NMR [ppm] |
|---|---|---|
| Ig.144 | —CH₂—OCH₂—CH=N—OCH₃ | |
| Ig.145 | —CH₂—OCH₂—C(CH₃)=N—OCH₃ | |
| Ig.146 | —CH₂—OCH(CH₃)—CH=N—OCH₃ | |
| Ig.147 | —CH₂—OCH₂—C(C₆H₅)=N—OCH₃ | |
| Ig.148 | —CH₂—O—CO—CH₃ | |
| Ig.149 | —CO—OCH₂—CH=N—OCH₃ | |
| Ig.150 | —CO—OCH₂—C(CH₃)=N—OCH₃ | |
| Ig.151 | —CO—OCH(CH₃)—CH=N—OCH₃ | |
| Ig.152 | —CH=CH—CH=CH—CO—OC₂H₅ | |
| Ig.153 | —CH=CH—CH=CH—CO—NH—CH₃ | |
| Ig.154 | —CH=CH—COOH | |
| Ig.155 | —CH=CH—CO—OCH₃ | |
| Ig.156 | —CH=CH—CO—OC₂H₅ | |
| Ig.157 | —CH=CH—CO—CH₃ | |
| Ig.158 | —CH=CH—CO—NH—CH₃ | |
| Ig.159 | —CH=CH—CO—N(CH₃)₂ | |
| Ig.160 | —CH=CH—CO—NH₂ | |
| Ig.161 | —CHBr₂ | |
| Ig.162 | —H | |
| Ig.163 | —CH₂—SCH(CH₃)₂ | |
| Ig.164 | —CH₂—SCH(CH₃)—CH(CH₃)₂ | |
| Ig.165 | —CH₂—SCH₂—CH₂—OCH₃ | |
| Ig.166 | —CH₂—SCH₂—CO—OCH(CH₃)₂ | |
| Ig.167 | —CH₂—SO—C₂H₅ | |
| Ig.168 | —CH₂—SO₂—C₂H₅ | |
| Ig.169 | —SO₃⁻Na⁺ | |
| Ig.170 | —SO₂-(1-piperidyl) | |
| Ig.171 | —SO₂—NH-cyclopropyl | |
| Ig.172 | —SO₂—NH—CH₂—CO—OCH₃ | |
| Ig.173 | —SO₂—NH—CH₂—CO—OC₂H₅ | |
| Ig.174 | —SO₂—NH—CH(CH(CH₃)₂)CO—OCH₃ | |
| Ig.175 | —SO₂—NH—CH(CH(CH₃)₂)CO—OC₂H₅ | |
| Ig.176 | —SO₂—NH—CH(CH₃)—CO—OC₂H₅ | |
| Ig.177 | —SO₂—NH—CH(CH₂CH(CH₃)₂)—CO—OCH₃ | |
| Ig.178 | —SO₂—NH—CH(4-chlorophenyl-methyl)—CO—OC₂H₅ | |
| Ig.179 | —SO₂—NH-(tetrahydrofuran-2-on-3-yl) | |
| Ig.180 | —SO₂—N(CH₃)—CH₂—CO—OC₂H₅ | |
| Ig.181 | —SO₂—N(CH₃)—CH₂—CO—OCH₃ | |
| Ig.182 | —SO₂-(2-methoxycarbonyl-pyrrolidin-1-yl) | |
| Ig.183 | —SO₂-(2-ethoxycarbonyl-piperid-1-yl) | |
| Ig.184 | —SO₂—N(CH₃)—CH₂—CO—NH(CH₃) | |
| Ig.185 | —SO₂—N(CH₃)—CH₂—CO—N(CH₃)₂ | |
| Ig.186 | —NH—SO₂—C(CH₃)₂—Cl | |
| Ig.187 | —N(SO₂—C(CH₃)₂—Cl)₂ | |
| Ig.188 | —N(SO₂-(3,5-dimethyl-isoxazol-4-yl))₂ | |
| Ig.189 | —NH—NH₃⁺Cl⁻ | |
| Ig.190 | —NH—NH—CO—OC₂H₅ | |
| Ig.191 | —N=N—CO—OC₂H₅ | |

TABLE 7-continued

[Structure I: pyrazole with Cl at position 4, OCHF$_2$ at position 5, N-CH$_3$, connected to phenyl with Br and R$^1$ substituents]

(R$^2$ = Br; R$^3$ = CH$_3$;
Z—R$^4$ = OCHF$_2$; R$^5$ = Cl)

| No. | R$^1$ | m.p./MS [mz$^{-1}$]/ $^1$H—NMR [ppm] |
|---|---|---|
| Ig.192 | [1,3-dioxolane with CH bearing two CO—OC$_2$H$_5$ groups] | |
| Ig.193 | —CH=CH—[1,3-dioxane with CH$_3$ substituent] | |
| Ig.194 | —CH=CH—CO-(2-methoxycarbonylpyrrolidin-1-yl) | |
| Ig.195 | —CH=CH—P(O)(OH)$_2$ | |
| Ig.196 | —CH=CH—P(O)(OC$_2$H$_5$)$_2$ | |
| Ig.197 | —CH$_2$—P(O)(OH)$_2$ | |
| Ig.198 | —CH$_2$—P(O)(OC$_2$H$_5$)$_2$ | |
| Ig.199 | —P(O)(OH)$_2$ | |
| Ig.200 | —P(O)(OC$_2$H$_5$)$_2$ | |
| Ig.201 | —OCH$_2$—CO—OCH$_2$—CH=N—OCH$_3$ | |
| Ig.202 | —CO—OCH$_2$—CH=N—OCH$_2$—CH=CH$_2$ | |
| Ig.203 | —CO—OCH$_2$—CH=N—OCH$_2$—CH=CHCl | |
| Ig.204 | —CO—OCH$_2$—CH=N—OCH$_2$—CH$_2$—C$_2$H$_5$ | |
| Ig.205 | —CO—OCH$_2$—CH=N—OCH$_2$—phenyl | |
| Ig.206 | —CO—NH—CH$_2$—CO—OCH$_3$ | |
| Ig.207 | —CO—NH—CH(CH(CH$_3$)$_2$)—CO—OC$_2$H$_5$ | |
| Ig.208 | —CO—N(CH$_3$)—CH$_2$—CO—OCH$_3$ | |
| Ig.209 | —CO—N(CH$_3$)—CH$_2$—CO—OC$_2$H$_5$ | |
| Ig.210 | —C(SCH$_3$)=N—OH | |
| Ig.211 | —C(SCH$_3$)=N—OCH$_2$—CO—OC$_2$H$_5$ | |
| Ig.212 | —C(SCH$_3$)=N—O—CO—CH$_3$ | |
| Ig.213 | —C(CN)=N—OH | |
| Ig.214 | —C(CN)=N—OCH$_2$—CO—OC$_2$H$_5$ | |
| Ig.215 | —C(CN)=N—O—CO—CH$_3$ | |
| Ig.216 | —CO—NH-(tetrahydrofuran-2-on-3-yl) | |
| Ig.217 | —Cl | |
| Ig.218 | —Br | |
| Ig.219 | —I | |
| Ig.220 | —CN | |
| Ig.221 | —CH=CH—CO—CH(OCH$_3$)$_2$ | |
| Ig.222 | —CH=CH—CO—CH(OC$_2$H$_5$)$_2$ | |
| Ig.223 | —CH=CH—[1,3-dioxolane] | |
| Ig.224 | —CH=CH—[1,3-dioxane] | |

TABLE 7-continued $(R^2 = Br; R^3 = CH_3;$
$Z—R^4 = OCHF_2; R^5 = Cl)$

| No. | $R^1$ | m.p./MS $[mz^{-1}]$/ $^1H$—NMR [ppm] |
|---|---|---|
| Ig.225 | —O—CO—CH$_3$ | |
| Ig.226 | —O—CO—C$_2$H$_5$ | |
| Ig.227 | —O—CO—CH$_2$-phenyl | |
| Ig.228 | —O—CO-cyclohexyl | |
| Ig.229 | —O—CO—CH$_2$—OCH$_3$ | |
| Ig.230 | —O—CO—NH—CH$_3$ | |
| Ig.231 | —O—CO—N(CH$_3$)$_2$ | |
| Ig.232 | —O—CO—NH-phenyl | |
| Ig.233 | —O—CO—NH—C$_2$H$_5$ | |
| Ig.234 | —O—CO—N(C$_2$H$_5$)$_2$ | |
| Ig.235 | —O—CO—NH$_2$ | |
| Ig.236 | —O—CS—N(CH$_3$)$_2$ | |
| Ig.237 | —O—CS—N(C$_2$H$_5$)$_2$ | |
| Ig.238 | —O—CS—NH$_2$ | |
| Ig.239 | —CO—NH—CH$_3$ | |
| Ig.240 | —CO—NH—C$_2$H$_5$ | |
| Ig.241 | —CO—NH—CH$_2$—C$_2$H$_5$ | |
| Ig.242 | —CO—NH—CH$_2$—CH$_2$—C$_2$H$_5$ | |
| Ig.243 | —CO—NH—CH(CH$_3$)$_2$ | |
| Ig.244 | —CO—N(CH$_3$)$_2$ | |
| Ig.245 | —CO—N(C$_2$H$_5$)$_2$ | |
| Ig.246 | —CO—N(pyrrolidinyl) | |
| Ig.247 | —CO—N(piperidinyl) | |
| Ig.248 | —CO—N(morpholinyl) | |

Use Examples

The herbicidal activity of the substituted 3-phenylpyrazoles of the formula I was demonstrated by greenhouse trials:

The cultivation vessels used were plastic flowerpots containing loamy sand with about 3.0% humus as substrate. The seeds of the test plants were sown separately according to species.

In the case of pre-emergence treatment, the active compounds suspended or emulsified in water were applied directly after sowing by means of finely distributing nozzles. The vessels were lightly watered in order to promote germination and growth, and then covered with transparent plastic hoods until the plants had taken root. This covering effects uniform germination of the test plants, provided this has not been adversely affected by the active compounds.

For the purpose of post-emergence treatment, the test plants were first raised, depending on growth form, to a height of growth of from 3 to 15 cm and only then were treated with the active compounds suspended or emulsified in water. For this purpose, the test plants were either sown directly and raised in the same vessels or first raised separately as seedlings and transplanted into the test vessels a few days before treatment. The application rate for post-emergence treatment was 3.0 kg of active substance per hectare.

Depending on species the plants were kept at 10–25° C. or 20–35° C. The trial period extended over 2 to 4 weeks. During this time, the plants were tended and their reaction to the individual treatments was assessed.

Rating was carried out on a scale of 0 to 100. On this scale 100 means no emergence of the plants or complete destruction of at least the above-ground parts, and 0 means no damage or normal course of growth.

The plants used in the greenhouse trials were made up of the following species:

| Botanical name | Common name |
| --- | --- |
| *Echinochloa crus-galli* | Barnyard grass |
| *Galium aparine* | Catchweed bedstraw |
| *Ipomoea subspecies* | Morning glory |
| *Setaria italica* | Foxtail millet |

Applied post-emergence at a rate of 3.0 kg/ha a.s., compound No. Ia.071 provided very good control of unwanted plants.

I claim:

1. A 3-phenylpyrazole of the formula I

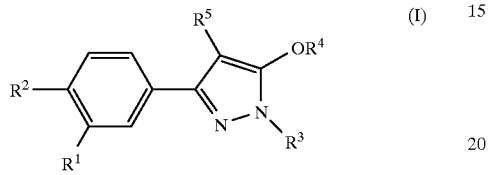

in which $R^1$ is —A—CO—$OR^6$,

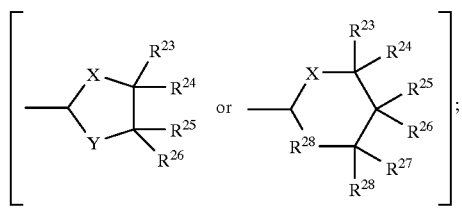

$R^2$ is cyano, trifluoromethyl or halogen;

$R^3$ is hydrogen, $C_1$–$C_4$-alkyl or $C_1$–$C_4$-haloalkyl;

$R^4$ is $C_1$–$C_4$-alkyl or $C_1$–$C_4$-haloalkyl;

$R^5$ is halogen;

A is a chemical bond, methylene, ethylene, 1,3-propylene or 1,4-butylene;

$R^6$ is hydrogen, $C_1$–$C_8$-alkyl, $C_1$–$C_8$-haloalkyl, $C_3$–$C_7$-cycloalkyl which may in turn carry from one to three $C_1$–$C_3$-alkyl radicals, $C_3$–$C_6$-alkenyl, $C_5$–$C_7$-cycloalkenyl which may in turn carry from one to three $C_1$–$C_3$-alkyl radicals, $C_3$–$C_6$-haloalkenyl, cyano-$C_1$–$C_8$-alkyl, $C_3$–$C_6$-alkynyl, $C_1$–$C_4$-alkoxy-$C_1$–$C_4$-alkyl, 2-tetrahydrofuryl-$C_1$–$C_8$-alkyl, 3-oxetanyl, 3-thietanyl, carboxyl-$C_1$–$C_6$-alkyl , ($C_1$–$C_8$-alkoxy) carbonyl-$C_1$–$C_6$-alkyl, $C_1$–$C_4$-alkoxy-($C_1$–$C_4$-alkoxy) carbonyl-$C_1$–$C_6$-alkyl, cyclopropylmethyl, (1-methylthiocycloprop-1-yl)methyl, $C_3$–$C_9$-(a-alkylakylidene)iminooxy-$C_1$–$C_6$-alkyl, ($C_1$–$C_4$-alkyl) carbonyl, $C_1$–$c_4$-alkyl which is substituted by —C($R^{19}$)=N—O—($C_1$–$C_4$-alkyl), —C($R^{19}$=N—O—($C_1$–$C_4$-haloalkyl), —C($R^{19}$)=N—O—($C_3$–$C_6$-alkenyl), —C($R^{19}$=N—O—($C_3$–$C_6$-haloalkenyl) or —C($R^{19}$) =N—O—($C_1$–$C_4$-alkyl)-$R^{34}$, phenyl, phenl-$C_1$–$C_6$-alkyl, phenyl-$C_2$–$C_6$-alkenyl, phenyl-$C_3$–$C_6$-alkynyl or phenoxy-$C_1$–$C_6$-alkyl, the phenyl ring being able in each case to be unsubstituted or in turn to carry from one to three radicals selected from the group consisting of halogen, nitro, cyano, $C_1$–$C_4$-alkyl, $C_1$–$C_4$-alkoxy, $C_1$–$C_4$-alkylthio, $C_1$–$C_4$-haloalkyl and $C_2$–$C_6$-alkenyl, 5- or 6-membered heteroaryl, heteroaryl-$C_1$–$C_6$-alkyl, heteroaryl-$C_3$–$C_6$-alkenyl, heteroaryl-$C_3$–$C_6$-alkynyl or heteroaryloxy-$C_1$–$C_6$-alkyl, the heteroaromatic radical containing in each case from one to three heteroatoms selected from the group consisting of one or two nitrogen atoms, and one oxygen or sulfur atom, and the heteroaromatic radical being able to carry on each substitutable ring member a radical selected from the group consisting of hydroxyl, halogen, $C_1$–$C_4$-haloalkyl, $C_1$–$C_4$-alkoxy, $C_1$–$C_4$-alkylthio and $C_1$–$C_4$-alkyl;

$R^{19}$ is hydrogen, $C_1$–$C_4$-alkyl, phenyl or benzyl;

$R^{34}$ is phenyl or 5- or 6-membered heteroaryl containing one to three heteroatoms selected from the group consisting of two nitrogen atoms and one oxygen or sulfur atoms, each phenyl or heteroaryl ring bring able to be unsubstituted or to carry one each substitutable ring member a substituent selected from the group consisting of hydroxyl, nitro, cyano, halogen, $C_1$–$C_4$-alkyl, $C_1$–$C_4$-haloalkyl, $C_1$–$C_4$-alkoxy and $C_1$–$C_4$-alkylthio, or an agriculturally usable salt of I.

2. A herbicidal composition comprising liquid and/or solid carriers and if desired at least one adjuvant and a herbicidally active quantity of at least one substituted 3-phenylpyrazole of the formula I or a salt of I, as claimed in claim 1.

3. A method of producing herbicidally active compositions, which comprises mixing a herbicidally active quantity of at least one substituted 3-phenylpyrazole of the formula I or a salt of I, as claimed in claim 1, with liquid and/or solid carriers an if desired at least one adjuvant.

4. A method of controlling unwanted plant growth, which comprises allowing a herbicidally active quantity of at least one substituted 3-phenylpyrazole of the formula I or a salt of I, as claimed in claim 1, to act on plants, their habitat or on seeds.

5. The 3-phenylpyrazole of the formula I as defined in claim 1, wherein $R^3$ is $C_1$–$C_4$-alkyl;

$R^4$ is $C_1$–$C_4$-haloalkyl;

A is a chemical bond;

$R^6$ is hydrogen, $C_1$–$C_8$-alkyl, $C_3$–$C_6$-alkenyl, $C_3$–$C_6$-alkynyl, carboxyl-$C_1$–$C_6$-alkyl or ($C_1$–$C_8$-alkoxy) carbonyl-$C_1$–$C_6$-alkyl.

6. The 3-phenylpyrazole of the formula I as defined in claim 1, wherein $R^2$ is halogen.

7. The 3-phenylpyrazole of the formula I as defined in claim 1, wherein A is a chemical bond.

* * * * *

UNITED STATES PATENT AND TRADEMARK OFFICE
CERTIFICATE OF CORRECTION

PATENT NO. : 5,928,999
DATED : July 27, 1999
INVENTOR(S) : VON DEM BUSSCHE-HUENNEFELD et al.

It is certified that error appears in the above-identified patent and that said Letters Patent is hereby corrected as shown below:

Col. 97, claim 1, delete the formula shown on lines 26-34.
Col. 97, claim 1, line 55, "$C_1$-$c_4$-alkyl" should be --$C_1$-$C_4$-alkyl--.
Col. 98, claim 2, line 30, "liquid and/or" should be --a liquid or--.
Col. 98, claim 2, line 31, "carriers and if desired at least one" should be --carrier and optionally an--.
Col. 98, claim 2, line 32, "at least one substituted" should be --a--.
Col. 98, claim 2, line 33, "claimed" should be --defined--.
Col. 98, claim 3, line 35, insert --a-- after "producing--.
Col. 98, claim 3, line 36, "compositions" should be --composition--.
Col. 98, claim 3, line 37, "at least one substituted" should be --a--.
Col. 98, claim 3, line 38, "claimed" should be --defined--; insert --a-- after "with".
Col. 98, claim 3, line 39, "and/or solid carriers an if desired at least one" should be --or solid carrier and optionally an--.
Col. 98, claim 4, line 41 bridging line 42, "at least one substituted" should read --a--.
Col. 98, claim 4, line 43, "claimed" should be --defined--.

Signed and Sealed this

Fourteenth Day of March, 2000

Attest:

Q. TODD DICKINSON

Attesting Officer

Commissioner of Patents and Trademarks